(12) United States Patent  
Jain et al.

(10) Patent No.: US 9,192,661 B2  
(45) Date of Patent: Nov. 24, 2015

(54) DELIVERY OF SELF-REPLICATING RNA USING BIODEGRADABLE POLYMER PARTICLES

(75) Inventors: Siddhartha Jain, Troy, NY (US); Derek O'Hagan, Winchester, MA (US); Manmohan Singh, Cary, NC (US)

(73) Assignee: Novartis AG (CH)

( * ) Notice: Subject to any disclaimer, the term of this patent is extended or adjusted under 35 U.S.C. 154(b) by 100 days.

(21) Appl. No.: 13/808,245

(22) PCT Filed: Jun. 7, 2011

(86) PCT No.: PCT/US2011/043086
§ 371 (c)(1),
(2), (4) Date: Apr. 1, 2013

(87) PCT Pub. No.: WO2012/006359
PCT Pub. Date: Jan. 12, 2012

(65) Prior Publication Data
US 2013/0183355 A1  Jul. 18, 2013

Related U.S. Application Data

(60) Provisional application No. 61/361,907, filed on Jul. 6, 2010.

(51) Int. Cl.
| | |
|---|---|
| *A61K 39/385* | (2006.01) |
| *A61K 9/16* | (2006.01) |
| *A61K 9/51* | (2006.01) |
| *A61K 39/155* | (2006.01) |
| *C12N 15/86* | (2006.01) |
| *C12N 15/88* | (2006.01) |
| *A61K 39/12* | (2006.01) |
| *A61K 39/00* | (2006.01) |

(52) U.S. Cl.
CPC ............. *A61K 39/385* (2013.01); *A61K 9/1617* (2013.01); *A61K 9/1647* (2013.01); *A61K 9/5123* (2013.01); *A61K 9/5153* (2013.01); *A61K 39/12* (2013.01); *A61K 39/155* (2013.01); *C12N 15/86* (2013.01); *C12N 15/88* (2013.01); A61K 2039/5256 (2013.01); A61K 2039/53 (2013.01); A61K 2039/55555 (2013.01); C12N 2760/18534 (2013.01); C12N 2770/36143 (2013.01)

(58) Field of Classification Search
CPC ............... A61K 2039/53; A61K 2039/55555; A61K 39/155; A61K 39/385; A61K 9/1617; A61K 9/1647; A61K 9/5123; A61K 9/5153; C07K 16/44; C12N 15/86; C12N 15/88; C12N 2770/36143; G01N 33/82
USPC ......... 424/193.1, 196.11, 197.11, 400, 141.1, 424/157.1, 9.34; 435/326, 328, 345, 452, 435/69.6, 7.1, 7.92
See application file for complete search history.

(56) References Cited

U.S. PATENT DOCUMENTS

2003/0138453 A1* 7/2003 O'Hagan et al. ........... 424/199.1
2010/0285135 A1* 11/2010 Wendorf et al. .............. 424/489

OTHER PUBLICATIONS

Tahara et al: "Establishing chitosan coated PLGA nanosphere platform loaded with wide variety of nucleic acid by complexation with cationic compound for gene delivery", International Journal of Pharmaceutics, vol. 354, No. 1-2, Feb. 21, 2008, pp. 210-216.*
Baoum, A., et al., "Cationic Surface Modification of PLG Nanoparticles Offers Sustained Gene Delivery to Pulmonary Epithelial Cells," J. Pharma. Sciences, vol. 99(5): 2413-2422 (2009).
Pan, C-H., et al., "Dose-Dependent Protection against or Exacerbation of Disease by a Polylactide Glycolide Microparticle-Adsorbed, Alphavirus-Based Measles Virus DNA Vaccine in Rhesus Macaques," Clin. Vacc. Immunol., vol. 15(4): 697-706 (Apr. 2008).
Goodsell, A., et al., "Beta-7-integrin-independent enhancement of mucosal and systemic anti-HIV antibody responses following combined mucosal and systemic gene delivery," Immunol., vol. 123: 378-389 (2007).
Tahara, K., et al., "Establishing chitosan coated PLGA nanosphere platform loaded with wide variety of nucleic acid by complexation with cationic compound for gene delivery," Intl. J. Pharma., vol. 354: 210-216 (2008).
International Preliminary Report on Patentability and International Search Report issued for PCT/US2011/043086 dated Oct. 31, 2011, (3 pages).

* cited by examiner

*Primary Examiner* — Janet Epps-Smith
(74) *Attorney, Agent, or Firm* — Laurence Shumway

(57) ABSTRACT

Particle compositions comprising adsorbed RNA replicons as well as methods of making and using the same are described.

26 Claims, 24 Drawing Sheets

FIG. 1A

Figure 4:
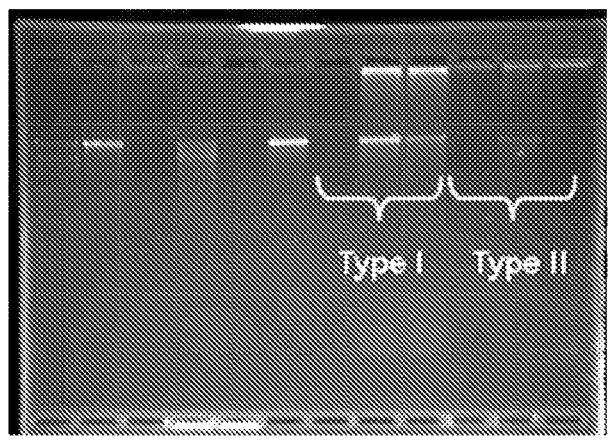

ATAGGCGGCGCATGAGAGAAGCCCAGACCAATTACCTACCCAAAATGGAGAAAGTTCACGTT
GACATCGAGGAAGACAGCCCATTCCTCAGAGCTTTGCAGCGGAGCTTCCCGCAGTTTGAGGT
AGAAGCCAAGCAGGTCACTGATAATGACCATGCTAATGCCAGAGCGTTTTCGCATCTGGCTT
CAAAACTGATCGAAACGGAGGTGGACCCATCCGACACGATCCTTGACATTGGAAGTGCGCCC
GCCCGCAGAATGTATTCTAAGCACAAGTATCATTGTATCTGTCCGATGAGATGTGCGGAAGA
TCCGGACAGATTGTATAAGTATGCAACTAAGCTGAAGAAAACTGTAAGGAAATAACTGATA
AGGAATTGGACAAGAAATGAAGGAGCTCGCCGCCGTCATGAGCGACCCTGACCTGGAAACT
GAGACTATGTGCCTCCACGACGACGAGTCGTGTCGCTACGAAGGGCAAGTCGCTGTTTACCA
GGATGTATACGCGGTTGACGGACCGACAAGTCTCTATCACCAAGCCAATAAGGGAGTTAGAG
TCGCCTACTGGATAGGCTTTGACACCACCCCTTTTATGTTTAAGAACTTGGCTGGAGCATAT
CCATCATACTCTACCAACTGGGCCGACGAAACCGTGTTAACGGCTCGTAACATAGGCCTATG
CAGCTCTGACGTTATGGAGCGGTCACGTAGAGGGATGTCCATTCTTAGAAAGAAGTATTTGA
AACCATCCAACAATGTTCTATTCTCTGTTGGCTCGACCATCTACCACGAGAAGAGGGACTTA
CTGAGGAGCTGGCACCTGCCGTCTGTATTTCACTTACGTGGCAAGCAAAATTACACATGTCG
GTGTGAGACTATAGTTAGTTGCGACGGGTACGTCGTTAAAAGAATAGCTATCAGTCCAGGCC
TGTATGGGAAGCCTTCAGGCTATGCTGCTACGATGCACCGCGAGGGATTCTTGTGCTGCAAA
GTGACAGACACATTGAACGGGGAGAGGGTCTCTTTTCCCGTGTGCACGTATGTGCCAGCTAC
ATTGTGTGACCAAATGACTGGCATACTGGCAACAGATGTCAGTGCGGACGACGCGCAAAAAC
TGCTGGTTGGGCTCAACCAGCGTATAGTCGTCAACGGTCGCACCCAGAGAAACACCAATACC
ATGAAAAATTACCTTTTGCCCGTAGTGGCCCAGGCATTTGCTAGGTGGGCAAAGGAATATAA
GGAAGATCAAGAAGATGAAAGGCCACTAGGACTACGAGATAGACAGTTAGTCATGGGGTGTT
GTTGGGCTTTTAGAAGGCACAAGATAACATCTATTTATAAGCGCCCGGATACCCAAACCATC
ATCAAAGTGAACAGCGATTTCCACTCATTCGTGCTGCCCAGGATAGGCAGTAACACATTGGA
GATCGGGCTGAGAACAAGAATCAGGAAAATGTTAGAGGAGCACAAGGAGCCGTCACCTCTCA
TTACCGCCGAGGACGTACAAGAAGCTAAGTGCGCAGCCGATGAGGCTAAGGAGGTGCGTGAA
GCCGAGGAGTTGCGCGCAGCTCTACCACCTTTGGCAGCTGATGTTGAGGAGCCCACTCTGGA
AGCCGATGTAGACTTGATGTTACAAGAGGCTGGGGCCGGCTCAGTGGAGACACCTCGTGGCT
TGATAAAGGTTACCAGCTACGATGGCGAGGACAAGATCGGCTCTTACGCTGTGCTTTCTCCG
CAGGCTGTACTCAAGAGTGAAAAATTATCTTGCATCCACCCTCTCGCTGAACAAGTCATAGT
GATAACACACTCTGGCCGAAAAGGGCGTTATGCCGTGGAACCATACCATGGTAAAGTAGTGG
TGCCAGAGGGACATGCAATACCCGTCCAGGACTTTCAAGCTCTGAGTGAAAGTGCCACCATT
GTGTACAACGAACGTGAGTTCGTAAACAGGTACCTGCACCATATTGCCACACATGGAGGAGC
GCTGAACACTGATGAAGAATATTACAAAACTGTCAAGCCCAGCGAGCACGACGGCGAATACC
TGTACGACATCGACAGGAAACAGTGCGTCAAGAA

FIG. 1B

```
AGAACTAGTCACTGGGCTAGGGCTCACAGGCGAGCTGGTGGATCCTCCCTTCCATGAATTCG
CCTACGAGAGTCTGAGAACACGACCAGCCGCTCCTTACCAAGTACCAACCATAGGGGTGTAT
GGCGTGCCAGGATCAGGCAAGTCTGGCATCATTAAAAGCGCAGTCACCAAAAAAGATCTAGT
GGTGAGCGCCAAGAAAGAAAACTGTGCAGAAATTATAAGGGACGTCAAGAAAATGAAAGGGC
TGGACGTCAATGCCAGAACTGTGGACTCAGTGCTCTTGAATGGATGCAAACACCCCGTAGAG
ACCCTGTATATTGACGAAGCTTTTGCTTGTCATGCAGGTACTCTCAGAGCGCTCATAGCCAT
TATAAGACCTAAAAAGGCAGTGCTCTGCGGGGATCCCAAACAGTGCGGTTTTTTTAACATGA
TGTGCCTGAAAGTGCATTTTAACCACGAGATTTGCACACAAGTCTTCCACAAAAGCATCTCT
CGCCGTTGCACTAAATCTGTGACTTCGGTCGTCTCAACCTTGTTTTACGACAAAAAAATGAG
AACGACGAATCCGAAAGAGACTAAGATTGTGATTGACACTACCGGCAGTACCAAACCTAAGC
AGGACGATCTCATTCTCACTTGTTTCAGAGGGTGGGTGAAGCAGTTGCAAATAGATTACAAA
GGCAACGAAATAATGACGGCAGCTGCCTCTCAAGGGCTGACCCGTAAAGGTGTGTATGCCGT
TCGGTACAAGGTGAATGAAAATCCTCTGTACGCACCCACCTCAGAACATGTGAACGTCCTAC
TGACCCGCACGGAGGACCGCATCGTGTGGAAAACACTAGCCGGCGACCCATGGATAAAAACA
CTGACTGCCAAGTACCCTGGGAATTTCACTGCCACGATAGAGGAGTGGCAAGCAGAGCATGA
TGCCATCATGAGGCACATCTTGGAGAGACCGGACCCTACCGACGTCTTCCAGAATAAGGCAA
ACGTGTGTTGGGCCAAGGCTTTAGTGCCGGTGCTGAAGACCGCTGGCATAGACATGACCACT
GAACAATGGAACACTGTGGATTATTTTGAAACGGACAAAGCTCACTCAGCAGAGATAGTATT
GAACCAACTATGCGTGAGGTTCTTTGGACTCGATCTGGACTCCGGTCTATTTTCTGCACCCA
CTGTTCCGTTATCCATTAGGAATAATCACTGGGATAACTCCCCGTCGCCTAACATGTACGGG
CTGAATAAAGAAGTGGTCCGTCAGCTCTCTCGCAGGTACCCACAACTGCCTCGGGCAGTTGC
CACTGGAAGAGTCTATGACATGAACACTGGTACACTGCGCAATTATGATCCGCGCATAAACC
TAGTACCTGTAAACAGAAGACTGCCTCATGCTTTAGTCCTCCACCATAATGAACACCCACAG
AGTGACTTTTCTTCATTCGTCAGCAAATTGAAGGGCAGAACTGTCCTGGTGGTCGGGAAAA
GTTGTCCGTCCCAGGCAAAATGGTTGACTGGTTGTCAGACCGGCCTGAGGCTACCTTCAGAG
CTCGGCTGGATTTAGGCATCCCAGGTGATGTGCCCAAATATGACATAATATTTGTTAATGTG
AGGACCCCATATAAATACCATCACTATCAGCAGTGTGAAGACCATGCCATTAAGCTTAGCAT
GTTGACCAAGAAAGCTTGTCTGCATCTGAATCCCGGCGGAACCTGTGTCAGCATAGGTTATG
GTTACGCTGACAGGGCCAGCGAAAGCATCATTGGTGCTATAGCGCGGCAGTTCAAGTTTTCC
CGGGTATGCAAACCGAAATCCTCACTTGAAGAGACGGAAGTTCTGTTTGTATTCATTGGGTA
CGATCGCAAGGCCCGTACGCACAATCCTTACAAGCTTTCATCAACCTTGACCAACATTTATA
CAGGTTCCAGACTCCACGAAGCCGGATGTGCACCCTCATATCATGTGGTGCGAGGGGATATT
GCCACGGCCACCGAAGGAGTGATTATAAATGCTGCTAACAGCAAAGGACAACCTGGCGGAGG
GGTGTGCGGAGCGCTGTATAAGAAATTCCCGGAA
```

FIG. 1C

AGCTTCGATTTACAGCCGATCGAAGTAGGAAAAGCGCGACTGGTCAAAGGTGCAGCTAAACA
TATCATTCATGCCGTAGGACCAAACTTCAACAAAGTTTCGGAGGTTGAAGGTGACAAACAGT
TGGCAGAGGCTTATGAGTCCATCGCTAAGATTGTCAACGATAACAATTACAAGTCAGTAGCG
ATTCCACTGTTGTCCACCGGCATCTTTTCCGGGAACAAAGATCGACTAACCCAATCATTGAA
CCATTTGCTGACAGCTTTAGACACCACTGATGCAGATGTAGCCATATACTGCAGGGACAAGA
AATGGGAAATGACTCTCAAGGAAGCAGTGGCTAGGAGAGAAGCAGTGGAGGAGATATGCATA
TCCGACGACTCTTCAGTGACAGAACCTGATGCAGAGCTGGTGAGGGTGCATCCGAAGAGTTC
TTTGGCTGGAAGGAAGGGCTACAGCACAAGCGATGGCAAAACTTTCTCATATTTGGAAGGGA
CCAAGTTTCACCAGGCGGCCAAGGATATAGCAGAAATTAATGCCATGTGGCCCGTTGCAACG
GAGGCCAATGAGCAGGTATGCATGTATATCCTCGGAGAAAGCATGAGCAGTATTAGGTCGAA
ATGCCCCGTCGAAGAGTCGGAAGCCTCCACACCACCTAGCACGCTGCCTTGCTTGTGCATCC
ATGCCATGACTCCAGAAAGAGTACAGCGCCTAAAAGCCTCACGTCCAGAACAAATTACTGTG
TGCTCATCCTTTCCATTGCCGAAGTATAGAATCACTGGTGTGCAGAAGATCCAATGCTCCCA
GCCTATATTGTTCTCACCGAAAGTGCCTGCGTATATTCATCCAAGGAAGTATCTCGTGGAAA
CACCACCGGTAGACGAGACTCCGGAGCCATCGGCAGAGAACCAATCCACAGAGGGGACACCT
GAACAACCACCACTTATAACCGAGGATGAGACCAGGACTAGAACGCCTGAGCCGATCATCAT
CGAAGAGGAAGAAGAGGATAGCATAAGTTTGCTGTCAGATGGCCCGACCCACCAGGTGCTGC
AAGTCGAGGCAGACATTCACGGGCCGCCCTCTGTATCTAGCTCATCCTGGTCCATTCCTCAT
GCATCCGACTTTGATGTGGACAGTTTATCCATACTTGACACCCTGGAGGGAGCTAGCGTGAC
CAGCGGGGCAACGTCAGCCGAGACTAACTCTTACTTCGCAAAGAGTATGGAGTTTCTGGCGC
GACCGGTGCCTGCGCCTCGAACAGTATTCAGGAACCCTCCACATCCCGCTCCGCGCACAAGA
ACACCGTCACTTGCACCCAGCAGGGCCTGCTCGAGAACCAGCCTAGTTTCCACCCCGCCAGG
CGTGAATAGGGTGATCACTAGAGAGGAGCTCGAGGCGCTTACCCCGTCACGCACTCCTAGCA
GGTCGGTCTCGAGAACCAGCCTGGTCTCCAACCCGCCAGGCGTAAATAGGGTGATTACAAGA
GAGGAGTTTGAGGCGTTCGTAGCACAACAACAATGACGGTTTGATGCGGGTGCATACATCTT
TTCCTCCGACACCGGTCAAGGGCATTTACAACAAAAATCAGTAAGGCAAACGGTGCTATCCG
AAGTGGTGTTGGAGAGGACCGAATTGGAGATTTCGTATGCCCCGCGCCTCGACCAAGAAAAA
GAAGAATTACTACGCAAGAAATTACAGTTAAATCCCACACCTGCTAACAGAAGCAGATACCA
GTCCAGGAAGGTGGAGAACATGAAAGCCATAACAGCTAGACGTATTCTGCAAGGCCTAGGGC
ATTATTTGAAGGCAGAAGGAAAAGTGGAGTGCTACCGAACCCTGCATCCTGTTCCTTTGTAT
TCATCTAGTGTGAACCGTGCCTTTTCAAGCCCCAAGGTCGCAGTGGAAGCCTGTAACGCCAT
GTTGAAAGAGAACTTTCCGACTGTGGCTTCTTACTGTATTATTCCAGAGTACGATGCCTATT
TGGACATGGTTGACGGAGCTTCATGCTGCTTAGACACTGCCAGTTTTTGCCCTGCAAAGCTG
CGCAGCTTTCCAAAGAAACACTCCTATTTGGAAC

FIG. 1D

```
CCACAATACGATCGGCAGTGCCTTCAGCGATCCAGAACACGCTCCAGAACGTCCTGGCAGCT
GCCACAAAAGAAATTGCAATGTCACGCAAATGAGAGAATTGCCCGTATTGGATTCGGCGGC
CTTTAATGTGGAATGCTTCAAGAAATATGCGTGTAATAATGAATATTGGGAAACGTTTAAAG
AAAACCCCATCAGGCTTACTGAAGAAAACGTGGTAAATTACATTACCAAATTAAAAGGACCA
AAAGCTGCTGCTCTTTTTGCGAAGACACATAATTTGAATATGTTGCAGGACATACCAATGGA
CAGGTTTGTAATGGACTTAAAGAGAGACGTGAAAGTGACTCCAGGAACAAAACATACTGAAG
AACGGCCCAAGGTACAGGTGATCCAGGCTGCCGATCCGCTAGCAACAGCGTATCTGTGCGGA
ATCCACCGAGAGCTGGTTAGGAGATTAAATGCGGTCCTGCTTCCGAACATTCATACACTGTT
TGATATGTCGGCTGAAGACTTTGACGCTATTATAGCCGAGCACTTCCAGCCTGGGGATTGTG
TTCTGGAAACTGACATCGCGTCGTTTGATAAAAGTGAGGACGACGCCATGGCTCTGACCGCG
TTAATGATTCTGGAAGACTTAGGTGTGGACGCAGAGCTGTTGACGCTGATTGAGGCGGCTTT
CGGCGAAATTTCATCAATACATTTGCCCACTAAAACTAAATTTAAATTCGGAGCCATGATGA
AATCTGGAATGTTCCTCACACTGTTTGTGAACACAGTCATTAACATTGTAATCGCAAGCAGA
GTGTTGAGAGAACGGCTAACCGGATCACCATGTGCAGCATTCATTGGAGATGACAATATCGT
GAAAGGAGTCAAATCGGACAAATTAATGGCAGACAGGTGCGCCACCTGGTTGAATATGGAAG
TCAAGATTATAGATGCTGTGGTGGGCGAGAAAGCGCCTTATTTCTGTGGAGGGTTTATTTTG
TGTGACTCCGTGACCGGCACAGCGTGCCGTGTGGCAGACCCCCTAAAAAGGCTGTTTAAGCT
TGGCAAACCTCTGGCAGCAGACGATGAACATGATGATGACAGGAGAAGGGCATTGCATGAAG
AGTCAACACGCTGGAACCGAGTGGGTATTCTTTCAGAGCTGTGCAAGGCAGTAGAATCAAGG
TATGAAACCGTAGGAACTTCCATCATAGTTATGGCCATGACTACTCTAGCTAGCAGTGTTAA
ATCATTCAGCTACCTGAGAGGGGCCCCTATAACTCTCTACGGCTAACCTGAATGGACTACGA
CATAGTCTAGTCGACGCCACCATGGAACTGCTGATCCTGAAGGCCAACGCCATCACCACCAT
CCTGACCGCCGTGACCTTCTGCTTCGCCAGCGGCCAGAACATCACCGAGGAATTCTACCAGA
GCACCTGCAGCGCCGTGAGCAAGGGCTACCTGAGCGCCCTGCGGACCGGCTGGTACACCAGC
GTGATCACCATCGAGCTGTCCAACATCAAAGAAAACAAGTGCAACGGCACCGACGCCAAGGT
GAAACTGATCAAGCAGGAACTGGACAAGTACAAGAACGCCGTGACCGAGCTGCAGCTGCTGA
TGCAGAGCACCCCCGCCACCAACAACCGGGCCAGAAGAGAGCTGCCCCGGTTCATGAACTAC
ACCCTGAACAACGCCAAGAAAACCAACGTGACCCTGAGCAAGAAGCGGAAGCGGCGGTTCCT
GGGCTTCCTGCTGGGCGTGGGCAGCGCCATCGCCAGCGGGGTGGCCGTGTCCAAGGTGCTGC
ACCTGGAAGGCGAGGTGAACAAGATCAAGTCCGCCCTGCTGTCCACCAACAAGGCCGTGGTG
TCCCTGAGCAACGGCGTGAGCGTGCTGACCAGCAAGGTGCTGGATCTGAAGAACTACATCGA
CAAGCAGCTGCTGCCCATCGTGAACAAGCAGAGCTGCAGCATCAGCAACATCGAGACCGTGA
TCGAGTTCCAGCAGAAGAACAACCGGCTGCTGGAAATCACCCGGGAGTTCAGCGTGAACGCC
GGCGTGACCACCCCCGTGAGCACCTACATGCTGA
```

FIG. 1E

```
CCAACAGCGAGCTGCTGTCCCTGATCAATGACATGCCCATCACCAACGACCAGAAAAAGCTG
ATGAGCAACAACGTGCAGATCGTGCGGCAGCAGAGCTACTCCATCATGAGCATCATCAAAGA
AGAGGTGCTGGCCTACGTGGTGCAGCTGCCCCTGTACGGCGTGATCGACACCCCCTGCTGGA
AGCTGCACACCAGCCCCCTGTGCACCACCAACACCAAAGAGGGCAGCAACATCTGCCTGACC
CGGACCGACCGGGGCTGGTACTGCGACAACGCCGGCAGCGTGAGCTTCTTCCCCCAAGCCGA
GACCTGCAAGGTGCAGAGCAACCGGGTGTTCTGCGACACCATGAACAGCCTGACCCTGCCCT
CCGAGGTGAACCTGTGCAACGTGGACATCTTCAACCCCAAGTACGACTGCAAGATCATGACC
TCCAAGACCGACGTGAGCAGCTCCGTGATCACCTCCCTGGGCGCCATCGTGAGCTGCTACGG
CAAGACCAAGTGCACCGCCAGCAACAAGAACCGGGGCATCATCAAGACCTTCAGCAACGGCT
GCGACTACGTGAGCAACAAGGGCGTGGACACCGTGAGCGTGGGCAACACACTGTACTACGTG
AATAAGCAGGAAGGCAAGAGCCTGTACGTGAAGGGCGAGCCCATCATCAACTTCTACGACCC
CCTGGTGTTCCCCAGCGACGAGTTCGACGCCAGCATCAGCCAGGTCAACGAGAAGATCAACC
AGAGCCTGGCCTTCATCCGGAAGAGCGACGAGCTGCTGCACAATGTGAATGCCGGCAAGAGC
ACCACCAATATCATGATCACCACAATCATCATCGTGATCATTGTGATCCTGCTGTCTCTGAT
TGCCGTGGGCCTGCTGCTGTACTGCAAGGCCCGCAGCACCCCTGTGACCCTGTCCAAGGACC
AGCTGTCCGGCATCAACAATATCGCCTTCTCCAACTGAAGTCTAGACGGCGCGCCCACCCAG
CGGCCGCATACAGCAGCAATTGGCAAGCTGCTTACATAGAACTCGCGGCGATTGGCATGCCG
CCTTAAAATTTTTATTTTATTTTTCTTTTCTTTTCCGAATCGGATTTTGTTTTTAATATTTC
AAAAAAAAAAAAAAAAAAAAAAAAAAAAAAAAAAAGGGTCGGCATGGCATCTCCACCTCCTC
GCGGTCCGACCTGGGCATCCGAAGGAGGACGCACGTCCACTCGGATGGCTAAGGGAGAGCCA
CGTTTAAACCAGCTCCAATTCGCCCTATAGTGAGTCGTATTACGCGCGCTCACTGGCCGTCG
TTTTACAACGTCGTGACTGGGAAAACCCTGGCGTTACCCAACTTAATCGCCTTGCAGCACAT
CCCCCTTTCGCCAGCTGGCGTAATAGCGAAGAGGCCCGCACCGATCGCCCTTCCCAACAGTT
GCGCAGCCTGAATGGCGAATGGGACGCGCCCTGTAGCGGCGCATTAAGCGCGGCGGGTGTGG
TGGTTACGCGCAGCGTGACCGCTACACTTGCCAGCGCCCTAGCGCCCGCTCCTTTCGCTTTC
TTCCCTTCCTTTCTCGCCACGTTCGCCGGCTTTCCCCGTCAAGCTCTAAATCGGGGGCTCCC
TTTAGGGTTCCGATTTAGTGCTTTACGGCACCTCGACCCCAAAAAACTTGATTAGGGTGATG
GTTCACGTAGTGGGCCATCGCCCTGATAGACGGTTTTTCGCCCTTTGACGTTGGAGTCCACG
TTCTTTAATAGTGGACTCTTGTTCCAAACTGGAACAACACTCAACCCTATCTCGGTCTATTC
TTTTGATTTATAAGGGATTTTGCCGATTTCGGCCTATTGGTTAAAAAATGAGCTGATTTAAC
AAAAATTTAACGCGAATTTTAACAAAATATTAACGCTTACAATTTAGGTGGCACTTTTCGGG
GAAATGTGCGCGGAACCCCTATTTGTTTATTTTTCTAAATACATTCAAATATGTATCCGCTC
ATGAGACAATAACCCTGATAAATGCTTCAATAATATTGAAAAGGAAGAGTATGAGTATTCA
ACATTTCCGTGTCGCCCTTATTCCCTTTTTTGCG
```

FIG. 1F

```
GCATTTTGCCTTCCTGTTTTTGCTCACCCAGAAACGCTGGTGAAAGTAAAAGATGCTGAAGA
TCAGTTGGGTGCACGAGTGGGTTACATCGAACTGGATCTCAACAGCGGTAAGATCCTTGAGA
GTTTTCGCCCCGAAGAACGTTTTCCAATGATGAGCACTTTTAAAGTTCTGCTATGTGGCGCG
GTATTATCCCGTATTGACGCCGGGCAAGAGCAACTCGGTCGCCGCATACACTATTCTCAGAA
TGACTTGGTTGAGTACTCACCAGTCACAGAAAAGCATCTTACGGATGGCATGACAGTAAGAG
AATTATGCAGTGCTGCCATAACCATGAGTGATAACACTGCGGCCAACTTACTTCTGACAACG
ATCGGAGGACCGAAGGAGCTAACCGCTTTTTTGCACAACATGGGGGATCATGTAACTCGCCT
TGATCGTTGGGAACCGGAGCTGAATGAAGCCATACCAAACGACGAGCGTGACACCACGATGC
CTGTAGCAATGGCAACAACGTTGCGCAAACTATTAACTGGCGAACTACTTACTCTAGCTTCC
CGGCAACAATTAATAGACTGGATGGAGGCGGATAAAGTTGCAGGACCACTTCTGCGCTCGGC
CCTTCCGGCTGGCTGGTTTATTGCTGATAAATCTGGAGCCGGTGAGCGTGGGTCTCGCGGTA
TCATTGCAGCACTGGGGCCAGATGGTAAGCCCTCCCGTATCGTAGTTATCTACACGACGGGG
AGTCAGGCAACTATGGATGAACGAAATAGACAGATCGCTGAGATAGGTGCCTCACTGATTAA
GCATTGGTAACTGTCAGACCAAGTTTACTCATATATACTTTAGATTGATTTAAAACTTCATT
TTTAATTTAAAAGGATCTAGGTGAAGATCCTTTTTGATAATCTCATGACCAAAATCCCTTAA
CGTGAGTTTTCGTTCCACTGAGCGTCAGACCCCGTAGAAAAGATCAAAGGATCTTCTTGAGA
TCCTTTTTTTCTGCGCGTAATCTGCTGCTTGCAAACAAAAAAACCACCGCTACCAGCGGTGG
TTTGTTTGCCGGATCAAGAGCTACCAACTCTTTTTCCGAAGGTAACTGGCTTCAGCAGAGCG
CAGATACCAAATACTGTTCTTCTAGTGTAGCCGTAGTTAGGCCACCACTTCAAGAACTCTGT
AGCACCGCCTACATACCTCGCTCTGCTAATCCTGTTACCAGTGGCTGCTGCCAGTGGCGATA
AGTCGTGTCTTACCGGGTTGGACTCAAGACGATAGTTACCGGATAAGGCGCAGCGGTCGGGC
TGAACGGGGGGTTCGTGCACACAGCCCAGCTTGGAGCGAACGACCTACACCGAACTGAGATA
CCTACAGCGTGAGCTATGAGAAAGCGCCACGCTTCCCGAAGGGAGAAAGGCGGACAGGTATC
CGGTAAGCGGCAGGGTCGGAACAGGAGAGCGCACGAGGGAGCTTCCAGGGGGAAACGCCTGG
TATCTTTATAGTCCTGTCGGGTTTCGCCACCTCTGACTTGAGCGTCGATTTTTGTGATGCTC
GTCAGGGGGCGGAGCCTATGGAAAAACGCCAGCAACGCGGCCTTTTTACGGTTCCTGGCCT
TTTGCTGGCCTTTTGCTCACATGTTCTTTCCTGCGTTATCCCCTGATTCTGTGGATAACCGT
ATTACCGCCTTTGAGTGAGCTGATACCGCTCGCCGCAGCCGAACGACCGAGCGCAGCGAGTC
AGTGAGCGAGGAAGCGGAAGAGCGCCCAATACGCAAACCGCCTCTCCCCGCGCGTTGGCCGA
TTCATTAATGCAGCTGGCACGACAGGTTTCCCGACTGGAAAGCGGGCAGTGAGCGCAACGCA
ATTAATGTGAGTTAGCTCACTCATTAGGCACCCCAGGCTTTACACTTTATGCTCCCGGCTCG
TATGTTGTGTGGAATTGTGAGCGGATAACAATTTCACACAGGAAACAGCTATGACCATGATT
ACGCCAAGCGCGCAATTAACCCTCACTAAAGGGAACAAAAGCTGGGTACCGGGCCCACGCGT
AATACGACTCACTATAG
```

FIG. 2A

ATAGGCGGCGCATGAGAGAAGCCCAGACCAATTACCTACCCAAAATGGAGAAAGTTCACGTT
GACATCGAGGAAGACAGCCCATTCCTCAGAGCTTTGCAGCGGAGCTTCCCGCAGTTTGAGGT
AGAAGCCAAGCAGGTCACTGATAATGACCATGCTAATGCCAGAGCGTTTTCGCATCTGGCTT
CAAAACTGATCGAAACGGAGGTGGACCCATCCGACACGATCCTTGACATTGGAAGTGCGCCC
GCCCGCAGAATGTATTCTAAGCACAAGTATCATTGTATCTGTCCGATGAGATGTGCGGAAGA
TCCGGACAGATTGTATAAGTATGCAACTAAGCTGAAGAAAAACTGTAAGGAAATAACTGATA
AGGAATTGGACAAGAAATGAAGGAGCTCGCCGCCGTCATGAGCGACCCTGACCTGGAAACT
GAGACTATGTGCCTCCACGACGACGAGTCGTGTCGCTACGAAGGGCAAGTCGCTGTTTACCA
GGATGTATACGCGGTTGACGGACCGACAAGTCTCTATCACCAAGCCAATAAGGGAGTTAGAG
TCGCCTACTGGATAGGCTTTGACACCACCCCTTTTATGTTTAAGAACTTGGCTGGAGCATAT
CCATCATACTCTACCAACTGGGCCGACGAAACCGTGTTAACGGCTCGTAACATAGGCCTATG
CAGCTCTGACGTTATGGAGCGGTCACGTAGAGGGATGTCCATTCTTAGAAAGAAGTATTTGA
AACCATCCAACAATGTTCTATTCTCTGTTGGCTCGACCATCTACCACGAGAAGAGGGACTTA
CTGAGGAGCTGGCACCTGCCGTCTGTATTTCACTTACGTGGCAAGCAAAATTACACATGTCG
GTGTGAGACTATAGTTAGTTGCGACGGGTACGTCGTTAAAAGAATAGCTATCAGTCCAGGCC
TGTATGGGAAGCCTTCAGGCTATGCTGCTACGATGCACCGCGAGGGATTCTTGTGCTGCAAA
GTGACAGACACATTGAACGGGGAGAGGGTCTCTTTTCCCGTGTGCACGTATGTGCCAGCTAC
ATTGTGTGACCAAATGACTGGCATACTGGCAACAGATGTCAGTGCGGACGACGCGCAAAAAC
TGCTGGTTGGGCTCAACCAGCGTATAGTCGTCAACGGTCGCACCCAGAGAAACACCAATACC
ATGAAAAATTACCTTTTGCCCGTAGTGGCCCAGGCATTTGCTAGGTGGGCAAAGGAATATAA
GGAAGATCAAGAAGATGAAAGGCCACTAGGACTACGAGATAGACAGTTAGTCATGGGGTGTT
GTTGGGCTTTTAGAAGGCACAAGATAACATCTATTTATAAGCGCCCGGATACCCAAACCATC
ATCAAAGTGAACAGCGATTTCCACTCATTCGTGCTGCCCAGGATAGGCAGTAACACATTGGA
GATCGGGCTGAGAACAAGAATCAGGAAAATGTTAGAGGAGCACAAGGAGCCGTCACCTCTCA
TTACCGCCGAGGACGTACAAGAAGCTAAGTGCGCAGCCGATGAGGCTAAGGAGGTGCGTGAA
GCCGAGGAGTTGCGCGCAGCTCTACCACCTTTGGCAGCTGATGTTGAGGAGCCCACTCTGGA
AGCCGATGTAGACTTGATGTTACAAGAGGCTGGGGCCGGCTCAGTGGAGACACCTCGTGGCT
TGATAAAGGTTACCAGCTACGATGGCGAGGACAAGATCGGCTCTTACGCTGTGCTTTCTCCG
CAGGCTGTACTCAAGAGTGAAAAATTATCTTGCATCCACCCTCTCGCTGAACAAGTCATAGT
GATAACACACTCTGGCCGAAAAGGGCGTTATGCCGTGGAACCATACCATGGTAAAGTAGTGG
TGCCAGAGGGACATGCAATACCCGTCCAGGACTTTCAAGCTCTGAGTGAAAGTGCCACCATT
GTGTACAACGAACGTGAGTTCGTAAACAGGTACCTGCACCATATTGCCACACATGGAGGAGC
GCTGAACACTGATGAAGAATATTACAAAACT

FIG. 2B

```
GTCAAGCCCAGCGAGCACGACGGCGAATACCTGTACGACATCGACAGGAAACAGTGCGTCAA
GAAAGAACTAGTCACTGGGCTAGGGCTCACAGGCGAGCTGGTGGATCCTCCCTTCCATGAAT
TCGCCTACGAGAGTCTGAGAACACGACCAGCCGCTCCTTACCAAGTACCAACCATAGGGGTG
TATGGCGTGCCAGGATCAGGCAAGTCTGGCATCATTAAAAGCGCAGTCACCAAAAAGATCT
AGTGGTGAGCGCCAAGAAAGAAACTGTGCAGAATTATAAGGGACGTCAAGAAAATGAAAG
GGCTGGACGTCAATGCCAGAACTGTGGACTCAGTGCTCTTGAATGGATGCAAACACCCCGTA
GAGACCCTGTATATTGACGAAGCTTTTGCTTGTCATGCAGGTACTCTCAGAGCGCTCATAGC
CATTATAAGACCTAAAAGGCAGTGCTCTGCGGGATCCCAAACAGTGCGGTTTTTTAACA
TGATGTGCCTGAAAGTGCATTTTAACCACGAGATTTGCACACAAGTCTTCCACAAAAGCATC
TCTCGCCGTTGCACTAAATCTGTGACTTCGGTCGTCTCAACCTTGTTTTACGACAAAAAAAT
GAGAACGACGAATCCGAAAGAGACTAAGATTGTGATTGACACTACCGGCAGTACCAAACCTA
AGCAGGACGATCTCATTCTCACTTGTTTCAGAGGGTGGGTGAAGCAGTTGCAAATAGATTAC
AAAGGCAACGAAATAATGACGGCAGCTGCCTCTCAAGGGCTGACCCGTAAAGGTGTGTATGC
CGTTCGGTACAAGGTGAATGAAATCCTCTGTACGCACCCACCTCAGAACATGTGAACGTCC
TACTGACCCGCACGGAGGACCGCATCGTGTGGAAAACACTAGCCGGCGACCCATGGATAAAA
ACACTGACTGCCAAGTACCCTGGGAATTTCACTGCCACGATAGAGGAGTGGCAAGCAGAGCA
TGATGCCATCATGAGGCACATCTTGGAGAGACCGGACCCTACCGACGTCTTCCAGAATAAGG
CAAACGTGTGTTGGGCCAAGGCTTTAGTGCCGGTGCTGAAGACCGCTGGCATAGACATGACC
ACTGAACAATGGAACACTGTGGATTATTTTGAAACGGACAAAGCTCACTCAGCAGAGATAGT
ATTGAACCAACTATGCGTGAGGTTCTTTGGACTCGATCTGGACTCCGGTCTATTTTCTGCAC
CCACTGTTCCGTTATCCATTAGGAATAATCACTGGGATAACTCCCCGTCGCCTAACATGTAC
GGGCTGAATAAAGAAGTGGTCCGTCAGCTCTCTCGCAGGTACCCACAACTGCCTCGGGCAGT
TGCCACTGGAAGAGTCTATGACATGAACACTGGTACACTGCGCAATTATGATCCGCGCATAA
ACCTAGTACCTGTAAACAGAAGACTGCCTCATGCTTTAGTCCTCCACCATAATGAACACCCA
CAGAGTGACTTTTCTTCATTCGTCAGCAAATTGAAGGGCAGAACTGTCCTGGTGGTCGGGGA
AAAGTTGTCCGTCCCAGGCAAAATGGTTGACTGGTTGTCAGACCGGCCTGAGGCTACCTTCA
GAGCTCGGCTGGATTTAGGCATCCCAGGTGATGTGCCCAAATATGACATAATATTTGTTAAT
GTGAGGACCCCATATAAATACCATCACTATCAGCAGTGTGAAGACCATGCCATTAAGCTTAG
CATGTTGACCAAGAAAGCTTGTCTGCATCTGAATCCCGGCGGAACCTGTGTCAGCATAGGTT
ATGGTTACGCTGACAGGGCCAGCGAAAGCATCATTGGTGCTATAGCGCGGCAGTTCAAGTTT
TCCCGGGTATGCAAACCGAAATCCTCACTTGAAGAGACGGAAGTTCTGTTTGTATTCATTGG
GTACGATCGCAAGGCCCGTACGCACAATCCTTACAAGCTTTCATCAACCTTGACCAACATTT
ATACAGGTTCCAGACTCCACGAAGCCGGATG
```

FIG. 2C

```
TGCACCCTCATATCATGTGGTGCGAGGGGATATTGCCACGGCCACCGAAGGAGTGATTATAA
ATGCTGCTAACAGCAAAGGACAACCTGGCGGAGGGGTGTGCGGAGCGCTGTATAAGAAATTC
CCGGAAAGCTTCGATTTACAGCCGATCGAAGTAGGAAAAGCGCGACTGGTCAAAGGTGCAGC
TAAACATATCATTCATGCCGTAGGACCAAACTTCAACAAAGTTTCGGAGGTTGAAGGTGACA
AACAGTTGGCAGAGGCTTATGAGTCCATCGCTAAGATTGTCAACGATAACAATTACAAGTCA
GTAGCGATTCCACTGTTGTCCACCGGCATCTTTTCCGGGAACAAAGATCGACTAACCCAATC
ATTGAACCATTTGCTGACAGCTTTAGACACCACTGATGCAGATGTAGCCATATACTGCAGGG
ACAAGAAATGGGAAATGACTCTCAAGGAAGCAGTGGCTAGGAGAGAAGCAGTGGAGGAGATA
TGCATATCCGACGACTCTTCAGTGACAGAACCTGATGCAGAGCTGGTGAGGGTGCATCCGAA
GAGTTCTTTGGCTGGAAGGAAGGGCTACAGCACAAGCGATGGCAAAACTTTCTCATATTTGG
AAGGGACCAAGTTTCACCAGGCGGCCAAGGATATAGCAGAAATTAATGCCATGTGGCCCGTT
GCAACGGAGGCCAATGAGCAGGTATGCATGTATATCCTCGGAGAAAGCATGAGCAGTATTAG
GTCGAAATGCCCCGTCGAAGAGTCGGAAGCCTCCACACCACCTAGCACGCTGCCTTGCTTGT
GCATCCATGCCATGACTCCAGAAAGAGTACAGCGCCTAAAAGCCTCACGTCCAGAACAAATT
ACTGTGTGCTCATCCTTTCCATTGCCGAAGTATAGAATCACTGGTGTGCAGAAGATCCAATG
CTCCCAGCCTATATTGTTCTCACCGAAAGTGCCTGCGTATATTCATCCAAGGAAGTATCTCG
TGGAAACACCACCGGTAGACGAGACTCCGGAGCCATCGGCAGAGAACCAATCCACAGAGGGG
ACACCTGAACAACCACCACTTATAACCGAGGATGAGACCAGGACTAGAACGCCTGAGCCGAT
CATCATCGAAGAGGAAGAAGAGGATAGCATAAGTTTGCTGTCAGATGGCCCGACCCACCAGG
TGCTGCAAGTCGAGGCAGACATTCACGGGCCGCCCTCTGTATCTAGCTCATCCTGGTCCATT
CCTCATGCATCCGACTTTGATGTGGACAGTTTATCCATACTTGACACCCTGGAGGGAGCTAG
CGTGACCAGCGGGCAACGTCAGCCGAGACTAACTCTTACTTCGCAAAGAGTATGGAGTTTC
TGGCGCGACCGGTGCCTGCGCCTCGAACAGTATTCAGGAACCCTCCACATCCCGCTCCGCGC
ACAAGAACACCGTCACTTGCACCCAGCAGGGCCTGCTCGAGAACCAGCCTAGTTTCCACCCC
GCCAGGCGTGAATAGGGTGATCACTAGAGAGGAGCTCGAGGCGCTTACCCCGTCACGCACTC
CTAGCAGGTCGGTCTCGAGAACCAGCCTGGTCTCCAACCCGCCAGGCGTAAATAGGGTGATT
ACAAGAGAGGAGTTTGAGGCGTTCGTAGCACAACAACAATGACGGTTTGATGCGGGTGCATA
CATCTTTTCCTCCGACACCGGTCAAGGGCATTTACAACAAAAATCAGTAAGGCAAACGGTGC
TATCCGAAGTGGTGTTGGAGAGGACCGAATTGGAGATTTCGTATGCCCCGCGCCTCGACCAA
GAAAAAGAAGAATTACTACGCAAGAAATTACAGTTAAATCCCACACCTGCTAACAGAAGCAG
ATACCAGTCCAGGAAGGTGGAGAACATGAAAGCCATAACAGCTAGACGTATTCTGCAAGGCC
TAGGGCATTATTTGAAGGCAGAAGGAAAAGTGGAGTGCTACCGAACCCTGCATCCTGTTCCT
TTGTATTCATCTAGTGTGAACCGTGCCTTTTCAAGCCCCAAGGTCGCAGTGGAAGCCTGTAA
CGCCATGTTGAAAGAGAACTTTCCGACTGTGGCT
```

FIG. 2D

TCTTACTGTATTATTCCAGAGTACGATGCCTATTTGGACATGGTTGACGGAGCTTCATGCTG
CTTAGACACTGCCAGTTTTTGCCCTGCAAAGCTGCGCAGCTTTCCAAAGAAACACTCCTATT
TGGAACCCACAATACGATCGGCAGTGCCTTCAGCGATCCAGAACACGCTCCAGAACGTCCTG
GCAGCTGCCACAAAAAGAAATTGCAATGTCACGCAAATGAGAGAATTGCCCGTATTGGATTC
GGCGGCCTTTAATGTGGAATGCTTCAAGAAATATGCGTGTAATAATGAATATTGGGAAACGT
TTAAAGAAAACCCCATCAGGCTTACTGAAGAAACGTGGTAAATTACATTACCAAATTAAAA
GGACCAAAAGCTGCTGCTCTTTTTGCGAAGACACATAATTTGAATATGTTGCAGGACATACC
AATGGACAGGTTTGTAATGGACTTAAAGAGAGACGTGAAAGTGACTCCAGGAACAAAACATA
CTGAAGAACGGCCCAAGGTACAGGTGATCCAGGCTGCCGATCCGCTAGCAACAGCGTATCTG
TGCGGAATCCACCGAGAGCTGGTTAGGAGATTAAATGCGGTCCTGCTTCCGAACATTCATAC
ACTGTTTGATATGTCGGCTGAAGACTTTGACGCTATTATAGCCGAGCACTTCCAGCCTGGGG
ATTGTGTTCTGGAAACTGACATCGCGTCGTTTGATAAAAGTGAGGACGACGCCATGGCTCTG
ACCGCGTTAATGATTCTGGAAGACTTAGGTGTGGACGCAGAGCTGTTGACGCTGATTGAGGC
GGCTTTCGGCGAAATTTCATCAATACATTTGCCCACTAAAACTAAATTTAAATTCGGAGCCA
TGATGAAATCTGGAATGTTCCTCACACTGTTTGTGAACACAGTCATTAACATTGTAATCGCA
AGCAGAGTGTTGAGAGAACGGCTAACCGGATCACCATGTGCAGCATTCATTGGAGATGACAA
TATCGTGAAAGGAGTCAAATCGGACAAATTAATGGCAGACAGGTGCGCCACCTGGTTGAATA
TGGAAGTCAAGATTATAGATGCTGTGGTGGGCGAGAAAGCGCCTTATTTCTGTGGAGGGTTT
ATTTTGTGTGACTCCGTGACCGGCACAGCGTGCCGTGTGGCAGACCCCCTAAAAAGGCTGTT
TAAGCTTGGCAAACCTCTGGCAGCAGACGATGAACATGATGATGACAGGAGAAGGGCATTGC
ATGAAGAGTCAACACGCTGGAACCGAGTGGGTATTCTTTCAGAGCTGTGCAAGGCAGTAGAA
TCAAGGTATGAAACCGTAGGAACTTCCATCATAGTTATGGCCATGACTACTCTAGCTAGCAG
TGTTAAATCATTCAGCTACCTGAGAGGGGCCCCTATAACTCTCTACGGCTAACCTGAATGGA
CTACGACATAGTCTAGTCGACGCCACCATGCTGCTGCTGCTGCTGCTGCTGGGCCTGAGGCT
ACAGCTCTCCCTGGGCATCATCCCAGTTGAGGAGGAGAACCCGGACTTCTGGAACCGCGAGG
CAGCCGAGGCCCTGGGTGCCGCCAAGAAGCTGCAGCCTGCACAGACAGCCGCCAAGAACCTC
ATCATCTTCCTGGGCGATGGGATGGGGGTGTCTACGGTGACAGCTGCCAGGATCCTAAAAGG
GCAGAAGAAGGACAAACTGGGGCCTGAGATACCCCTGGCCATGGACCGCTTCCCATATGTGG
CTCTGTCCAAGACATACAATGTAGACAAACATGTGCCAGACAGTGGAGCCACAGCCACGGCC
TACCTGTGCGGGGTCAAGGGCAACTTCCAGACCATTGGCTTGAGTGCAGCCGCCCGCTTTAA
CCAGTGCAACACGACACGCGGCAACGAGGTCATCTCCGTGATGAATCGGGCCAAGAAAGCAG
GGAAGTCAGTGGGAGTGGTAACCACCACACGAGTGCAGCACGCCTCGCCAGCCGGCACCTAC
GCCCACACGGTGAACCGCAACTGGTACTCGGACGCCGACGTGCCTGCCTCGGCCCGCCAGGA
GGGGTGCCAGGACATCGCTACGCAGCTCATCTCC

FIG. 2E

```
AACATGGACATTGACGTGATCCTAGGTGGAGGCCGAAAGTACATGTTTCGCATGGGAACCCC
AGACCCTGAGTACCCAGATGACTACAGCCAAGGTGGGACCAGGCTGGACGGGAAGAATCTGG
TGCAGGAATGGCTGGCGAAGCGCCAGGGTGCCCGGTATGTGTGGAACCGCACTGAGCTCATG
CAGGCTTCCCTGGACCCGTCTGTGACCCATCTCATGGGTCTCTTTGAGCCTGGAGACATGAA
ATACGAGATCCACCGAGACTCCACACTGGACCCCTCCCTGATGGAGATGACAGAGGCTGCCC
TGCGCCTGCTGAGCAGGAACCCCCGCGGCTTCTTCCTCTTCGTGGAGGGTGGTCGCATCGAC
CATGGTCATCATGAAAGCAGGGCTTACCGGGCACTGACTGAGACGATCATGTTCGACGACGC
CATTGAGAGGGCGGGCCAGCTCACCAGCGAGGAGGACACGCTGAGCCTCGTCACTGCCGACC
ACTCCCACGTCTTCTCCTTCGGAGGCTACCCCCTGCGAGGGAGCTCCATCTTCGGGCTGGCC
CCTGGCAAGGCCCGGGACAGGAAGGCCTACACGGTCCTCCTATACGGAAACGGTCCAGGCTA
TGTGCTCAAGGACGGCGCCCGGCCGGATGTTACCGAGAGCGAGAGCGGGAGCCCCGAGTATC
GGCAGCAGTCAGCAGTGCCCCTGGACGAAGAGACCCACGCAGGCGAGGACGTGGCGGTGTTC
GCGCGCGGCCCGCAGGCGCACCTGGTTCACGGCGTGCAGGAGCAGACCTTCATAGCGCACGT
CATGGCCTTCGCCGCCTGCCTGGAGCCCTACACCGCCTGCGACCTGGCGCCCCCCGCCGGCA
CCACCGACGCCGCGCACCCGGGTTACTCTAGAGTCGGGGCGGCCGGCCGCTTCGAGCAGACA
TGAACTAGACGGCGCGCCCACCCAGCGGCCGCATACAGCAGCAATTGGCAAGCTGCTTACAT
AGAACTCGCGGCGATTGGCATGCCGCCTTAAAATTTTATTTTATTTTTCTTTTCTTTTCCG
AATCGGATTTTGTTTTTAATATTTCAAAAAAAAAAAAAAAAAAAAAAAAAAAAAAAAAAAA
AAAGGGTCGGCATGGCATCTCCACCTCCTCGCGGTCCGACCTGGGCATCCGAAGGAGGACGC
ACGTCCACTCGGATGGCTAAGGGAGAGCCACGTTTAAACCAGCTCCAATTCGCCCTATAGTG
AGTCGTATTACGCGCGCTCACTGGCCGTCGTTTTACAACGTCGTGACTGGGAAAACCCTGGC
GTTACCCAACTTAATCGCCTTGCAGCACATCCCCCTTTCGCCAGCTGGCGTAATAGCGAAGA
GGCCCGCACCGATCGCCCTTCCCAACAGTTGCGCAGCCTGAATGGCGAATGGGACGCGCCCT
GTAGCGGCGCATTAAGCGCGGCGGGTGTGGTGGTTACGCGCAGCGTGACCGCTACACTTGCC
AGCGCCCTAGCGCCCGCTCCTTTCGCTTTCTTCCCTTCCTTTCTCGCCACGTTCGCCGGCTT
TCCCCGTCAAGCTCTAAATCGGGGGCTCCCTTTAGGGTTCCGATTTAGTGCTTTACGGCACC
TCGACCCCAAAAAACTTGATTAGGGTGATGGTTCACGTAGTGGGCCATCGCCCTGATAGACG
GTTTTTCGCCCTTTGACGTTGGAGTCCACGTTCTTTAATAGTGGACTCTTGTTCCAAACTGG
AACAACACTCAACCCTATCTCGGTCTATTCTTTTGATTTATAAGGGATTTTGCCGATTTCGG
CCTATTGGTTAAAAAATGAGCTGATTTAACAAAAATTTAACGCGAATTTTAACAAAATATTA
ACGCTTACAATTTAGGTGGCACTTTTCGGGGAAATGTGCGCGGAACCCCTATTTGTTTATTT
TTCTAAATACATTCAAATATGTATCCGCTCATGAGACAATAACCCTGATAAATGCTTCAATA
ATATTGAAAAGGAAGAGTATGAGTATTCAACATTTCCGTGTCGCCCTTATTCCCTTTTTTG
CGGCATTTTGCCTTCCTGTTTTTGCTCACCCAGA
```

FIG. 2F

AACGCTGGTGAAAGTAAAAGATGCTGAAGATCAGTTGGGTGCACGAGTGGGTTACATCGAAC
TGGATCTCAACAGCGGTAAGATCCTTGAGAGTTTTCGCCCCGAAGAACGTTTTCCAATGATG
AGCACTTTTAAAGTTCTGCTATGTGGCGCGGTATTATCCCGTATTGACGCCGGGCAAGAGCA
ACTCGGTCGCCGCATACACTATTCTCAGAATGACTTGGTTGAGTACTCACCAGTCACAGAAA
AGCATCTTACGGATGGCATGACAGTAAGAGAATTATGCAGTGCTGCCATAACCATGAGTGAT
AACACTGCGGCCAACTTACTTCTGACAACGATCGGAGGACCGAAGGAGCTAACCGCTTTTTT
GCACAACATGGGGGATCATGTAACTCGCCTTGATCGTTGGGAACCGGAGCTGAATGAAGCCA
TACCAAACGACGAGCGTGACACCACGATGCCTGTAGCAATGGCAACAACGTTGCGCAAACTA
TTAACTGGCGAACTACTTACTCTAGCTTCCCGGCAACAATTAATAGACTGGATGGAGGCGGA
TAAAGTTGCAGGACCACTTCTGCGCTCGGCCCTTCCGGCTGGCTGGTTTATTGCTGATAAAT
CTGGAGCCGGTGAGCGTGGGTCTCGCGGTATCATTGCAGCACTGGGGCCAGATGGTAAGCCC
TCCCGTATCGTAGTTATCTACACGACGGGGAGTCAGGCAACTATGGATGAACGAAATAGACA
GATCGCTGAGATAGGTGCCTCACTGATTAAGCATTGGTAACTGTCAGACCAAGTTTACTCAT
ATATACTTTAGATTGATTTAAAACTTCATTTTTAATTTAAAAGGATCTAGGTGAAGATCCTT
TTTGATAATCTCATGACCAAAATCCCTTAACGTGAGTTTTCGTTCCACTGAGCGTCAGACCC
CGTAGAAAAGATCAAAGGATCTTCTTGAGATCCTTTTTTTCTGCGCGTAATCTGCTGCTTGC
AAACAAAAAAACCACCGCTACCAGCGGTGGTTTGTTTGCCGGATCAAGAGCTACCAACTCTT
TTTCCGAAGGTAACTGGCTTCAGCAGAGCGCAGATACCAAATACTGTCCTTCTAGTGTAGCC
GTAGTTAGGCCACCACTTCAAGAACTCTGTAGCACCGCCTACATACCTCGCTCTGCTAATCC
TGTTACCAGTGGCTGCTGCCAGTGGCGATAAGTCGTGTCTTACCGGGTTGGACTCAAGACGA
TAGTTACCGGATAAGGCGCAGCGGTCGGGCTGAACGGGGGGTTCGTGCACACAGCCCAGCTT
GGAGCGAACGACCTACACCGAACTGAGATACCTACAGCGTGAGCTATGAGAAAGCGCCACGC
TTCCCGAAGGGAGAAAGGCGGACAGGTATCCGGTAAGCGGCAGGGTCGGAACAGGAGAGCGC
ACGAGGGAGCTTCCAGGGGGAAACGCCTGGTATCTTTATAGTCCTGTCGGGTTTCGCCACCT
CTGACTTGAGCGTCGATTTTTGTGATGCTCGTCAGGGGGCGGAGCCTATGGAAAAACGCCA
GCAACGCGGCCTTTTTACGGTTCCTGGCCTTTTGCTGGCCTTTTGCTCACATGTTCTTTCCT
GCGTTATCCCCTGATTCTGTGGATAACCGTATTACCGCCTTTGAGTGAGCTGATACCGCTCG
CCGCAGCCGAACGACCGAGCGCAGCGAGTCAGTGAGCGAGGAAGCGGAAGAGCGCCCAATAC
GCAAACCGCCTCTCCCCGCGCGTTGGCCGATTCATTAATGCAGCTGGCACGACAGGTTTCCC
GACTGGAAAGCGGGCAGTGAGCGCAACGCAATTAATGTGAGTTAGCTCACTCATTAGGCACC
CCAGGCTTTACACTTTATGCTTCCGGCTCGTATGTTGTGTGGAATTGTGAGCGGATAACAAT
TTCACACAGGAAACAGCTATGACCATGATTACGCCAAGCGCGCAATTAACCCTCACTAAAGG
GAACAAAAGCTGGGTACCGGGCCCACGCGTAATACGACTCACTATAG

FIG. 3A

```
ATGGGCGGCGCATGAGAGAAGCCCAGACCAATTACCTACCCAAAATGGAGAAAGTTCACGTT
GACATCGAGGAAGACAGCCCATTCCTCAGAGCTTTGCAGCGGAGCTTCCCGCAGTTTGAGGT
AGAAGCCAAGCAGGTCACTGATAATGACCATGCTAATGCCAGAGCGTTTTCGCATCTGGCTT
CAAAACTGATCGAAACGGAGGTGGACCCATCCGACACGATCCTTGACATTGGAAGTGCGCCC
GCCCGCAGAATGTATTCTAAGCACAAGTATCATTGTATCTGTCCGATGAGATGTGCGGAAGA
TCCGGACAGATTGTATAAGTATGCAACTAAGCTGAAGAAAACTGTAAGGAAATAACTGATA
AGGAATTGGACAAGAAAATGAAGGAGCTCGCCGCCGTCATGAGCGACCCTGACCTGGAAACT
GAGACTATGTGCCTCCACGACGACGAGTCGTGTCGCTACGAAGGGCAAGTCGCTGTTTACCA
GGATGTATACGCGGTTGACGGACCGACAAGTCTCTATCACCAAGCCAATAAGGGAGTTAGAG
TCGCCTACTGGATAGGCTTTGACACCACCCCTTTTATGTTTAAGAACTTGGCTGGAGCATAT
CCATCATACTCTACCAACTGGGCCGACGAAACCGTGTTAACGGCTCGTAACATAGGCCTATG
CAGCTCTGACGTTATGGAGCGGTCACGTAGAGGGATGTCCATTCTTAGAAAGAAGTATTTGA
AACCATCCAACAATGTTCTATTCTCTGTTGGCTCGACCATCTACCACGAGAAGAGGGACTTA
CTGAGGAGCTGGCACCTGCCGTCTGTATTTCACTTACGTGGCAAGCAAAATTACACATGTCG
GTGTGAGACTATAGTTAGTTGCGACGGGTACGTCGTTAAAAGAATAGCTATCAGTCCAGGCC
TGTATGGGAAGCCTTCAGGCTATGCTGCTACGATGCACCGCGAGGGATTCTTGTGCTGCAAA
GTGACAGACACATTGAACGGGGAGAGGGTCTCTTTTCCCGTGTGCACGTATGTGCCAGCTAC
ATTGTGTGACCAAATGACTGGCATACTGGCAACAGATGTCAGTGCGGACGACGCGCAAAAAC
TGCTGGTTGGGCTCAACCAGCGTATAGTCGTCAACGGTCGCACCCAGAGAAACACCAATACC
ATGAAAAATTACCTTTTGCCCGTAGTGGCCCAGGCATTTGCTAGGTGGGCAAAGGAATATAA
GGAAGATCAAGAAGATGAAAGGCCACTAGGACTACGAGATAGACAGTTAGTCATGGGGTGTT
GTTGGGCTTTTAGAAGGCACAAGATAACATCTATTTATAAGCGCCCGGATACCCAAACCATC
ATCAAAGTGAACAGCGATTTCCACTCATTCGTGCTGCCCAGGATAGGCAGTAACACATTGGA
GATCGGGCTGAGAACAAGAATCAGGAAAATGTTAGAGGAGCACAAGGAGCCGTCACCTCTCA
TTACCGCCGAGGACGTACAAGAAGCTAAGTGCGCAGCCGATGAGGCTAAGGAGGTGCGTGAA
GCCGAGGAGTTGCGCGCAGCTCTACCACCTTTGGCAGCTGATGTTGAGGAGCCCACTCTGGA
AGCCGATGTCGACTTGATGTTACAAGAGGCTGGGGCCGGCTCAGTGGAGACACCTCGTGGCT
TGATAAAGGTTACCAGCTACGCTGGCGAGGACAAGATCGGCTCTTACGCTGTGCTTTCTCCG
CAGGCTGTACTCAAGAGTGAAAAATTATCTTGCATCCACCCTCTCGCTGAACAAGTCATAGT
GATAACACACTCTGGCCGAAAAGGGCGTTATGCCGTGGAACCATACCATGGTAAAGTAGTGG
TGCCAGAGGGACATGCAATACCCGTCCAGGACTTTCAAGCTCTGAGTGAAAGTGCCACCATT
GTGTACAACGAACGTGAGTTCGTAAACAGGTACCTGCACCATATTGCCACACATGGAGGAGC
GCTGAACACTGATGAAGAATATTACAAAACT
```

FIG. 3B

```
GTCAAGCCCAGCGAGCACGACGGCGAATACCTGTACGACATCGACAGGAAACAGTGCGTCAA
GAAAGAACTAGTCACTGGGCTAGGGCTCACAGGCGAGCTGGTGGATCCTCCCTTCCATGAAT
TCGCCTACGAGAGTCTGAGAACACGACCAGCCGCTCCTTACCAAGTACCAACCATAGGGGTG
TATGGCGTGCCAGGATCAGGCAAGTCTGGCATCATTAAAAGCGCAGTCACCAAAAAAGATCT
AGTGGTGAGCGCCAAGAAAGAAAACTGTGCAGAATTATAAGGGACGTCAAGAAAATGAAAG
GGCTGGACGTCAATGCCAGAACTGTGGACTCAGTGCTCTTGAATGGATGCAAACACCCCGTA
GAGACCCTGTATATTGACGAAGCTTTTGCTTGTCATGCAGGTACTCTCAGAGCGCTCATAGC
CATTATAAGACCTAAAAAGGCAGTGCTCTGCGGGGATCCCAAACAGTGCGGTTTTTTTAACA
TGATGTGCCTGAAAGTGCATTTTAACCACGAGATTTGCACACAAGTCTTCCACAAAAGCATC
TCTCGCCGTTGCACTAAATCTGTGACTTCGGTCGTCTCAACCTTGTTTTACGACAAAAAAAT
GAGAACGACGAATCCGAAAGAGACTAAGATTGTGATTGACACTACCGGCAGTACCAAACCTA
AGCAGGACGATCTCATTCTCACTTGTTTCAGAGGGTGGGTGAAGCAGTTGCAAATAGATTAC
AAAGGCAACGAAATAATGACGGCAGCTGCCTCTCAAGGGCTGACCCGTAAAGGTGTGTATGC
CGTTCGGTACAAGGTGAATGAAAATCCTCTGTACGCACCCACCTCAGAACATGTGAACGTCC
TACTGACCCGCACGGAGGACCGCATCGTGTGGAAAACACTAGCCGGCGACCCATGGATAAAA
ACACTGACTGCCAAGTACCCTGGGAATTTCACTGCCACGATAGAGGAGTGGCAAGCAGAGCA
TGATGCCATCATGAGGCACATCTTGGAGAGACCGGACCCTACCGACGTCTTCCAGAATAAGG
CAAACGTGTGTTGGGCCAAGGCTTTAGTGCCGGTGCTGAAGACCGCTGGCATAGACATGACC
ACTGAACAATGGAACACTGTGGATTATTTTGAAACGGACAAAGCTCACTCAGCAGAGATAGT
ATTGAACCAACTATGCGTGAGGTTCTTTGGACTCGATCTGGACTCCGGTCTATTTTCTGCAC
CCACTGTTCCGTTATCCATTAGGAATAATCACTGGGATAACTCCCCGTCGCCTAACATGTAC
GGGCTGAATAAAGAAGTGGTCCGTCAGCTCTCTCGCAGGTACCCACAACTGCCTCGGGCAGT
TGCCACTGGAAGAGTCTATGACATGAACACTGGTACACTGCGCAATTATGATCCGCGCATAA
ACCTAGTACCTGTAAACAGAAGACTGCCTCATGCTTTAGTCCTCCACCATAATGAACACCCA
CAGAGTGACTTTTCTTCATTCGTCAGCAAATTGAAGGGCAGAACTGTCCTGGTGGTCGGGGA
AAAGTTGTCCGTCCCAGGCAAAATGGTTGACTGGTTGTCAGACCGGCCTGAGGCTACCTTCA
GAGCTCGGCTGGATTTAGGCATCCCAGGTGATGTGCCCAAATATGACATAATATTTGTTAAT
GTGAGGACCCCATATAAATACCATCACTATCAGCAGTGTGAAGACCATGCCATTAAGCTTAG
CATGTTGACCAAGAAAGCTTGTCTGCATCTGAATCCCGGCGGAACCTGTGTCAGCATAGGTT
ATGGTTACGCTGACAGGGCCAGCGAAAGCATCATTGGTGCTATAGCGCGGCAGTTCAAGTTT
TCCCGGGTATGCAAACCGAAATCCTCACTTGAAGAGACGGAAGTTCTGTTTGTATTCATTGG
GTACGATCGCAAGGCCCGTACGCACAATCCTTACAAGCTTTCATCAACCTTGACCAACATTT
ATACAGGTTCCAGACTCCACGAAGCCGGATGTGCACCCTCATATCATGTGGTGCGAGGGGAT
ATTGCCACGGCCACCGAAGGAGTGATTATAAATG
```

FIG. 3C

```
CTGCTAACAGCAAAGGACAACCTGGCGGAGGGGTGTGCGGAGCGCTGTATAAGAAATTCCCG
GAAAGCTTCGATTTACAGCCGATCGAAGTAGGAAAAGCGCGACTGGTCAAAGGTGCAGCTAA
ACATATCATTCATGCCGTAGGACCAAACTTCAACAAAGTTTCGGAGGTTGAAGGTGACAAAC
AGTTGGCAGAGGCTTATGAGTCCATCGCTAAGATTGTCAACGATAACAATTACAAGTCAGTA
GCGATTCCACTGTTGTCCACCGGCATCTTTTCCGGGAACAAAGATCGACTAACCCAATCATT
GAACCATTTGCTGACAGCTTTAGACACCACTGATGCAGATGTAGCCATATACTGCAGGGACA
AGAAATGGGAAATGACTCTCAAGGAAGCAGTGGCTAGGAGAGAAGCAGTGGAGGAGATATGC
ATATCCGACGACTCTTCAGTGACAGAACCTGATGCAGAGCTGGTGAGGGTGCATCCGAAGAG
TTCTTTGGCTGGAAGGAAGGGCTACAGCACAAGCGATGGCAAAACTTTCTCATATTTGGAAG
GGACCAAGTTTCACCAGGCGGCCAAGGATATAGCAGAAATTAATGCCATGTGGCCCGTTGCA
ACGGAGGCCAATGAGCAGGTATGCATGTATATCCTCGGAGAAAGCATGAGCAGTATTAGGTC
GAAATGCCCCGTCGAAGAGTCGGAAGCCTCCTCACCACCTAGCACGCTGCCTTGCTTGTGCA
TCCATGCCATGACTCCAGAAAGAGTACAGCGCCTAAAAGCCTCACGTCCAGAACAAATTACT
GTGTGCTCATCCTTTCCATTGCCGAAGTATAGAATCACTGGTGTGCAGAAGATCCAATGCTC
CCAGCCTATATTGTTCTCACCGAAAGTGCCTGCGTATATTCATCCAAGGAAGTATCTCGTGG
AAACACCACCGGTAGACGAGACTCCGGAGCCATCGGCAGAGAACCAATCCACAGAGGGGACA
CCTGAACAACCACCACTTATAACCGAGGATGAGACCAGGACTAGAACGCCTGAGCCGATCAT
CATCGAAGAGGAAGAAGAGGATAGCATAAGTTTGCTGTCAGATGGCCCGACCCACCAGGTGC
TGCAAGTCGAGGCAGACATTCACGGGCCGCCCTCTGTATCTAGCTCATCCTGGTCCATTCCT
CATGCATCCGACTTTGATGTGGACAGTTTATCCATACTTGACACCCTGGAGGGAGCTAGCGT
GACCAGCGGGGCAACGTCAGCCGAGACTAACTCTTACTTCGCAAAGAGTATGGAGTTTCTGG
CGCGACCGGTGCCTGCGCCTCGAACAGTATTCAGGAACCCTCCACATCCCGCTCCGCGCACA
AGAACACCGTCACTTGCACCCAGCAGGGCCTGCTCGAGAGGGATCACGGGAGAAACCGTGGG
ATACGCGGTTACACACAATAGCGAGGGCTTCTTGCTATGCAAAGTTACTGACACAGTAAAAG
GAGAACGGGTATCGTTCCCTGTGTGCACGTACATCCCGGCCACCATAAACTCGAGAACCAGC
CTGGTCTCCAACCCGCCAGGCGTAAATAGGGTGATTACAAGAGAGGAGTTTGAGGCGTTCGT
AGCACAACAACAATGACGGTTTGATGCGGGTGCATACATCTTTTCCTCCGACACCGGTCAAG
GGCATTTACAACAAAAATCAGTAAGGCAAACGGTGCTATCCGAAGTGGTGTTGGAGAGGACC
GAATTGGAGATTTCGTATGCCCCGCGCCTCGACCAAGAAAAGAAGAATTACTACGCAAGAA
ATTACAGTTAAATCCCACACCTGCTAACAGAAGCAGATACCAGTCCAGGAAGGTGGAGAACA
TGAAAGCCATAACAGCTAGACGTATTCTGCAAGGCCTAGGGCATTATTTGAAGGCAGAAGGA
AAAGTGGAGTGCTACCGAACCCTGCATCCTGTTCCTTTGTATTCATCTAGTGTGAACCGTGC
CTTTTCAAGCCCCAAGGTCGCAGTGGAAGCCTGTAACGCCATGTTGAAAGAGAACTTTCCGA
CTGTGGCTTCTTACTGTATTATTCCAGAGTACGA
```

FIG. 3D

```
TGCCTATTTGGACATGGTTGACGGAGCTTCATGCTGCTTAGACACTGCCAGTTTTTGCCCTG
CAAAGCTGCGCAGCTTTCCAAAGAAACACTCCTATTTGGAACCCACAATACGATCGGCAGTG
CCTTCAGCGATCCAGAACACGCTCCAGAACGTCCTGGCAGCTGCCACAAAAAGAAATTGCAA
TGTCACGCAAATGAGAGAATTGCCCGTATTGGATTCGGCGGCCTTTAATGTGGAATGCTTCA
AGAAATATGCGTGTAATAATGAATATTGGGAAACGTTTAAAGAAAACCCCATCAGGCTTACT
GAAGAAAACGTGGTAAATTACATTACCAAATTAAAAGGACCAAAAGCTGCTGCTCTTTTTGC
GAAGACACATAATTTGAATATGTTGCAGGACATACCAATGGACAGGTTTGTAATGGACTTAA
AGAGAGACGTGAAAGTGACTCCAGGAACAAAACATACTGAAGAACGGCCCAAGGTACAGGTG
ATCCAGGCTGCCGATCCGCTAGCAACAGCGTATCTGTGCGGAATCCACCGAGAGCTGGTTAG
GAGATTAAATGCGGTCCTGCTTCCGAACATTCATACACTGTTTGATATGTCGGCTGAAGACT
TTGACGCTATTATAGCCGAGCACTTCCAGCCTGGGGATTGTGTTCTGGAAACTGACATCGCG
TCGTTTGATAAAAGTGAGGACGACGCCATGGCTCTGACCGCGTTAATGATTCTGGAAGACTT
AGGTGTGGACGCAGAGCTGTTGACGCTGATTGAGGCGGCTTTCGGCGAAATTTCATCAATAC
ATTTGCCCACTAAAACTAAATTTAAATTCGGAGCCATGATGAAATCTGGAATGTTCCTCACA
CTGTTTGTGAACACAGTCATTAACATTGTAATCGCAAGCAGAGTGTTGAGAGAACGGCTAAC
CGGATCACCATGTGCAGCATTCATTGGAGATGACAATATCGTGAAAGGAGTCAAATCGGACA
AATTAATGGCAGACAGGTGCGCCACCTGGTTGAATATGGAAGTCAAGATTATAGATGCTGTG
GTGGGCGAGAAAGCGCCTTATTTCTGTGGAGGGTTTATTTTGTGTGACTCCGTGACCGGCAC
AGCGTGCCGTGTGGCAGACCCCCTAAAAAGGCTGTTTAAGCTTGGCAAACCTCTGGCAGCAG
ACGATGAACATGATGATGACAGGAGAAGGGCATTGCATGAAGAGTCAACACGCTGGAACCGA
GTGGGTATTCTTTCAGAGCTGTGCAAGGCAGTAGAATCAAGGTATGAAACCGTAGGAACTTC
CATCATAGTTATGGCCATGACTACTCTAGCTAGCAGTGTTAAATCATTCAGCTACCTGAGAG
GGGCCCCTATAACTCTCTACGGCTAACCTGAATGGACTACGACATAGTCTAGTCCGCCAAGC
CTCAGCGTCGACGCCACCATGGAACTGCTGATCCTGAAGGCCAACGCCATCACCACCATCCT
GACCGCCGTGACCTTCTGCTTCGCCAGCGGCCAGAACATCACCGAGGAATTCTACCAGAGCA
CCTGCAGCGCCGTGAGCAAGGGCTACCTGAGCGCCCTGCGGACCGGCTGGTACACCAGCGTG
ATCACCATCGAGCTGTCCAACATCAAAGAAAACAAGTGCAACGGCACCGACGCCAAGGTGAA
ACTGATCAAGCAGGAACTGGACAAGTACAAGAACGCCGTGACCGAGCTGCAGCTGCTGATGC
AGAGCACCCCCGCCACCAACAACCGGGCCAGAAGAGAGCTGCCCCGGTTCATGAACTACACC
CTGAACAACGCCAAGAAAACCAACGTGACCCTGAGCAAGAAGCGGAAGCGGCGGTTCCTGGG
CTTCCTGCTGGGCGTGGGCAGCGCCATCGCCAGCGGGGTGGCCGTGTCCAAGGTGCTGCACC
TGGAAGGCGAGGTGAACAAGATCAAGTCCGCCCTGCTGTCCACCAACAAGGCCGTGGTGTCC
CTGAGCAACGGCGTGAGCGTGCTGACCAGCAAGGTGCTGGATCTGAAGAACTACATCGACAA
GCAGCTGCTGCCCATCGTGAACAAGCAGAGCTGC
```

FIG. 3E

```
AGCATCAGCAACATCGAGACCGTGATCGAGTTCCAGCAGAAGAACAACCGGCTGCTGGAAAT
CACCCGGGAGTTCAGCGTGAACGCCGGCGTGACCACCCCCGTGAGCACCTACATGCTGACCA
ACAGCGAGCTGCTGTCCCTGATCAATGACATGCCCATCACCAACGACCAGAAAAAGCTGATG
AGCAACAACGTGCAGATCGTGCGGCAGCAGAGCTACTCCATCATGAGCATCATCAAAGAAGA
GGTGCTGGCCTACGTGGTGCAGCTGCCCCTGTACGGCGTGATCGACACCCCTGCTGGAAGC
TGCACACCAGCCCCTGTGCACCACCAACACCAAGAGGGCAGCAACATCTGCCTGACCCGG
ACCGACCGGGCTGGTACTGCGACAACGCCGGCAGCGTGAGCTTCTTCCCCCAAGCCGAGAC
CTGCAAGGTGCAGAGCAACCGGGTGTTCTGCGACACCATGAACAGCCTGACCCTGCCCTCCG
AGGTGAACCTGTGCAACGTGGACATCTTCAACCCCAAGTACGACTGCAAGATCATGACCTCC
AAGACCGACGTGAGCAGCTCCGTGATCACCTCCCTGGGCGCCATCGTGAGCTGCTACGGCAA
GACCAAGTGCACCGCCAGCAACAAGAACCGGGGCATCATCAAGACCTTCAGCAACGGCTGCG
ACTACGTGAGCAACAAGGGCGTGGACACCGTGAGCGTGGGCAACACACTGTACTACGTGAAT
AAGCAGGAAGGCAAGAGCCTGTACGTGAAGGGCGAGCCCATCATCAACTTCTACGACCCCCT
GGTGTTCCCCAGCGACGAGTTCGACGCCAGCATCAGCCAGGTCAACGAGAAGATCAACCAGA
GCCTGGCCTTCATCCGGAAGAGCGACGAGCTGCTGCACAATGTGAATGCCGGCAAGAGCACC
ACCAATATCATGATCACCACAATCATCATCGTGATCATTGTGATCCTGCTGTCTCTGATTGC
CGTGGGCCTGCTGCTGTACTGCAAGGCCCGCAGCACCCCTGTGACCCTGTCCAAGGACCAGC
TGTCCGGCATCAACAATATCGCCTTCTCCAACTGAAGTCTAGAGCGGCCGCCGCTACGCCCC
AATGATCCGACCAGCAAAACTCGATGTACTTCGAGGAACTGATGTGCATAATGCATCAGGC
TGGTACATTAGATCCCCGCTTACCGCGGGCAATATAGCAACACTAAAAACTCGATGTACTTC
CGAGGAAGCGCAGTGCATAATGCTGCGCAGTGTTGCCACATAACCACTATATTAACCATTTA
TCTAGCGGACGCCAAAAACTCAATGTATTTCTGAGGAAGCGTGGTGCATAATGCCACGCAGC
GTCTGCATAACTTTTATTATTTCTTTTATTAATCAACAAAATTTTGTTTTTAACATTTCAAA
AAAAAAAAAAAAAAAAAAAAAAAAAAAAAAAAAAAAAGGGTCGGCATGGCATCTCCACCTCC
TCGCGGTCCGACCTGGGCATCCGAAGGAGGACGCACGTCCACTCGGATGGCTAAGGGAGAGC
CACGAGCTCCTGTTTAAACCAGCTCCAATTCGCCCTATAGTGAGTCGTATTACGCGCGCTCA
CTGGCCGTCGTTTTACAACGTCGTGACTGGGAAAACCCTGGCGTTACCCAACTTAATCGCCT
TGCAGCACATCCCCCTTTCGCCAGCTGGCGTAATAGCGAAGAGGCCCGCACCGATCGCCCTT
CCCAACAGTTGCGCAGCCTGAATGGCGAATGGGACGCGCCCTGTAGCGGCGCATTAAGCGCG
GCGGGTGTGGTGGTTACGCGCAGCGTGACCGCTACACTTGCCAGCGCCCTAGCGCCCGCTCC
TTTCGCTTTCTTCCCTTCCTTTCTCGCCACGTTCGCCGGCTTTCCCCGTCAAGCTCTAAATC
GGGGGCTCCCTTTAGGGTTCCGATTTAGTGCTTTACGGCACCTCGACCCCAAAAAACTTGAT
TAGGGTGATGGTTCACGTAGTGGGCCATCGCCCTGATAGACGGTTTTTCGCCCTTTGACGTT
GGAGTCCACGTTCTTTAATAGTGGACTCTTGTTC
```

FIG. 3F

```
CAAACTGGAACAACACTCAACCCTATCTCGGTCTATTCTTTTGATTTATAAGGGATTTTGCC
GATTTCGGCCTATTGGTTAAAAATGAGCTGATTTAACAAAAATTTAACGCGAATTTTAACA
AAATATTAACGCTTACAATTTAGGTGGCACTTTTCGGGGAAATGTGCGCGGAACCCCTATTT
GTTTATTTTTCTAAATACATTCAAATATGTATCCGCTCATGAGACAATAACCCTGATAAATG
CTTCAATAATATTGAAAAGGAAGAGTATGAGTATTCAACATTTCCGTGTCGCCCTTATTCC
CTTTTTTGCGGCATTTTGCCTTCCTGTTTTGCTCACCCAGAAACGCTGGTGAAAGTAAAAG
ATGCTGAAGATCAGTTGGGTGCACGAGTGGGTTACATCGAACTGGATCTCAACAGCGGTAAG
ATCCTTGAGAGTTTTCGCCCCGAAGAACGTTTTCCAATGATGAGCACTTTTAAAGTTCTGCT
ATGTGGCGCGGTATTATCCCGTATTGACGCCGGGCAAGAGCAACTCGGTCGCCGCATACACT
ATTCTCAGAATGACTTGGTTGAGTACTCACCAGTCACAGAAAAGCATCTTACGGATGGCATG
ACAGTAAGAGAATTATGCAGTGCTGCCATAACCATGAGTGATAACACTGCGGCCAACTTACT
TCTGACAACGATCGGAGGACCGAAGGAGCTAACCGCTTTTTTGCACAACATGGGGGATCATG
TAACTCGCCTTGATCGTTGGGAACCGGAGCTGAATGAAGCCATACCAAACGACGAGCGTGAC
ACCACGATGCCTGTAGCAATGGCAACAACGTTGCGCAAACTATTAACTGGCGAACTACTTAC
TCTAGCTTCCCGGCAACAATTAATAGACTGGATGGAGGCGGATAAAGTTGCAGGACCACTTC
TGCGCTCGGCCCTTCCGGCTGGCTGGTTTATTGCTGATAAATCTGGAGCCGGTGAGCGTGGG
TCTCGCGGTATCATTGCAGCACTGGGGCCAGATGGTAAGCCCTCCCGTATCGTAGTTATCTA
CACGACGGGGAGTCAGGCAACTATGGATGAACGAAATAGACAGATCGCTGAGATAGGTGCCT
CACTGATTAAGCATTGGTAACTGTCAGACCAAGTTTACTCATATATACTTTAGATTGATTTA
AAACTTCATTTTTAATTTAAAAGGATCTAGGTGAAGATCCTTTTTGATAATCTCATGACCAA
AATCCCTTAACGTGAGTTTTCGTTCCACTGAGCGTCAGACCCCGTAGAAAAGATCAAAGGAT
CTTCTTGAGATCCTTTTTTTCTGCGCGTAATCTGCTGCTTGCAAACAAAAAAACCACCGCTA
CCAGCGGTGGTTTGTTTGCCGGATCAAGAGCTACCAACTCTTTTTCCGAAGGTAACTGGCTT
CAGCAGAGCGCAGATACCAAATACTGTTCTTCTAGTGTAGCCGTAGTTAGGCCACCACTTCA
AGAACTCTGTAGCACCGCCTACATACCTCGCTCTGCTAATCCTGTTACCAGTGGCTGCTGCC
AGTGGCGATAAGTCGTGTCTTACCGGGTTGGACTCAAGACGATAGTTACCGGATAAGGCGCA
GCGGTCGGGCTGAACGGGGGGTTCGTGCACACAGCCCAGCTTGGAGCGAACGACCTACACCG
AACTGAGATACCTACAGCGTGAGCTATGAGAAAGCGCCACGCTTCCCGAAGGGAGAAAGGCG
GACAGGTATCCGGTAAGCGGCAGGGTCGGAACAGGAGAGCGCACGAGGGAGCTTCCAGGGGG
AAACGCCTGGTATCTTTATAGTCCTGTCGGGTTTCGCCACCTCTGACTTGAGCGTCGATTTT
TGTGATGCTCGTCAGGGGGCGGAGCCTATGGAAAAACGCCAGCAACGCGGCCTTTTTACGG
TTCCTGGCCTTTTGCTGGCCTTTTGCTCACATGTTCTTTCCTGCGTTATCCCCTGATTCTGT
GGATAACCGTATTACCGCCTTTGAGTGAGCTGATACCGCTCGCCGCAGCCGAACGACCGAGC
GCAGCGAGTCAGTGAGCGAGGAAGCGGAAGAGCG
```

FIG. 3G

CCCAATACGCAAACCGCCTCTCCCCGCGCGTTGGCCGATTCATTAATGCAGCTGGCACGACA
GGTTTCCCGACTGGAAAGCGGGCAGTGAGCGCAACGCAATTAATGTGAGTTAGCTCACTCAT
TAGGCACCCCAGGCTTTACACTTTATGCTCCCGGCTCGTATGTTGTGTGGAATTGTGAGCGG
ATAACAATTTCACACAGGAAACAGCTATGACCATGATTACGCCAAGCGCGCAATTAACCCTC
ACTAAAGGGAACAAAAGCTGGGTACCGGGCCCACGCGTCGGCTACAATTAATACATAACCTT
ATGTATCATACACATACGATTTAGGTGACACTATAG

1. Supernatant
2. RNA Desorbed
3. RNAse Stability

DELIVERY OF SELF-REPLICATING RNA USING BIODEGRADABLE POLYMER PARTICLES

RELATED APPLICATION

This application is the U.S. National Phase of International Application No. PCT/US2011/043086, filed Jul. 6, 2011 and published in English, which claims the benefit of U.S. Provisional Application No. 61/361,907, filed Jul. 6, 2010, the complete contents of which are hereby incorporated herein by reference for all purposes.

BACKGROUND

Particulate carriers have been used with adsorbed or entrapped antigens in attempts to elicit adequate immune responses. Such carriers present multiple copies of a selected antigen to the immune system and are believed to promote trapping and retention of antigens in local lymph nodes. The particles can be phagocytosed by macrophages and can enhance antigen presentation through cytokine release.

SUMMARY OF THE INVENTION

In one aspect, the present invention provides immunogenic compositions that comprise (a) positively charged particles comprising a biodegradable polymer and (b) an RNA replicon comprising at least one polynucleotide encoding at least one antigen adsorbed to the positively charged nanoparticles.

In certain embodiments, immunogenic compositions are provided which comprise: (a) positively charged particles that comprise a biodegradable polymer and a cationic surfactant; (b) an RNA replicon comprising at least one polynucleotide encoding at least one antigen adsorbed to the positively charged particles; and (c) a non-ionic surfactant.

In certain embodiments, immunogenic compositions are provided which comprise: (a) positively charged particles that comprise a biodegradable polymer and a cationic surfactant and (b) an RNA replicon comprising at least one polynucleotide encoding at least one antigen adsorbed to the positively charged particles, wherein the ratio of the number of moles of cationic nitrogen in the cationic surfactant to the number of moles of anionic phosphate in the RNA replicon (referred to herein as the N:P ratio) ranges from 100:1 to 1:100.

Immunogenic compositions in accordance with the invention may be lyophilized.

Particles in the immunogenic compositions of the invention include nanoparticles and microparticles. In certain embodiments, the immunogenic compositions of the invention comprising nanoparticles that have a D(v,0.5) value that is between 50 and 500 nanometers, a Z average value that is between 50 and 500 nanometers, or both. In certain other embodiments, the immunogenic compositions of the invention comprising microparticles that have a D(v,0.5) value that is between 500 and 5000 nanometers, a Z average value that is between 500 and 5000 nanometers, or both.

Particles in the immunogenic compositions of the invention typically comprise polymers that are sterilizable, substantially non-toxic and biodegradable. Such materials include polyesters (e.g., poly[hydroxy acids] such as polylactide and polyglcolide, poly[cyclic esters] such as caprolactone, etc.), polycarbonates, polyorthoesters, polyanhydrides, polycyanoacrylates, polyphosphazines, and combinations thereof, among others. More typically, particles for use with the present invention are polymer particles derived from poly (α-hydroxy acids), for example, from a poly(lactide) ("PLA") such as poly(L-lactide) or poly(D,L-lactide), from a copolymer of lactide and glycolide ("PLGA") such as a poly(L-lactide-co-glycolide) or poly(D,L-lactide-co-glycolide), or from a copolymer of lactide and caprolactone, among others. The polymer particles may thus be formed using any of various polymeric starting materials which have a variety of molecular weights and, in the case of the copolymers, such as PLGA, a variety of monomer (e.g., lactide:glycolide) ratios, the selection of which will be largely a matter of choice, depending in part on the coadministered species. These and other parameters are discussed below.

Cationic surfactants for use in the compositions of the invention vary widely and numerous examples are described below. In certain preferred embodiments, the cationic surfactant is selected from (1,2-dioleoyloxypropyl)-N,N,N-trimethylammonium salt (DOTAP), dimethyldioctadecylammonium salt (DDA), and 3-beta-[N—(N',N'-dimethylaminoethane) carbamoyl]cholesterol (DC-Chol), among many other possibilities.

Non-ionic surfactants for use in the compositions of the invention vary widely and numerous examples are described below. In certain preferred embodiments, the non-ionic surfactant is selected from poly(vinyl alcohol), polysorbate (e.g., polysorbate 20, polysorbate 80) and poloxamers, among many other possibilities.

In certain embodiments, microparticle compositions in accordance with the invention will comprise a polyol, a carbohydrate, or both.

RNA replicons for use in the invention vary widely and include alphavirus replicons, for example, alphavirus replicons derived from Sindbis (SIN), Venezuelan equine encephalitis (VEE), Semliki Forest virus (SFV), and combinations thereof, among other alphaviruses.

Antigens expressed by the RNA replicons in accordance with the invention include antigens associated with viruses, bacteria, parasites, fungi and other microbes, as well as any of the various tumor antigens.

The net charge of a given particle population may be measured using known techniques including measurement of the particle zeta potential. In certain embodiments, particle suspensions in accordance with the invention have a positive zeta potential.

For example, in the case of lyophilized compositions, upon the addition of water in an amount such that the particles are present in a concentration of 1-25 mg/ml (e.g, ranging from 1 to 2 to 5 to 10 to 15 to 20 to 25 mg/ml), based on N:P ratio and loading of cationic surfactant, a suspension may be formed in which the suspended particles have a zeta potential that is greater than +20 mV, for example ranging from +20 mV to +25 mV to +30 mV to +35 mV to +40 mV to +45 mV to +50 mV to +55 mV to +60 mV or more.

In various embodiments, the lyophilized compositions have a zeta potential in accordance with the preceding range when suspended at a concentration suitable for administration. For example, lyophilized compositions in accordane with the present invention may be provided to health care professionals along with instructions regarding the proper volume of fluid (e.g, water for injection, etc.) to be used for resuspension/reconstitution of the composition.

In certain embodiments, particle compositions in accordance with the present invention can comprise immunological adjuvants. Examples of immunological adjuvants include CpG oligonucleotides, double-stranded RNA, *E. coli* heat-labile toxins, alum, liposaccharide phosphate compounds, liposaccharide phosphate mimetics, monophosphoryl lipid A analogues, small molecule immune potentiators, muramyl tripeptide phosphatidylethanolamine, and tocopherols, among many others.

The immunological adjuvants may be, for example, associated with the surface of the particles (e.g., adsorbed or otherwise bound), entrapped within the particles, or both. In certain embodiments, an immunological adjuvant may be associated with the surface of or entrapped within a population of particles that is different from positively charged particles comprising adsorbed RNA replicon.

In other aspects, the present invention provides methods of producing immunogenic compositions.

For example, in some embodiments, a method is provided for forming an immunogenic composition that comprises: (a) providing positively charged particles that comprise a biodegradable polymer and a cationic surfactant and (b) adsorbing an RNA replicon comprising at least one polynucleotide encoding at least one antigen adsorbed to the positively charged particles, wherein the ratio of the number of moles of cationic nitrogen in the cationic surfactant to the number of moles of anionic phosphate in the RNA replicon (N:P ratio) ranges from 10:1 to 1:10.

In other embodiments, a method is provided for forming an immunogenic composition that comprises: (a) providing a first suspension comprising positively charged particles that comprise a biodegradable polymer and a cationic surfactant; (b) adsorbing an RNA replicon comprising at least one polynucleotide encoding at least one antigen to the nanoparticles in the first suspension to form a second suspension, (c) adding at least one additional component comprising a non-ionic surfactant to the second suspension to form a third suspension, and (d) lyophilizing the third suspension.

In certain of these embodiments, the first suspension is formed by a method comprising: (a) combining (i) a first liquid that comprises the biodegradable polymer and the cationic surfactant dissolved in an organic solvent with (ii) a second liquid that comprises water, whereupon the first suspension of nanoparticles comprising the biodegradable polymer and the cationic surfactant is formed.

In certain of these embodiments, at least one additional component is selected from polyols, carbohydrates and combinations thereof.

In still other aspects, the present invention provides methods of delivering the particle compositions to a host animal (e.g., for therapeutic, prophylactic, or diagnostic purposes). The host animal (also referred to as a "vertebrate subject" or "subject") is preferably a vertebrate animal, more preferably a mammal, and even more preferably a human.

In still other aspects of the invention, an immune response is stimulated in a vertebrate host animal upon administering the immunogenic compositions described herein to the animal.

These and other aspects and embodiments of the present invention will become more readily apparent to those of ordinary skill in the art in view of the disclosure herein.

BRIEF DESCRIPTION OF THE DRAWINGS

FIGS. 1A-1F show a nucleic acid sequence (SEQ ID NO:1) for a plasmid encoding pT7-mVEEV-FL.RSVF (A317).

FIGS. 2A-2F show a nucleic acid sequence (SEQ ID NO:2) for a plasmid encoding pT7-VEEV-SEAP (A306).

FIGS. 3A-3G show a nucleic acid sequence (SEQ ID NO:3) for a plasmid encoding VEE/SIN self-replicating RNA containing full length RSV-F and SP6 promoter (A4).

FIG. 4 shows a gel for 4% w/w PLG/DOTAP nanoparticles formed using either acetone (Type I) or ethyl acetate (Type II) as organic solvent with RNA adsorbed at a 10:1 N:P ratio. For each nanoparticle formulation the following is shown: (a) a gel lane corresponding to supernatant obtained from PLG particles that were untreated with RNase and centrifuged (to determine RNA adsorption efficiency), (b) a gel lane corresponding to a control in which RNA desorbed from PLG particles that were untreated with RNase, and (c) a gel lane corresponding to RNA adsorbed to PLG particles that were treated with RNAse followed by desorption from PLG particles.

FIG. 5 shows a gel for 4% w/w PLG/DOTAP microparticles with RNA adsorbed at N:P ratios of 10:1, 4:1 and 1:4. For each microparticle formulation the following is shown: (a) a gel lane corresponding to supernatant obtained from PLG particles that were untreated with RNase and centrifuged (to determine RNA adsorption efficiency), (b) a gel lane corresponding to a control in which RNA desorbed (decomplexed) from PLG particles that were untreated with RNase, and (c) a gel lane corresponding to RNA adsorbed to PLG particles that were treated with RNAse followed by desorption from PLG particles. Also shown are gel lanes for undigested and digested RNA controls.

FIG. 6A shows pooled SEAP expression (expressed as RLU) in mice for various formulations at 1, 3 and 6 days post-injection.

FIG. 6B shows individual SEAP expression (expressed as RLU) in mice for various formulations at 6 days post-injection.

FIG. 7 shows pooled SEAP expression (expressed as RLU) in mice for various formulations, including 4% w/w PLG nanoparticles Type I (acetone) and Type II (ethyl acetate), at 1, 3 and 6 days post-injection.

FIGS. 8A and 8B show results for 4% w/w PLG microparticles with adsorbed RSV-F RNA using different cationic surfactants (DOTAP, DDA and DC-Cholesterol) at N:P ratios of 10:1, 4:1 and 1:4. Also shown are data for naked RNA. Data are represented a) in FIG. 8A as IgG titers on days 13 and 28, and b) in FIG. 8B as fold-increase in day 28 IgG titers over 1 μg naked RNA (i.e., IgG titers with formulation/IgG titers with 1 μg naked RNA).

DETAILED DESCRIPTION OF THE INVENTION

The practice of the present invention will employ, unless otherwise indicated, conventional methods of chemistry, polymer chemistry, biochemistry, molecular biology, immunology and pharmacology, within the skill of the art. Such techniques are explained fully in the literature. See, e.g., *Remington's Pharmaceutical Sciences,* 18th ed. (Easton, Pa.: Mack Publishing Company, 1990); *Methods In Enzymology* (S. Colowick and N. Kaplan, eds., Academic Press, Inc.); Weir, D. M., *Handbook of Experimental Immunology*, Vols. I-IV, 5th ed. (Blackwell Publishers, 1996); Sambrook, J. et al., *Molecular Cloning: A Laboratory Manual,* 3rd ed. (Cold Spring Harbor Laboratory Press, 2001); Ausubel, F. M. et al., *Short Protocols In Molecular Biology,* 5th ed. (Current Protocols, 2002); *Handbook of Surface and Colloidal Chemistry* (Birdi, K. S., ed, CRC Press, 2003) and *Seymour/Carraher's Polymer Chemistry,* 5th ed. (Marcel Dekker Inc., 2007).

All publications, patents and patent applications cited herein, whether supra or infra, are hereby incorporated by reference in their entirety.

As used in this specification and any appended claims, the singular forms "a," "an" and "the" include plural references unless the content clearly dictates otherwise. Thus, for example, the term "particle" refers to one or more particles, and the like.

Unless stated otherwise or unless the context clearly dictates otherwise, all percentages and ratios herein are given on a weight basis.

A. DEFINITIONS

In describing the present invention, the following terms will be employed, and are intended to be defined as indicated below.

The term "particle" as used herein, refers to a particle having a size less than 10 μm (10,000 nm), for example, ranging from about 10 nm or less to 25 nm to 50 nm to 100 nm to 250 nm to 500 nm to 1000 nm (1 μm) to 2,500 nm (2.5 μm) to 5,000 nm (5 μm) to 10,000 nm (10 μm). In some embodiments, dry particles may exist in aggregates that are greater than 10,000 nm in diameter, but which disperse into particle sizes less than 10,000 nm upon addition of an aqueous fluid and mixing using techniques such as vortexing, among others. In some embodiments, the particles described herein can be generally spherical. In some embodiments, the particles described herein can be of irregular geometry. The particles within the compositions of the present invention typically have a size distribution in aqueous fluid, wherein the Z average and/or the D(v,0.5) value is less than 5,000 nm, for example, ranging from 5,000 nm to 2,500 nm to 1,000 nm to 500 nm to 250 nm to 100 nm to 50 nm or less.

As used herein "nanoparticles" are particles that have a size distribution in aqueous fluid in which the Z Average ranges from 50 nm to 500 nm. As used herein "microparticles" are particles that have a size distribution in aqueous fluid in which the D(v,0.5) ranges from 500 nm to 5000 nm.

Particle size can be determined (measured) using methods available in the art. For example, particle size can be determined using photon correlation spectroscopy, dynamic light scattering or quasi-elastic light scattering. These methods are based on the correlation of particle size with diffusion properties of particles obtained from Brownian motion measurements. Brownian motion is the random movement of the particles due to bombardment by the solvent molecules that surround the particles. The larger the particle, the more slowly the Brownian motion will be. Velocity is defined by the translational diffusion coefficient (D). The value measured refers to how a particle moves within a liquid (hydrodynamic diameter). The diameter that is obtained is the diameter of a sphere that has the same translational diffusion coefficient as the particle.

Particle size can also be determined using static light scattering, which measures the intensity of light scattered by particles in a solution at a single time. Static light scattering measures light intensity as a function of scattering angle and solute concentration. Particles passing though a light source, for example, a laser beam, scatter light at an angle that is inversely proportional to their size. Large particles generate a diffraction pattern at low scattering angles with high intensity, whereas small particles give rise to wide angle low intensity signals. Particle size distributions can be calculated if the intensity of light scattered from a sample are measured as a function of angle. The angular information is compared with a scattering model (e.g., Mie theory) in order to calculate the size distribution.

Generally, particle size is determined at room temperature and involves multiple analyses of the sample in question (e.g., at least 3 repeat measurements on the same sample) to yield an average value for the particle diameter.

For photon correlation spectroscopy, Z average (also called the cumulant mean or hydrodynamic diameter) is typically calculated from cumulants (monomodal) analysis.

For static light scattering measurements (and also for photon correlation spectroscopy in some embodiments), volume-based size parameters may be measured. For instance, D(v, 0.5) (where v means volume) is a size parameter whose value is defined as the point where 50% of the particles (volume basis) in the composition, as measured, have a size that is less than the D(v,0.5) value, and 50% of the particles in the composition have a size that is greater than the D(v,0.5) value. Similarly, D(v,0.9) is a size parameter whose value is defined as the point where 90% of the particles (volume basis) in the composition, as measured, have a size that is less than the D(v,0.9) value, and 10% of the particles in the composition have a size that is greater than the D(v,0.9) value.

As defined herein, a "suspension" is a liquid phase that contains suspended solid particulate material. Suspensions can be stable or unstable. As defined herein, a "solution" is a liquid phase that contains dissolved material. As defined herein, an "aqueous" suspension or solution is a suspension or solution that contains water, typically 50 wt % water or more, for example, ranging from 50 wt % to 75 wt % to 90 wt % to 95 wt % or more water.

As defined herein, "dry" particle compositions are particle compositions that are not immersed in a liquid (e.g., not within a liquid suspension). Typically, a "dry" particle composition will comprise less than 3% water.

As defined herein, "blank" particle compositions are particle compositions that are free of active agents (i.e., they are free of pharmaceuticals, including drugs, RNA replicons, immunological adjuvants, etc.).

"Zeta potential," as used herein, refers to the electrical potential that exists across the interface of all solids and liquids, e.g., the potential across the diffuse layer of ions surrounding a charged colloidal particle. Zeta potential can be calculated from electrophoretic mobilities, i.e., the rates at which colloidal particles travel between charged electrodes placed in contact with the substance to be measured, using techniques well known in the art.

The term "surfactant" comes from the phrase "surface active agent". Surfactants accumulate at interfaces (e.g., at liquid-liquid, liquid-solid and/or liquid-gas interfaces) and change the properties of that interface. As used herein, surfactants include detergents, dispersing agents, suspending agents, emulsion stabilizers, cationic lipids, anionic lipids, zwitterionic lipids, and the like.

As defined herein, "carbohydrates" include monosaccharides, oligosaccharides and polysaccharides, as well as substances derived from monosaccharides, for example, by reduction (e.g., alditols), by oxidation of one or more terminal groups to carboxylic acids (e.g., glucuronic acid), or by replacement of one or more hydroxy group(s) by a hydrogen atom or an amino group (e.g., beta-D-glucosamine and beta-D-galactosamine).

As defined herein, a "monosaccharide" is a polyhydric alcohol, i.e., an alcohol that further comprises either an aldehyde group (in which case the monosaccharide is an aldose) or a keto group (in which case the monosaccharide is a ketose). Monosaccharides typically contain from 3-10 carbons. Moreover, monosaccharides commonly have the empirical formula $(CH_2O)_n$ where n is an integer of three or greater, typically 3-10. Examples of 3-6 carbon aldoses include glyceraldehyde, erythrose, threose, ribose, 2-deoxyribose, arabinose, xylose, lyxose, allose, altrose, glucose, mannose, gulose, idose, galactose, and talose. Examples of 3-6 carbon ketoses include dihydroxyacetone, erythrulose, ribulose, xylulose, psicose, fructose, sorbose, and tagatose. Naturally occurring monosaccharides are normally found in the D-isomer form, as opposed to the L-form.

An "oligosaccharide" refers to a relatively short monosaccharide polymer, i.e., one containing from 2 to 30 monosaccharide units. A "polysaccharide" is a monosaccharide polymer that is beyond oligosaccharide length (i.e., one containing more than 30 monosaccharide units). Moreover, as used herein, the term "polysaccharide" also refers to a monosaccharide polymer that contains two or more linked monosaccharides. To avoid ambiguity, the second definition is to be applied at all times, unless there are explicit indications to the contrary. The term "polysaccharide" also includes polysaccharide derivatives, such as amino-functionalized and carboxyl-functionalized polysaccharide derivatives, among many others. Monosaccharides are typically linked by glycosidic linkages. Specific examples include disaccharides (such as sucrose, lactose, trehalose, maltose, gentiobiose and cellobiose), trisaccharides (such as raffinose), tetrasaccharides (such as stachyose), and pentasaccharides (such as verbascose).

As used herein the term "saccharide" encompasses monosaccharides, oligosaccharides and polysaccharides. A "saccharide-containing species" is a molecule, at least a portion of which is a saccharide. Examples include saccharide cryoprotective agents, saccharide antigens, antigens comprising saccharides conjugated to carrier peptides, and so forth. A "polysaccharide-containing species" is a molecule, at least a portion of which is a polysaccharide.

As used herein, a "cryoprotective agent" is an agent that protects a composition from experiencing adverse effects upon freezing and thawing. For example, in the present invention, cryoprotective agents such as polyols and/or carbohydrates, among others, may be added to prevent substantial particle agglomeration from occurring when the lyophilized compositions of the invention are resuspended.

As used herein, the term "polynucleotide" means a homopolymer or heteropolymer of at least 2 nucleotide units (also referred to herein as "nucleotides"). Nucleotides forming polynucleotides as defined herein include naturally occurring nucleotides, such as ribonucleotides and deoxyribinucleotides, as well as equivalents, derivatives, variants and analogs of naturally occurring nucleotides.

A polynucleotide may be in either single-stranded form or multi-stranded form (e.g., double-stranded, triple-stranded, etc.). A polynucleotide may be in linear form or non-linear form (e.g., comprising circular, branched, etc. elements). A polynucleotide may be natural, synthetic or a combination of both.

A polynucleotide may be capable of self-replication when introduced into a host cell. Examples of polynucleotides thus include self-replicating RNAs and DNAs and, for instance, selected from replicons, plasmids, cosmids, phagemids, transposons, viral vectors, artifical chromosomes (e.g., bacterial, yeast, etc.) as well as other self-replicating species. Polynucleotides include those that express antigenic polypeptides in a host cell (e.g., polynucleotide-containing antigens). Polynucleotides include self-replicating polynucleotides within which natural or synthetic sequences derived from eucaryotic or prokaryotic organisms (e.g., genomic DNA sequences, genomic RNA sequences, cDNA sequences, etc.) have been inserted. Specific examples of self-replicating polynucleotides include RNA vector constructs and DNA vector constructs, among others. Sequences that may be expressed include native sequences and modifications, such as deletions, additions and substitutions (generally conservative in nature), to native sequences, among others. These modifications may be deliberate, as through site-directed mutagenesis, or may be accidental, such as through mutations of hosts that produce antigens.

As define herein an "oligonucleotide" is a polynucleotide having in the range of 5 to 100 and more preferably 5 to 30 nucleotides in size.

As used herein, the phrase "nucleic acid" includes DNA, RNA, and chimeras formed therefrom.

A "polynucleotide-containing species" is a molecule, at least a portion of which is a polynucleotide.

The terms "polypeptide" and "protein" refer to a polymer of amino acid residues and are not limited to a minimum length of the product. Thus, peptides, oligopeptides, dimers, multimers, and the like, are included within the definition. Both full-length proteins and fragments thereof are encompassed by the definition. The terms also include modifications, such as deletions, additions and substitutions (generally conservative in nature), to a native sequence, for example, such that the protein maintains the ability to elicit an immunological response or have a therapeutic effect on a subject to which the protein is administered.

A "polypeptide-containing species" is a molecule, at least a portion of which is a polypeptide. Examples include polypeptides, proteins including glycoproteins, saccharide antigens conjugated to carrier proteins, and so forth.

The term "pharmaceutical" refers to biologically active compounds such as drugs, antibiotics, antiviral agents, growth factors, hormones, antigens, polynucleotides, adjuvants and the like.

The term "adjuvant" refers to any substance that assists or modifies the action of a pharmaceutical, including but not limited to immunological adjuvants, which increase or diversify the immune response to an antigen. Hence, immunological adjuvants are compounds that are capable of potentiating an immune response to antigens. Immunological adjuvants can potentiate humoral and/or cellular immunity.

By "antigen" is meant a molecule that contains one or more epitopes capable of stimulating a host's immune system to make a cellular antigen-specific immune response when the antigen is presented, or a humoral antibody response. An antigen may be capable of eliciting a cellular and/or humoral response by itself or when present in combination with another molecule.

An "epitope" is that portion of an antigenic molecule or antigenic complex that determines its immunological specificity. An epitope is within the scope of the present definition of antigen. Commonly, an epitope is a polypeptide or polysaccharide in a naturally occurring antigen. In artificial antigens it can be a low molecular weight substance such as an arsanilic acid derivative. An epitope will react specifically in vivo or in vitro with, for example, homologous antibodies or T lymphocytes. Alternative descriptors are antigenic determinant, antigenic structural grouping and haptenic grouping.

Frequently, an epitope will include between about 5 to 15 amino acids. Epitopes of a given protein can be identified using any number of epitope mapping techniques, well known in the art. See, e.g., *Epitope Mapping Protocols in Methods in Molecular Biology*, Vol. 66 (Glenn E. Morris, Ed., 1996) Humana Press, Totowa, N.J. For example, linear epitopes may be determined by, for example, concurrently synthesizing large numbers of peptides on solid supports, the peptides corresponding to portions of the protein molecule, and reacting the peptides with antibodies while the peptides are still attached to the supports. Such techniques are known in the art and described in, e.g., U.S. Pat. No. 4,708,871; Geysen et al. (1984) (*Proc. Natl. Acad. Sci. USA* 81:3998-4002); Geysen et al. (1986) (*Molec. Immunol.* 23:709-715). Similarly, conformational epitopes are readily identified by determining spatial conformation of amino acids such as by, e.g., x-ray crystallography and two-dimensional nuclear magnetic resonance. See, e.g., *Epitope Mapping Protocols, supra.*

The term "antigen" as used herein denotes both subunit antigens, i.e., antigens which are separate and discrete from a whole organism with which the antigen is associated in nature, as well as killed, attenuated or inactivated bacteria, viruses, parasites or other pathogens or tumor cells. Antibodies such as anti-idiotype antibodies, or fragments thereof, and synthetic peptide mimotopes, which can mimic an antigen or antigenic determinant, are also captured under the definition of antigen as used herein.

Furthermore, for purposes of the present invention, an "antigen" refers to a protein having modifications, such as deletions, additions and substitutions (generally conservative in nature), to the native sequence, as long as the protein maintains the ability to elicit an immunological response. These modifications may be deliberate, as through site-directed mutagenesis, or may be accidental, such as through mutations of hosts which produce the antigens. Antigens can be derived from any of the various viruses, bacteria, parasites, fungi and other microbes, as well as any of the various tumor antigens.

An "immunological response" or "immune response" to a composition of interest is the development in a subject of a humoral and/or a cellular immune response to molecules present in the composition.

Immune responses include innate and adaptive immune responses. Innate immune responses are fast-acting responses that provide a first line of defense for the immune system. In contrast, adaptive immunity uses selection and clonal expansion of immune cells having somatically rearranged receptor genes (e.g., T- and B-cell receptors) that recognize antigens from a given pathogen or disorder (e.g., a tumor), thereby providing specificity and immunological memory. Innate immune responses, among their many effects, lead to a rapid burst of inflammatory cytokines and activation of antigen-presenting cells (APCs) such as macrophages and dendritic cells. To distinguish pathogens from self-components, the innate immune system uses a variety of relatively invariable receptors that detect signatures from pathogens, known as pathogen-associated molecular patterns, or PAMPs. The addition of microbial components to experimental vaccines is known to lead to the development of robust and durable adaptive immune responses. The mechanism behind this potentiation of the immune responses has been reported to involve pattern-recognition receptors (PRRs), which are differentially expressed on a variety of immune cells, including neutrophils, macrophages, dendritic cells, natural killer cells, B cells and some nonimmune cells such as epithelial and endothelial cells. Engagement of PRRs leads to the activation of some of these cells and their secretion of cytokines and chemokines, as well as maturation and migration of other cells. In tandem, this creates an inflammatory environment that leads to the establishment of the adaptive immune response. PRRs include nonphagocytic receptors, such as Toll-like receptors (TLRs) and nucleotide-binding oligomerization domain (NOD) proteins, and receptors that induce phagocytosis, such as scavenger receptors, mannose receptors and β-glucan receptors.

Reported TLRs (along with examples of some reported TLR agonists, which may be used as immunological adjuvants in various embodiments of the invention) include the following: TLR1 (bacterial lipoproteins from *Mycobacteria, Neisseria*), TLR2 (zymosan yeast particles, peptidoglycan, lipoproteins, glycolipids, lipopolysaccharide), TLR3 (viral double-stranded RNA, poly:IC), TLR4 (bacterial lipopolysaccharides, plant product taxol), TLR5 (bacterial flagellins), TLR6 (yeast zymosan particles, lipotechoic acid, lipopeptides from mycoplasma), TLR7 (single-stranded RNA, imiquimod, resimiquimod, and other synthetic compounds such as loxoribine and bropirimine), TLR8 (single-stranded RNA, resimiquimod) and TLR9 (CpG oligonucleotides), among others. Dendritic cells are recognized as some of the most important cell types for initiating the priming of naive CD4' helper T ($T_H$) cells and for inducing CD8' T cell differentiation into killer cells. TLR signaling has been reported to play an important role in determining the quality of these helper T cell responses, for instance, with the nature of the TLR signal determining the specific type of $T_H$ response that is observed (e.g., $T_H1$ versus $T_H2$ response). A combination of antibody (humoral) and cellular immunity are produced as part of a $T_H1$-type response, whereas a $T_H2$-type response is predominantly an antibody response. Various TLR ligands such as CpG DNA (TLR9) and imidazoquinolines (TLR7, TLR8) have been documented to stimulate cytokine production from immune cells in vitro. The imidazoquinolines are the first small, drug-like compounds shown to be TLR agonists. For further information, see, e.g., A. Pashine, N. M. Valiante and J. B. Ulmer, *Nature Medicine* 11, S63-S68 (2005), K. S. Rosenthal and D. H. Zimmerman, *Clinical and Vaccine Immunology,* 13(8), 821-829 (2006), and the references cited therein.

For purposes of the present invention, a "humoral immune response" refers to an immune response mediated by antibody molecules, while a "cellular immune response" is one mediated by T-lymphocytes and/or other white blood cells. One important aspect of cellular immunity involves an antigen-specific response by cytolytic T-cells ("CTLs"). CTLs have specificity for peptide antigens that are presented in association with proteins encoded by the major histocompatibility complex (MHC) and expressed on the surfaces of cells. CTLs help induce and promote the intracellular destruction of intracellular microbes, or the lysis of cells infected with such microbes. Another aspect of cellular immunity involves an antigen-specific response by helper T-cells. Helper T-cells act to help stimulate the function, and focus the activity of, non-specific effector cells against cells displaying peptide antigens in association with MHC molecules on their surface. A "cellular immune response" also refers to the production of cytokines, chemokines and other such molecules produced by activated T-cells and/or other white blood cells, including those derived from CD4+ and CD8+ T-cells.

A composition such as an immunogenic composition or a vaccine that elicits a cellular immune response may serve to sensitize a vertebrate subject by the presentation of antigen in association with MHC molecules at the cell surface. The cell-mediated immune response is directed at, or near, cells presenting antigen at their surface. In addition, antigen-specific T-lymphocytes can be generated to allow for the future protection of an immunized host.

The ability of a particular composition to stimulate a cell-mediated immunological response may be determined by a number of assays known in the art, such as by lymphoproliferation (lymphocyte activation) assays, CTL cytotoxic cell assays, by assaying for T-lymphocytes specific for an antigen in a sensitized subject, or by measurement of cytokine production by T cells in response to restimulation with antigen. Such assays are well known in the art. See, e.g., Erickson et al. (1993) (*J. Immunol.* 151:4189-4199); Doe et al. (1994) (*Eur. J. Immunol.* 24:2369-2376).

Hence, an immunological response may include, for example, one or more of the following effects among others: the production of antibodies by, for example, B-cells; and/or the activation of suppressor T-cells and/or γδ T-cells directed specifically to an antigen or antigens present in the composition or vaccine of interest. These responses may serve, for example, to neutralize infectivity, and/or mediate antibody-complement, or antibody dependent cell cytotoxicity (ADCC) to provide protection to an immunized host. Such responses can be determined, for instance, using standard immunoassays and neutralization assays, well known in the art, for instance, radioimmunoassays and ELISAs.

An immunogenic composition which contains an antigen or a polynucleotide (e.g., vector construct) that leads to expression of an antigen in accordance with the present invention displays "enhanced immunogenicity" when it possesses a greater capacity to elicit an immune response than the immune response elicited by an equivalent amount of the antigen/polynucleotide administered using a different delivery system, for example, wherein the antigen/polynucleotide is administered in a "naked" state independent of particles formed from biodegradable polymer(s). An immunogenic composition may display "enhanced immunogenicity," for example, because the composition is more strongly immunogenic or because a lower dose or fewer doses of the composition are necessary to achieve an immune response in the subject to which the composition is administered. Such enhanced immunogenicity can be determined by administering the composition and suitable controls to animals and comparing antibody titers and/or cellular-mediated immunity against the two using standard assays.

As used herein, "treatment" refers to any of (i) the prevention of a pathogenic infection or disorder (e.g. cancer) in question in a vertebrate subject, (ii) the reduction or elimination of symptoms in a vertebrate subject having the pathogenic infection or disorder in question, and (iii) the substantial or complete elimination of the pathogenic infection or disorder in question in a vertebrate subject. Treatment may be effected prophylactically (prior to arrival of the pathogenic infection or disorder in question) or therapeutically (following arrival of the same).

The terms "effective amount" or "pharmaceutically effective amount" of an immunogenic composition of the present invention refer herein to a sufficient amount of the immunogenic composition to treat or diagnose a condition of interest. The exact amount required will vary from subject to subject, depending, for example, on the species, age, and general condition of the subject; the severity of the condition being treated; the particular antigen of interest; in the case of an immunological response, the capacity of the subject's immune system to synthesize antibodies, for example, and the degree of protection desired; and the mode of administration, among other factors. An appropriate "effective" amount in any individual case may be determined by one of ordinary skill in the art. Thus, a "therapeutically effective amount" will typically fall in a relatively broad range that can be determined through routine trials.

By "vertebrate subject" or "vertebrate animal" is meant any member of the subphylum cordata, including, without limitation, mammals such as cattle, sheep, pigs, goats, horses, and humans; domestic animals such as dogs and cats; and birds, including domestic, wild and game birds such as cocks and hens including chickens, turkeys and other gallinaceous birds. The term does not denote a particular age. Thus, both adult and newborn animals are covered.

By "pharmaceutically acceptable" or "pharmacologically acceptable" is meant a material which is not biologically or otherwise undesirable, i.e., the material may be administered to an individual without causing any excessively undesirable biological effects in the individual or interacting in an excessively deleterious manner with any of the components of the composition in which it is contained.

The term "excipient" refers to any essentially accessory substance that may be present in the finished dosage form. For example, the term "excipient" includes vehicles, binders, disintegrants, fillers (diluents), lubricants, glidants (flow enhancers), compression aids, colors, sweeteners, preservatives, suspending/dispersing agents, film formers/coatings, flavors and printing inks.

By "physiological pH" or a "pH in the physiological range" is meant a pH in the range of approximately 7.0 to 8.0, more typically in the range of 7.2 to 7.6.

As used herein, the phrase "vector construct" generally refers to any assembly that is capable of directing the expression of a nucleic acid sequence(s) or gene(s) of interest. A vector construct typically includes transcriptional promoter/enhancer or locus defining element(s), or other elements which control gene expression by other means such as alternate splicing, nuclear RNA export, post-translational modification of messenger, or post-transcriptional modification of protein. In addition, the vector construct typically includes a sequence which, when transcribed, is operably linked to the sequence(s) or gene(s) of interest and acts as a translation initiation sequence. The vector construct may also optionally include a signal that directs polyadenylation, a selectable marker, as well as one or more restriction sites and a translation termination sequence. In addition, if the vector construct is placed into a retrovirus, the vector construct may include a packaging signal, long terminal repeats (LTRs), and positive and negative strand primer binding sites appropriate to the retrovirus used (if these are not already present).

A "DNA vector construct" refers to a DNA molecule that is capable of directing the expression of a nucleic acid sequence(s) or gene(s) of interest.

One specific type of DNA vector construct is a plasmid, which is a circular episomal DNA molecule capable of autonomous replication within a host cell. Typically, a plasmid is a circular double stranded DNA, loop into which additional DNA segments can be ligated. pCMV is one specific plasmid that is well known in the art. A preferred pCMV vector contains the immediate-early enhancer/promoter of CMV and a bovine growth hormone terminator. A specific example is described in detail in Chapman, B. S., et al. (1991) (*Nucleic Acids Res.* 19:3979-3986).

Other DNA vector constructs are known, which are based on RNA viruses. These DNA vector constructs typically comprise a promoter that functions in a eukaryotic cell, 5' of a cDNA sequence for which the transcription product is an RNA vector construct (e.g., an alphavirus RNA vector replicon), and a 3' termination region. The RNA vector construct preferably comprises an RNA genome from a picornavirus, togavirus, flavivirus, coronavirus, paramyxovirus, yellow fever virus, or alphavirus (e.g., Sindbis virus, Semliki Forest virus, Venezuelan equine encephalitis virus, or Ross River virus), which has been modified by the replacement of one or more structural protein genes with a selected heterologous nucleic acid sequence encoding a product of interest. The RNA vector constructs can be obtained by transcription in vitro from a DNA template. Specific examples include Sindbis-virus-based plasmids (pSIN) such as pSINCP, described, for example, in U.S. Pat. Nos. 5,814,482 and 6,015,686, as well as in International Publication Nos. WO 97/38087, WO 99/18226 and WO 02/26209. The construction of such vectors, in general, is described in U.S. Pat. Nos. 5,814,482 and 6,015,686.

Other examples of vector constructs include RNA vector constructs (e.g., alphavirus vector constructs) and the like. As used herein, "RNA vector construct", "RNA vector replicon", "RNA replicon", "replicon vector" and "replicon" refer to an RNA molecule that is capable of directing its own amplification or self-replication in vivo, typically within a target cell. The RNA vector construct is used directly, without the requirement for introduction of DNA into a cell and transport to the nucleus where transcription would occur. By using the RNA vector for direct delivery into the cytoplasm of the host cell, autonomous replication and translation of the heterologous nucleic acid sequence occurs efficiently.

In one aspect, the self-replicating RNA molecule is derived from or based on an alphavirus. In other aspects, the self-replicating RNA molecule is derived from or based on a virus other than an alphavirus, preferably, a positive-stranded RNA virus, and more preferably a picornavirus, flavivirus, rubivirus, pestivirus, hepacivirus, calicivirus, or coronavirus. Suitable wild-type alphavirus sequences are well-known and are available from sequence depositories, such as the American Type Culture Collection, Rockville, Md. Representative examples of suitable alphaviruses include Aura (ATCC VR-368), Bebaru virus (ATCC VR-600, ATCC VR-1240), Cabassou (ATCC VR-922), Chikungunya virus (ATCC VR-64, ATCC VR-1241), Eastern equine encephalomyelitis virus (ATCC VR-65, ATCC VR-1242), Fort Morgan (ATCC VR-924), Getah virus (ATCC VR-369, ATCC VR-1243), Kyzylagach (ATCC VR-927), Mayaro (ATCC VR-66), Mayaro virus (ATCC VR-1277), Middleburg (ATCC VR-370), Mucambo virus (ATCC VR-580, ATCC VR-1244), Ndumu (ATCC VR-371), Pixuna virus (ATCC VR-372, ATCC VR-1245), Ross River virus (ATCC VR-373, ATCC VR-1246), Semliki Forest (ATCC VR-67, ATCC VR-1247), Sindbis virus (ATCC VR-68, ATCC VR-1248), Tonate (ATCC VR-925), Triniti (ATCC VR-469), Una (ATCC VR-374), Venezuelan equine encephalomyelitis (ATCC VR-69, ATCC VR-923, ATCC VR-1250 ATCC VR-1249, ATCC VR-532), Western equine encephalomyelitis (ATCC VR-70, ATCC VR-1251, ATCC VR-622, ATCC VR-1252), Whataroa (ATCC VR-926), and Y-62-33 (ATCC VR-375).

B. General Methods

1. Polymeric Particles

Immunogenic compositions in accordance with the present invention comprise polymeric particles. A "polymeric particle" is a particle that comprises one or more types of polymers, typically, 50 wt % or more polymers, for example, from 50 wt % to 75 wt % to 90 wt % to 95 wt % to 97.5 wt % to 99 wt % or more.

As used herein, "polymers" are molecules containing multiple copies (e.g., 5 to 10 to 25 to 50 to 100 to 250 to 500 to 1000 or more copies) of one or more constitutional units, commonly referred to as monomers. As used herein, "monomers" may refer to free monomers and to those are incorporated into polymers, with the distinction being clear from the context in which the term is used.

As used herein, a polymer is "biodegradable" if it undergoes bond cleavage along the polymer backbone in vivo, regardless of the mechanism of bond cleavage (e.g., enzymatic breakdown, hydrolysis, oxidation, etc.).

Polymers may take on a number of configurations, which may be selected, for example, from linear, cyclic, and branched configurations. Branched configurations include star-shaped configurations (e.g., configurations in which three or more chains emanate from a single branch region), comb configurations (e.g., configurations having a main chain and a plurality of side chains), dendritic configurations (e.g., arborescent and hyperbranched polymers), network configurations (e.g., crosslinked polymers), and so forth.

As used herein, "homopolymers" are polymers that contain multiple copies of a single constitutional unit. "Copolymers" are polymers that contain multiple copies of at least two dissimilar constitutional units, examples of which include random, statistical, gradient, periodic (e.g., alternating) and block copolymers.

As used herein, "block copolymers" are copolymers that contain two or more polymer blocks that differ, for instance, because a constitutional unit (i.e., monomer) is found in one polymer block that is not found in another polymer block.

As used herein, a "polymer block" is a grouping of constitutional units (e.g., 5 to 10 to 25 to 50 to 100 to 250 to 500 to 1000 or more units) that forms part or all of a polymer. Blocks can be branched or unbranched. Polymer blocks can contain a single type of constitutional unit (also referred to herein as "homopolymer blocks") or multiple types of constitutional units (also referred to herein as "copolymer blocks") which may be provided, for example, in a periodic (e.g., alternating), random, statistical or gradient distribution.

A few examples of block copolymer structures include the following, among others: (a) block copolymers having alternating blocks of the type $(AB)_m$, $B(AB)_m$ and $A(BA)_m$ where A is a first polymer block, B is a second polymer block that is different from the first polymer block, and m is a positive whole number of 1 or more, and (b) block copolymers having multi-arm architectures, such as $X(BA)_n$, and $X(AB)_n$, where n is a positive whole number of 2 or more and X is a hub species (e.g., an initiator molecule residue, a residue of a molecule to which preformed polymer chains are attached, etc.). In addition to the hub species mentioned above, polymers (including block copolymers) can contain a variety of other non-polymer-chain species, including initiator residues, linking molecule residues and capping molecules, among other species. Note that such non-polymeric species are generally ignored in describing polymers (including block copolymers). Thus, an $X(BA)_2$ block copolymer is generally designated as an ABA triblock copolymer, an $X(BA)_3$ block copolymer is generally referred to as a star polymer with a B midblock and three A endblocks. Other examples of block copolymers include comb copolymers having a B chain backbone and multiple A side chains, as well as comb copolymers having an A chain backbone and multiple B side chains.

As noted above a "polymer block" is defined herein as a grouping of constitutional units that forms part or all of a polymer. Thus, homopolymers may be said to contain a single homopolymer block. Copolymers, on the other hand, may contain a single copolymer block (e.g., a periodic copolymer block, a random copolymer block, a gradient copolymer block, etc.) or multiple homopolymer and/or copolymer blocks (e.g., a block copolymer comprising multiple differing homopolymer blocks, a block copolymer comprising multiple differing copolymer blocks, or a block copolymer comprising one or more homopolymer blocks and one or more copolymer blocks).

Polymers for use in the polymeric particles of the invention are preferably at least partially biodegradable.

Examples of polymers that are at least partially biodegradable include homopolymers formed from a single biodegradable homopolymer block, non-block copolymers formed from a single biodegradable copolymer block (e.g., selected from alternating, random, gradient, etc., blocks), and block copolymers containing at least one biodegradable polymer block, for example, a block copolymer containing two or more biodegradable polymer blocks or a block copolymer containing one or more biodegradable polymer blocks and one or more additional polymer blocks.

Examples of biodegradable polymers include, for example, homopolymers and copolymers of the following: polyesters (e.g., poly[hydroxy acids], poly[cyclic esters], etc.), polycarbonates, polyorthoesters, polyanhydrides, polycyanoacrylates (e.g., polyalkylcyanoacrylate or "PACA") and polyphosphazines.

Examples of biodegradable polymers include block copolymers containing combinations of two or more biodegradable polymer blocks corresponding to the foregoing (e.g., two or more blocks selected from polyester, polycarbonate, polyorthoester, polyanhydride, polycyanoacrylate and/or polyphosphazine blocks), and block copolymer comprising one or more of the foregoing biodegradable polymer blocks and one or more additional polymer blocks that differs from the foregoing biodegradable polymer blocks.

Examples of additional polymer blocks include hydrophilic polymer blocks such as polyether blocks, for example, polyethylene oxide (e.g. polyethylene glycol) blocks (see Park et al., *Langmuir* 20(6): 2456-2465 (2004)) and polypropylene oxide (e.g., polypropylene glycol) blocks, polyvinyl alcohol blocks, polyvinylpyrrolidone blocks, poly(acrylic acid) blocks, poly(methacrylic acid) blocks, poly(N-isopropylacrylamide-co-N,N-dimethylacrylamide) blocks (see Liu et al., *Biomaterials* 26(24): 5064-5074 (2005)), polyethylenimine blocks (see Nam et al., *Biomaterials* 24(12): 2053-2059 (2003)), poly(amino acid) blocks, and so forth. Examples of additional polymer blocks also include polymer blocks that are negatively charged at physiological pH, for instance, poly(carboxylic acids) such as poly(acrylic acid) blocks and poly(methacrylic acid) blocks, and certain polyaminoacid blocks (depending on the isoelectric point), as well as salts thereof, among others. Further examples of additional polymer blocks include polymer blocks that are positively charged at physiological pH, for instance, polyamine blocks such as polyethylenimine blocks and chitosan blocks, and certain polyaminoacid blocks (depending on the isoelectric point), as well as salts thereof, among others. Such polymers with charged polymer blocks may be employed, for example, as particle charge inducing agents (see below). In certain embodiments, AB diblock copolymers, ABA triblock copolymers, and BAB triblock copolymers are employed, where A designates an additional polymer block and B designates a biodegradable polymeric block.

In various preferred embodiments, biodegradable polymers are formed, for example, from the following: polyesters (e.g., polyhydroxy acids, polycaprolactone, polydioxanone, etc.), polycarbonates, polyorthoesters, polyanhydrides, polyphosphazines, and combinations thereof. More typical are polyesters, for example, homopolymers and copolymers of glycolic acid, L-lactic acid, D,L-lactic acid, hydroxybutyric acid, hydroxyvaleric acid, caprolactone and dioxanone, among others. Even more typical are homopolymers and copolymers of L-lactide, D,L-lactide, and glycolide, for example, polyglycolide, polylactide, for example, poly(L-lactide) or poly(D,L-lactide) (referred to as PLA herein) and poly(lactide-co-glycolide), for example, poly(L-lactide-co-glycolide) and poly(D,L-lactide-co-glycolide) (designated as "PLG" or "PLGA" herein).

The above polymers are available in a variety of molecular weights, and a suitable molecular weight for a given use is readily determined by one of skill in the art. Thus, for example, a suitable molecular weight for PLA may be on the order of about 2,000 to 5,000, among other values. A suitable molecular weight for PLG may range from about 5,000 to about 200,000, among other values.

Where copolymers are employed, copolymers with a variety of monomer ratios may be available. For example, where PLG is used to form the particles, a variety of lactide:glycolide molar ratios will find use herein, and the ratio is largely a matter of choice, depending in part on any coadministered adsorbed and/or entrapped species and the rate of degradation desired. For example, a 50:50 PLG polymer, containing 50% D,L-lactide and 50% glycolide, will provide a faster resorbing copolymer, while 75:25 PLG degrades more slowly, and 85:15 and 90:10, even more slowly, due to the increased lactide component. Mixtures of particles with varying lactide:glycolide ratios may also find use herein in order to achieve the desired release kinetics. Degradation rate of the particles of the present invention can also be controlled by such factors as polymer molecular weight and polymer crystallinity.

Where used, PLG copolymers are typically those having a lactide/glycolide molar ratio ranging, for example, from 20:80 to 25:75 to 40:60 to 45:55 to 50:50 to 55:45 to 60:40 to 75:25 to 80:20, and having a molecular weight ranging, for example, from 2,500 to 5,000 to 10,000 to 20,000 to 40,000 to 50,000 to 70,000 to 100,000 to 200,000 Daltons, among other values. PLG copolymers with varying lactide:glycolide ratios, molecular weights and end groups are readily available commercially from a number of sources including from Boehringer Ingelheim, Germany, Birmingham Polymers, Inc., Birmingham, Ala., USA and Lakeshore Biomaterials, Birmingham, Ala., USA. Some exemplary PLG copolymers, available from Boehringer Ingelheim, include: (a) RG 502, a PLG having predominantly alkyl ester end groups on one of the chain ends, a 50:50 lactide/glycolide molar ratio and a molecular weight of 12,000 Da, (b) RG 503, a PLG having predominantly alkyl ester end groups on one of the chain ends, a 50:50 lactide/glycolide molar ratio and a molecular weight of 34,000 Da, (c) RG 504, a PLG having predominantly alkyl ester end groups on one of the chain ends, a 50:50 lactide/glycolide molar ratio and a molecular weight of 48,000 Da, (d) RG 752, a PLG having predominantly alkyl ester end groups on one of the chain ends, a 75:25 lactide/glycolide molar ratio and a molecular weight of 22,000 Da, (e) RG 755, a PLG having predominantly alkyl ester end groups on one of the chain ends, a 75:25 lactide/glycolide molar ratio and a molecular weight of 68,000 Da, (f) RG 502H, a PLG having a 50:50 lactide/glycolide molar ratio, and having predominantly free carboxyl end groups on one of the chain ends, and (g) RG 503H, a PLG having a 50:50 lactide/glycolide molar ratio, and having predominantly free carboxyl end groups on one of the chain ends.

In addition to free carboxyl and alkyl ester end groups, PLG may also be provided with amine, hydroxyl, thiol, succinimidyl ester or maleimide groups, among others, on at least one of the chain ends.

In certain embodiments charged polymeric particles may be formed using a charged biodegradable polymer, examples of which include positively charged peptides and proteins, including histone peptides and homopolymer and copolymers containing basic amino acids such as lysine, arginine, ornithine and combinations thereof, gelatin, protamine and protamine sulfate, spermine, spermidine, hexadimethrene bromide (polybrene), and polycationic polysaccharides such as cationic starch and chitosan, among various others.

In preferred embodiments, however, polymeric particles are formed from a substantially non-charged polymer (e.g., selected from those described above) in the presence of a charged species or subsequently treated with a charged species. Examples of such charged species include ionic small molecules, ionic peptides, ionic polymers and ionic surfactants, among others.

Such species may be provided, for example, in an amount effective to promote acceptable particle suspension (e.g., during particle formation and/or resuspension after lyophilization).

Such species may also be provided, for example, in an amount effective to promote adsorption of species to the surfaces of the particles (e.g., polynucleotides including vector constructs that lead to expression of antigens, antigens, immunological adjuvants, etc.). For example, in various embodiments of the invention, particles having a net positive charge may be employed to enhance RNA replicon adsorption.

The net charge of a given particle population may be measured using known techniques including measurement of the particle zeta potential. In certain embodiments, positively charged polymeric particle suspensions are produced which have a zeta potential that is greater than +20 mV. Such suspensions can be used to adsorb positively charged species such as polynucleotides (e.g., vector constructs leading to the expression of antigens, such as RNA replicons), antigens, immunological adjuvants, and so forth.

In certain embodiments, cationic surfactants are provided to impart charge to the particles. Examples of cationic surfactants include, for example, the following, among others: benzalkonium chloride, cetyl-trimethylammonium bromide (CTAB), dimethyldioctadecylammonium bromide (DDA), 3-beta-[N—(N',N'-dimethylaminoethane) carbamoyl]cholesterol (DC-Chol), 3-beta-[N—(N',N',N'-trimethylaminoethane) carbamoyl]cholesterol (TC-Chol), 4-(2-aminoethyl)-morpholino-cholesterol hemisuccinate (MoChol), histaminyl-cholesterol hemisuccinate (H is Chol), (1,2-dioleoyloxypropyl)-N,N,N-trimethylammonium salt (DOTAP), (1,2-dimyristoyloxypropyl)-N,N,N-trimethylammonium salt (DMTAP), (1,2-dipalmitoyloxypropyl)-N,N,N-trimethylammonium salt (DPTAP), (1,2-dioleoyloxypropyl)-N,N-dimethylammonium salt (DODAP), (1,2-dioleyloxypropyl)-3-dimethylhydroxyethyl ammonium bromide (DORIE), 1,2-dioleoyl-sn-glycero-3-ethylphosphocholine (DOEPC), 1,2-dipalmitoyl-sn-glycero-3-ethylphosphocholine (DPEPC), 1,2-distearoyl-sn glycerol-3-ethylphosphocholine (DSEPC), 1,2-dimyristoyl-sn-glycero-3-ethylphophocholine (DMEPC), 1,2-dilauroyl-sn-glycero-3-ethylphosphocholine (DLEPC), cetyl-pyridinium chloride (CPyC), histaminyl-cholesterol carbamate (CHIM), (1,2-dioleyloxypropyl)-N,N,N-trimethylammoniun chloride (DOTMA), N,N-dioctadecylamido-glycyl-spermine (DOGS),4-(2,3-bis-palmitoyloxy-propyl)-1-methyl-1H-imidazole (DPIM), their structural variants and derivatives, and combinations thereof.

Any suitable cationic surfactant may be used. Suitable cationic surfactants include, benzalkonium chloride (BAK), benzethonium chloride, cetramide (which contains tetradecyltrimethylammonium bromide and possibly small amounts of dedecyltrimethylammonium bromide and hexadecyltrimethyl ammonium bromide), cetylpyridinium chloride (CPC), cetyl trimethylammonium chloride (CTAC), primary amines, secondary amines, tertiary amines, including but not limited to N,N',N'-polyoxyethylene (10)-N-tallow-1,3-diaminopropane, other quaternary amine salts, including but not limited to dodecyltrimethylammonium bromide, hexadecyltrimethyl-ammonium bromide, mixed alkyl-trimethyl-ammonium bromide, benzyldimethyldodecylammonium chloride, benzyldimethylhexadecyl-ammonium chloride, benzyltrimethylammonium methoxide, cetyldimethylethylammonium bromide, dimethyldioctadecyl ammonium bromide (DDAB), methylbenzethonium chloride, decamethonium chloride, methyl mixed trialkyl ammonium chloride, methyl trioctylammonium chloride), N,N-dimethyl-N-[2 (2-methyl-4-(1,1,3,3tetramethylbutyl)-phenoxy]-ethoxy)ethyl]-benzenemetha-naminium chloride (DEBDA), dialkyldimethylammonium salts, [1-(2,3-dioleyloxy)-propyl]-N,N,N,trimethylammonium chloride, 1,2-diacyl-3-(trimethylammonio) propane (acyl group=dimyristoyl, dipalmitoyl, distearoyl, dioleoyl), 1,2-diacyl-3 (dimethylammonio) propane (acyl group=dimyristoyl, dipalmitoyl, distearoyl, dioleoyl), 1,2-dioleoyl-3-(4'-trimethyl-ammonio)butanoyl-sn-glycerol, 1,2-dioleoyl 3-succinyl-sn-glycerol choline ester, cholesteryl (4'-trimethylammonio) butanoate), N-alkyl pyridinium salts (e.g. cetylpyridinium bromide and cetylpyridinium chloride), N-alkylpiperidinium salts, dicationic bolaform electrolytes ($C_{12}Me_6$; $C_{12}B_{U6}$), dialkylglycetylphosphorylcholine, lysolecithin, L-α dioleoylphosphatidylethanolamine, cholesterol hemisuccinate choline ester, lipopolyamines, including but not limited to dioctadecylamidoglycylspermine (DOGS), dipalmitoyl phosphatidylethanol-amidospermine (DPPES), lipopoly-L (or D)-lysine (LPLL, LPDL), poly (L (or D)-lysine conjugated to N— glutarylphosphatidylethanolamine, didodecyl glutamate ester with pendant amino group (CˆG1uPhCnN), ditetradecyl glutamate ester with pendant amino group ($Cl_4GluCnN^+$), cationic derivatives of cholesterol, including but not limited to cholesteryl-3 β-oxysuccinamidoethylenetrimethylammonium salt, cholesteryl-3 β-oxysuccinamidoethylenedimethylamine, cholesteryl-3 β-carboxyamidoethylenetrimethylammonium salt, cholesteryl-3 β-carboxyamidoethylenedimethylamine, and 3γ-[N—(N',N-dimethylaminoetanecarbomoyl]cholesterol) (DC-Cholesterol), 1,2-dioleoyloxy-3-(trimethylammonio)propane (DOTAP), dimethyldioctadecylammonium (DDA), 1,2-Dimyristoyl-3-TrimethylAmmoniumPropane (DMTAP), dipalmitoyl($C_{16:0}$)trimethyl ammonium propane (DPTAP), distearoyltrimethylammonium propane (DSTAP), and combination thereof.

Other cationic surfactants include, e.g., the cationic lipids described in U.S. Patent Publications 2008/0085870 (published Apr. 10, 2008) and 2008/0057080 (published Mar. 6, 2008).

In preferred embodiments, the cationic surfactant is selected from the group consisting of 1,2-dioleoyloxy-3-(trimethylammonio)propane (DOTAP), 3β-[N—(N',N'-Dimethylaminoethane)-carbamoyl]Cholesterol (DC Cholesterol), dimethyldioctadecylammonium (DDA), 1,2-Dimyristoyl-3-TrimethylAmmoniumPropane (DMTAP), dipalmitoyl($C_{16:0}$-trimethyl ammonium propane (DPTAP), distearoyltrimethylammonium propane (DSTAP), and combinations thereof.

In this regard, various salt forms of the preceding cationic surfactants may be provided including halide and hydrohalide salts such as chloride, bromide, iodide, hydrochloride, and so forth. Where a particular salt is listed (e.g., chloride), it is to be understood that other salts (e.g., bromide, iodide, etc.) may be employed as well.

In certain embodiments, the cationic surfactant comprises an ammonium group and one or more saturated or unsaturated hydrocarbon chains having between 12 to 20 carbon atoms, specific examples of which include DDA,

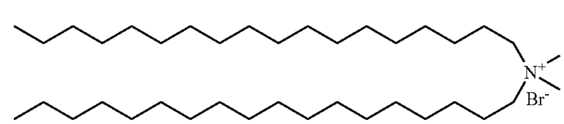

, and DOTAP,

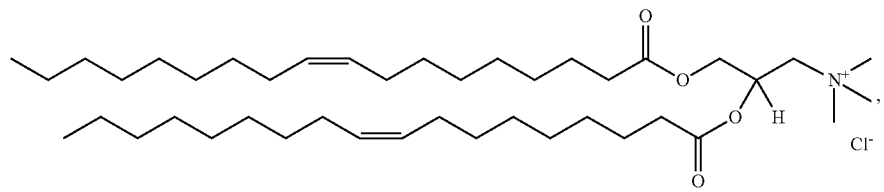 [SMILES: CCCCCCCC/C=C\CCCCCCCC(=O)OCC(C[N+](C)(C)C)OC(=O)CCCCCCC/C=C\CCCCCCCC ; [Cl-]]

among others.

Various methods may be employed to produce polymeric particles in accordance with the invention.

For example, in some embodiments, polymeric particles can be formed using spray-drying and coacervation as described in, e.g., Thomasin et al., *J. Controlled Release* (1996) 41:131; U.S. Pat. No. 2,800,457; Masters, K. (1976) *Spray Drying* 2nd Ed. Wiley, New York; air-suspension coating techniques, such as pan coating and Wurster coating, as described by Hall et al., (1980) The "Wurster Process" in *Controlled Release Technologies: Methods, Theory, and Applications* (A. F. Kydonieus, ed.), Vol. 2, pp. 133-154 CRC Press, Boca Raton, Fla. and Deasy, P. B., *Crit. Rev. Ther. Drug Carrier Syst.* (1988) S(2):99-139; and ionic gelation as described by, e.g., Lim et al., *Science* (1980) 210:908-910.

In some embodiments, particles may be formed using an oil-in-water (o/w) or water-in-oil-in-water (w/o/w) solvent evaporation process or using a nanoprecipitation method.

The w/o/w solvent evaporation process is described, for example, in O'Hagan et al., *Vaccine* (1993) 11:965-969, Jeffery et al., *Pharm. Res.* (1993) 10:362, and WO 00/06123. In general, a polymer of interest, such as PLG, is dissolved in an organic solvent, such as dimethylchloride (also called methylene chloride and dichloromethane), ethyl acetate, acetonitrile, acetone, chloroform, and the like, to form an organic solution. The organic solution is then combined with a first volume of aqueous solution and emulsified to form a water-in-oil emulsion. The aqueous solution can be, for example, deionized water, normal saline, a buffered solution, for example, phosphate-buffered saline (PBS) or a sodium citrate/ethylenediaminetetraacetic acid (sodium citrate/ETDA) buffer solution, among others. Typically, the volume ratio of polymer solution to aqueous solution ranges from about 5:1 to about 20:1, more typically about 10:1. Emulsification is conducted using any equipment appropriate for this task, and is typically a high-shear device such as, e.g., a homogenizer. A volume of the water-in-oil emulsion is then combined with a larger second volume of an aqueous solution, which typically contains a surfactant, for instance, an uncharged surfactant (e.g., PVA (polyvinyl alcohol), povidone (also known as polyvinylpyrrolidone or PVP), sorbitan esters, polysorbates, polyoxyethylated glycol monoethers, polyoxyethylated alkyl phenols, or poloxamers, among others) or a cationic surfactant (e.g., selected from those listed above, among others). The volume ratio of aqueous solution to the water-in-oil emulsion typically ranges from about 2:1 to 10:1, more typically about 4:1. This mixture is then homogenized to produce a stable w/o/w double emulsion. Organic solvents are then evaporated to yield particles. Particles manufactured with cationic polymers and those manufactured in the presence of cationic surfactants generally have a surface having a net positive charge, which can adsorb a wide variety of negatively charged molecules.

The oil-in-water (o/w) solvent evaporation process is similar to the w/o/w solvent evaporation process described in the prior paragraph. In general, a polymer of interest, such as PLG, is dissolved in an organic solvent, such as dimethylchloride (also called methylene chloride and dichloromethane), ethyl acetate, acetonitrile, acetone, chloroform, 2,2,2-trifluoroethanol, dimethyl sulfoxide and the like, to form an organic solution. In certain embodiments of the invention, the polymer is added to the organic solvent in an amount ranging from 2 to 20% w/v (e.g., ranging from 2 to 5 to 10 to 15 to 20% w/v), more typically from 5 to 15% w/v relative to the solvent. In certain embodiments of the invention, the organic solution comprises a cationic surfactant, typically in an amount ranging from 0.2 to 20% w/w (e.g., ranging from 0.2 to 0.5 to 1 to 2 to 5 to 10 to 15 to 20% w/w) relative to the polymer, more typically 1% to 10% w/w relative to the polymer. The organic solution is then combined with a volume of aqueous solution and emulsified to form an o/w emulsion. The aqueous solution can be, for example, water for injection, deionized water, normal saline, a buffered solution, for example, phosphate-buffered saline (PBS) or a sodium citrate/ethylenediaminetetraacetic acid (sodium citrate/ETDA) buffer solution, among others. The aqueous solution may contain a surfactant, for instance, an uncharged surfactant or a cationic surfactant (as an alternative or in addition to any cationic surfactant included in the organic phase). Typically, the volume ratio of the aqueous solution to the polymer solution ranges from about 1:1 to about 25:1, more typically about 4:1. Emulsification is conducted using any equipment appropriate for this task, and is typically a high-shear device such as, e.g., a homogenizer. Organic solvents are then evaporated to yield particles. As above, particles manufactured with cationic polymers and those manufactured in the presence of cationic surfactants generally have a surface having a net positive charge, which can adsorb a wide variety of negatively charged molecules.

The nanoprecipitation method, also referred to as the solvent displacement method, is another example of a suitable method for forming particles for use in the invention. See, e.g., European Patent No. 0274961B1 entitled "Process for the preparation of dispersible colloidal systems of a substance in the form of nanocapsules," Devissaguet et al., U.S. Pat. No. 5,049,322 by the same title, Fessi et al., U.S. Pat. No. 5,118,528, entitled "Process for the preparation of dispersible colloidal systems of a substance in the form of microparticles," and Wendorf et al., WO 2008/051245, entitled "Nanoparticles for use in Immunogenic compositions." In this technique, for instance, a polymer may be dissolved in an organic solvent (e.g., a hydrophilic organic solvent such as acetone, ethanol, etc.). In certain embodiments of the invention, the polymer is added to the organic solvent in an amount ranging form 0.1 to 5% w/v (e.g., ranging from 0.1 to 0.2 to 0.5 to 1 to 2 to 5% w/v) relative to the solvent. In certain embodiments of the invention, the organic solution comprises a cationic surfactant, typically in an amount ranging from 1% to 10% w/w (e.g., ranging from 1 to 2 to 5 to 10% w/w) relative to the polymer. The resulting organic solution may then be combined with a further solvent, which is miscible with the organic solvent while being a non-solvent for the polymer, typically an aqueous solution. The aqueous solution can be, for example, deionized water, normal saline, a buffered solution, such as for example, phosphate-buffered saline (PBS) or a sodium citrate/ethylenediaminetetraacetic acid (sodium citrate/EDTA) buffer solution. The organic solution and aqueous solution may then be combined in suitable relative volumes, typically from 1:5 to 5:1 (e.g., from 1:5 to 1:2.5 to 1:1 to 2.5:1 to 5:1), more typically about 1:1. For example, the organic solution may be poured, injected dripped into the non-solvent while stirring or homogenizing or shaking, or vice versa. By selecting a system in which the polymer is soluble in the organic solvent, while being significantly less soluble in the miscible blend of the organic solvent with the non-solvent, a suspension of particles may be formed virtually instantaneously. Subsequently, the organic solvent can be eliminated from the suspension, for example, by evaporation.

As above, particles manufactured with cationic polymers and those manufactured in the presence of cationic surfactants generally have a surface having a net positive charge, which can adsorb a wide variety of negatively charged molecules.

As previously indicated, in certain embodiments, it is desirable to provide one or more additional species (in addition to polymer), which may be associated with the interior (e.g., entrapped) and/or surface (e.g. by adsorption, covalent attachment, co-lyophilization, etc.) of the particles or may be non-associated with the particles. Such additional species can include, for instance, agents to adjust tonicity or pH, cryoprotective agents, immunological adjuvants, antigens, RNA replicons, and so forth.

Such additional species may be provided during the particle formation process. In the above described particle formation techniques (e.g., w/o/w solvent evaporation, o/w solvent evaporation, nanoprecipitation, etc.), the organic and/or aqueous solutions employed can thus further contain various additional species as desired. For example, these additional species may be added (a) to an organic solution, if in oil-soluble or oil-dispersible form or (b) to an aqueous solution, if in water-soluble or water-dispersible form.

In some embodiments, one or more additional species may be added subsequent to particle formation (typically subsequent to organic solvent removal, as well as subsequent to washing steps or steps in which the particles are dialyzed against water, if any). These additional species are frequently added to the particles as an aqueous solution or dispersion. These species can, for instance, be in solution and/or accumulate at the particle-solution interface, for example, being adsorbed at the particle surface.

Once a suitable composition is formed (e.g., using the above-described or other techniques), it may be lyophilized for future use.

2. RNA Replicons

An immunogenic composition of the invention can include an RNA replicon comprising at least one polynucleotide encoding at least one antigen. The RNA replicon is capable of directing its own amplification or self-replication in vivo, typically within a target cell.

A replicon can, when delivered to a vertebrate cell even without any proteins, lead to the production of multiple daughter RNAs by transcription from itself (via an antisense copy which it generates from itself). A self-replicating RNA molecule is thus typically a +-strand molecule which can be directly translated after delivery to a cell, and this translation provides a RNA-dependent RNA polymerase which then produces both antisense and sense transcripts from the delivered RNA. Thus the delivered RNA leads to the production of multiple daughter RNAs.

These daughter RNAs, as well as collinear subgenomic transcripts, may be translated themselves to provide in situ expression of an encoded antigen, or may be transcribed to provide further transcripts with the same sense as the delivered RNA which are translated to provide in situ expression of the antigen. The overall results of this sequence of transcriptions are a huge amplification in the number of the introduced replicon RNAs and so the encoded antigen becomes a major polypeptide product of the cells.

One suitable system for achieving self-replication in this manner is to use an alphavirus-based replicon. Suitable alphaviruses are listed above. Alphavirus replicons are +-stranded RNAs which lead to translation of a replicase (or replicase-transcriptase) after delivery to a cell. The replicase is translated as a polyprotein which auto-cleaves to provide a replication complex which creates genomic --strand copies of the +-strand delivered RNA. These --strand transcripts can themselves be transcribed to give further copies of the +-stranded parent RNA and also to give a subgenomic transcript which encodes the antigen. Translation of the subgenomic transcript thus leads to in situ expression of the antigen by the infected cell. Suitable alphavirus replicons can use a replicase from a Sindbis virus, a Semliki forest virus, an eastern equine encephalitis virus, a Venezuelan equine encephalitis virus, etc.

A preferred replicon thus encodes (i) a RNA-dependent RNA polymerase which can transcribe RNA from the replicon and (ii) an antigen. The polymerase can be an alphavirus replicase e.g. comprising one or more of alphavirus proteins nsP1, nsP2, nsP3 and nsP4. Whereas natural alphavirus genomes encode structural virion proteins in addition to the non-structural replicase polyprotein, it is preferred that the replicon does not encode alphavirus structural proteins. Thus a preferred replicon can lead to the production of genomic RNA copies of itself in a cell, but not to the production of RNA-containing virions. The inability to produce these virions means that, unlike a wild-type alphavirus, the preferred replicon cannot perpetuate itself in infectious form. The alphavirus structural proteins which are necessary for perpetuation in wild-type viruses are absent from the preferred replicon and their place is taken by gene(s) encoding the antigen of interest, such that the subgenomic transcript encodes the antigen rather than the structural alphavirus virion proteins.

Thus a replicon useful with the invention may have two open reading frames. The first (5') open reading frame encodes a replicase; the second (3') open reading frame encodes an antigen. In some embodiments the RNA may have additional (e.g. downstream) open reading frames e.g. to encode further antigens (see below) or to encode accessory polypeptides.

A preferred replicon has a 5' cap (e.g. a 7-methylguanosine). This cap can enhance in vivo translation of the RNA. In some embodiments the 5' sequence of the replicon must be selected to ensure compatibility with the encoded replicase.

A replicon may have a 3' poly-A tail. It may also include a poly-A polymerase recognition sequence (e.g. AAUAAA) near its 3' end.

Replicons can have various lengths but they are typically 5000-25000 nucleotides long e.g. 8000-15000 nucleotides, or 9000-12000 nucleotides.

Replicons are typically single-stranded. Single-stranded RNAs can generally initiate an adjuvant effect by binding to TLR7, TLR8, RNA helicases and/or PKR. RNA delivered in double-stranded form (dsRNA) can bind to TLR3, and this receptor can also be triggered by dsRNA which is formed either during replication of a single-stranded RNA or within the secondary structure of a single-stranded RNA.

The replicon can conveniently be prepared by in vitro transcription (IVT). IVT can use a (cDNA) template created and propagated in plasmid form in bacteria, or created synthetically (for example by gene synthesis and/or polymerase chain-reaction (PCR) engineering methods). For instance, a DNA-dependent RNA polymerase (such as the bacteriophage T7, T3 or SP6 RNA polymerases) can be used to transcribe the replicon from a DNA template. Appropriate capping and poly-A addition reactions can be used as required (although the replicon's poly-A is usually encoded within the DNA template). These RNA polymerases can have stringent requirements for the transcribed 5' nucleotide(s) and in some embodiments these requirements must be matched with the requirements of the encoded replicase, to ensure that the IVT-transcribed RNA can function efficiently as a substrate for its self-encoded replicase.

As discussed in U.S. Ser. No. 61/223,347 (and an international patent application filed 6 Jul. 2010 claiming priority therefrom), the replicon can include (in addition to any 5' cap structure) one or more nucleotides having a modified nucleobase. Thus the replicon can comprise m5C (5-methylcytidine), m5U (5-methyluridine), m6A (N6-methyladenosine), s2U (2-thiouridine), Um (2'-O-methyluridine), ml A (1-methyl adenosine); m2A (2-methyladenosine); Am (2'-O-methyladenosine); ms2 m6A (2-methylthio-N6-methyladenosine); i6A (N6-isopentenyladenosine); ms2i6A (2-methylthio-N6 isopentenyladenosine); io6A (N6-(cis-hydroxyisopentenyl)adenosine); ms2io6A (2-methylthio-N6-(cis-hydroxyisopentenyl) adenosine); g6A (N6-glycinylcarbamoyladenosine); t6A (N6-threonyl carbamoyladenosine); ms2t6A (2-methylthio-N6-threonyl carbamoyladenosine); m6t6A (N6-methyl-N6-threonylcarbamoyladenosine); hn6A (N6.-hydroxynorvalylcarbamoyl adenosine); ms2hn6A (2-methylthio-N6-hydroxynorvalyl carbamoyladenosine); Ar(p) (2'-O-ribosyladenosine (phosphate)); I (inosine); m1I (1-methylinosine); m'Im (1,2'-O-dimethylinosine); m3C (3-methylcytidine); Cm (2T-O-methylcytidine); s2C (2-thiocytidine); ac4C(N4-acetylcytidine); f5C (5-formylcytidine); m5 Cm (5,2-O-dimethyl cytidine); ac4 Cm (N4acetyl2TOmethylcytidine); k2C (lysidine); ml G (1-methylguanosine); m2G (N2-methylguanosine); m7G (7-methylguanosine); Gm (2'-O-methylguanosine); m22G (N2,N2-dimethylguanosine); m2Gm (N2,2'-β-dimethylguanosine); m22Gm (N2,N2,2'-O-trimethylguanosine); Gr(p) (2'-β-ribosylguanosine (phosphate)); yW (wybutosine); o2yW (peroxywybutosine); OHyW (hydroxywybutosine); OHyW* (undermodified hydroxywybutosine); imG (wyosine); mimG (methylguanosine); Q (queuosine); oQ (epoxyqueuosine); galQ (galtactosyl-queuosine); manQ (mannosyl-queuosine); preQo (7-cyano-7-deazaguanosine); preQi (7-aminomethyl-7-deazaguanosine); G (archaeosine); D (dihydrouridine); m5Um (5,2'-O-dimethyluridine); s4U (4-thiouridine); m5s2U (5-methyl-2-thiouridine); s2Um (2-thio-2'-O-methyluridine); acp3U (3-(3-amino-3-carboxypropyl)uridine); ho5U (5-hydroxyuridine); mo5U (5-methoxyuridine); cmo5U (uridine 5-oxyacetic acid); mcmo5U (uridine 5-oxyacetic acid methyl ester); chm5U (5-(carboxyhydroxymethyl)uridine)); mchm5U (5-(carboxyhydroxymethyl)uridine methyl ester); mcm5U (5-methoxycarbonyl methyluridine); mcm5Um (S-methoxycarbonylmethyl-2-O-methyluricjine); mcm5s2U (5-methoxycarbonylmethyl-2-thiouridine); nm5s2U (5-aminomethyl-2-thiouridine); mnm5U (5-methylaminomethyluridine); mnm5s2U (5-methylaminomethyl-2-thiouridine); mnm5se2U (5-methylaminomethyl-2-selenouridine); ncm5U (5-carbamoylmethyl uridine); ncm5Um (5-carbamoylmethyl-2'-O-methyluridine); cmnm5U (5-carboxymethylaminomethyluridine); cnmm5Um (5-carboxymethylaminomethyl-2-L-Omethyluridine); cmnm5s2U (5-carboxymethylaminomethyl-2-thiouridine); m62A (N6,N6-dimethyladenosine); Tm (2'-β-methylinosine); m4C (N4-methylcytidine); m4 Cm (N4,2-O-dimethylcytidine); hm5C (5-hydroxymethylcytidine); m3U (3-methyluridine); cm5U (5-carboxymethyluridine); m6 Am (N6,T-O-dimethyladenosine); rn62 Am (N6,N6,O-2-trimethyladenosine); m2'7G (N2,7-dimethylguanosine); m2'2'7G (N2,N2,7-trimethylguanosine); m3Um (3,2T-O-dimethyluridine); m5D (5-methyldihydrouridine); f5 Cm (5-formyl-2'-O-methylcytidine); m1Gm (1,2'-O-dimethylguanosine); m'Am (1,2-O-dimethyl adenosine) irinomethyluridine); tm5s2U (S-taurinomethyl-2-thiouridine)); imG-14 (4-demethyl guanosine); imG2 (isoguanosine); or ac6A (N6-acetyladenosine), hypoxanthine, inosine, 8-oxo-adenine, 7-substituted derivatives thereof, dihydrouracil, pseudouracil, 2-thiouracil, 4-thiouracil, 5-aminouracil, 5-(C1-C6)-alkyluracil, 5-methyluracil, 5-(C2-C6)-alkenyluracil, 5-(C2-C6)-alkynyluracil, 5-(hydroxymethyl)uracil, 5-chlorouracil, 5-fluorouracil, 5-bromouracil, 5-hydroxycytosine, 5-(C1-C6)-alkylcytosine, 5-methylcytosine, 5-(C2-C6)-alkenylcytosine, 5-(C2-C6)-alkynylcytosine, 5-chlorocytosine, 5-fluorocytosine, 5-bromocytosine, N2-dimethylguanine, 7-deazaguanine, 8-azaguanine, 7-deaza-7-substituted guanine, 7-deaza-7-(C2-C6)alkynylguanine, 7-deaza-8-substituted guanine, 8-hydroxyguanine, 6-thioguanine, 8-oxoguanine, 2-aminopurine, 2-amino-6-chloropurine, 2,4-diaminopurine, 2,6-diaminopurine, 8-azapurine, substituted 7-deazapurine, 7-deaza-7-substituted purine, 7-deaza-8-substituted purine, or an abasic nucleotide. For instance, a replicon can include one or more modified pyrimidine nucleobases, such as pseudouridine and/or 5-methylcytosine residues. In some embodiments, however, the replicon includes no modified nucleobases, and may include no modified nucleotides i.e. all of the nucleotides in the RNA are standard A, C, G and U ribonucleotides (except for any 5' cap structure, which may include a 7'-methylguanosine). In other embodiments, the replicon may include a 5' cap comprising a 7'-methylguanosine, and the first 1, 2 or 3 5' ribonucleotides may be methylated at the 2' position of the ribose.

In certain embodiments, the amount of RNA replicon in the particle compositions of the present invention may range from 0.01% to 1% (e.g., ranging from 0.01% to 0.025% to 0.05% to 1%) relative to the weight of biodegradable polymer within the composition, among other values. The precise amount will generally depend upon the N:P ratio that is selected and upon loading of cationic surfactant in the particles.

In certain embodiments, the amount of RNA replicon in the particle compositions of the present invention is dictated by the amount of cationic surfactant in the composition. This may be expressed as the "N:P ratio" which is defined herein as the ratio of the number of moles of cationic nitrogen in the cationic surfactant to the number of moles of anionic phosphate in the RNA replicon.

For example, the N:P ratio employed in the compositions of the invention may range from 100:1 to 1:100, among others values, instance, ranging from 100:1 to 80:1 to 60:1 to 50:1 to 40:1 to 30:1 to 25:1 to 20:1 to 15:1 to 12.5:1 to 10:1 to 8:1 to 6:1 to 5:1 to 4:1 to 3:1 to 2.5:1 to 2:1 to 1.5:1 to 1.25:1 to 1:1 to 1:1.25 to 1:2 to 1:2.5 to 1:3 to 1:4 to 1:5 to 1:6 to 1:8 to 1:10 to 1:12.5 to 1:15 to 1:20 to 1:25 to 1:30 to 1:40 to 1:50 to 1:60 to 1:80 to 1:100.

3. Antigens

Particle compositions in accordance with the invention include self-replicating RNA molecules encoding an antigen. After administration of the particles the antigen is translated in vivo and can elicit an immune response in the recipient. The antigen may elicit an immune response against a bacterium, a virus, a fungus or a parasite (or, in some embodiments, against an allergen, and in other embodiments against a tumor antigen). The immune response may comprise an antibody response (usually including IgG) and/or a cell-mediated immune response. The antigen will typically elicit an immune response which recognizes the corresponding bacterial, viral, fungal or parasite (or allergan or tumor) polypeptide, but in some embodiments the antigen may act as a mimotope to elicit an immune response which recognises a bacterial, viral, fungal or parasite saccharide. The antigen will typically be a surface polypeptide e.g. an adhesin, a hemagglutinin, an envelope glycoprotein, a spike glycoprotein, etc.

Self-replicating RNA molecules can encode a single antigen or multiple antigens. Multiple antigens can be presented as a single polypeptide antigen (fusion polypeptide) or as separate polypeptides. If antigens are expressed as separate polypeptides then one or more of these may be provided with an upstream IRES or an additional viral promoter element. Alternatively, multiple antigens may be expressed from a polyprotein that encodes individual antigens fused to a short autocatalytic protease (e.g. foot-and-mouth disease virus 2A protein), or as inteins.

Antigens produced by self-replicating RNA molecules in the compositions of the invention include, but are not limited to, one or more of the antigens set forth below, and antigens derived from one or more of the pathogens and tumors set forth below.

In certain embodiments, in addition to self-replicating RNA molecules that express antigens, the compositions of the invention may further comprise antigens per se (e.g., protein antigens, polysaccharide antigens, protein-polysaccharide conjugate antigens, etc.), for example, one or more of the antigens set forth below, and antigens derived from one or more of the pathogens and tumors set forth below. Where antigens per se are included, typical wt/wt ratios of antigen to polymer(s) in the compositions of the present invention range from 0.0005:1 to 10:1 by weight, among other possibilities, for example, ranging from 0.0005:1 to 0.10:1 (e.g., ranging from 0.0005:1 to 0.001:1 to 0.0025:1 to 0.005:1 to 0.01:1 to 0.025:1 to 0.05:1 to 0.10:1), more typically ranging from 0.001:1 to 0.05:1.

Viral Antigens

Viral antigens suitable for use herein include, but are not limited to, proteins and peptides from a virus. In some embodiments the antigen elicits an immune response against one of these viruses:

Orthomyxovirus: Viral antigens include, but are not limited to, those from an influenza A, B or C virus, such as the hemagglutinin, neuraminidase or matrix M2 proteins. Where the immunogen is an influenza A virus hemagglutinin it may be from any subtype e.g. H1, H2, H3, H4, H5, H6, H7, H8, H9, H10, H11, H12, H13, H14, H15 or H16.

Paramyxoviridae viruses: Viral antigens include, but are not limited to, those derived from Paramyxoviridae viruses, such as those derived from Pneumoviruses (e.g. respiratory syncytial virus, RSV), Rubulaviruses (e.g. mumps virus), Paramyxoviruses (e.g. parainfluenza virus), Metapneumoviruses and Morbilliviruses (e.g. measles).

Pneumovirus: Viral antigens include, but are not limited to, those derived from a Pneumovirus, such as Respiratory syncytial virus (RSV), Bovine respiratory syncytial virus, Pneumonia virus of mice, and Turkey rhinotracheitis virus. In certain embodiments, pneumovirus antigens are selected from one or more of the following proteins, including surface proteins Fusion (F), Glycoprotein (G) and Small Hydrophobic protein (SH), matrix proteins M and M2, nucleocapsid proteins N, P and L and nonstructural proteins NS1 and NS2. In other embodiments, pneumovirus antigens include F, G and M. In certain embodiments, pneumovirus antigens are also derived from chimeric viruses, such as, by way of example only, chimeric RSV/PIV viruses comprising components of both RSV and PIV.

Paramyxovirus: Viral antigens include, but are not limited to, those derived from a Paramyxovirus, such as Parainfluenza virus types 1-4 (PIV), Mumps, Sendai viruses, Simian virus 5, Bovine parainfluenza virus, Nipahvirus, Henipavirus and Newcastle disease virus. In certain embodiments, the Paramyxovirus is PIV or Mumps. In certain embodiments, paramyxovirus antigens are selected from one or more of the following proteins: Hemagglutinin—Neuraminidase (HN), Fusion proteins F1 and F2, Nucleoprotein (NP), Phosphoprotein (P), Large protein (L), and Matrix protein (M). In other embodiments, paramyxovirus proteins include HN, F1 and F2. In certain embodiments, paramyxovirus antigens are derived from chimeric viruses, such as, by way of example only, chimeric RSV/PIV viruses comprising components of both RSV and PIV. In other embodiments, the Paramyxovirus is Nipahvirus or Henipavirus and the anitgens are selected from one or more of the following proteins: Fusion (F) protein, Glycoprotein (G) protein, Matrix (M) protein, Nucleocapsid (N) protein, Large (L) protein and Phosphoprotein (P).

Poxyiridae: Viral antigens include, but are not limited to, those derived from Orthopoxvirus such as Variola vera, including but not limited to, Variola major and Variola minor.

Metapneumovirus: Viral antigens include, but are not limited to, Metapneumovirus, such as human metapneumovirus (hMPV) and avian metapneumoviruses (aMPV). In certain embodiments, metapneumovirus antigens are selected from one or more of the following proteins, including surface proteins Fusion (F), Glycoprotein (G) and Small Hydrophobic protein (SH), matrix proteins M and M2, nucleocapsid proteins N, P and L. In other embodiments, metapneumovirus antigens include F, G and M. In certain embodiments, metapneumovirus antigens are derived from chimeric viruses.

Morbillivirus: Viral antigens include, but are not limited to, those derived from a Morbillivirus, such as Measles. In certain embodiments, morbillivirus antigens are selected from one or more of the following proteins: hemagglutinin (H), Glycoprotein (G), Fusion factor (F), Large protein (L), Nucleoprotein (NP), Polymerase phosphoprotein (P), and Matrix (M).

Picornavirus: Viral antigens include, but are not limited to, those derived from Picornaviruses, such as Enteroviruses, Rhinoviruses, Heparnavirus, Parechovirus, Cardioviruses and Aphthoviruses. In certain embodiments, the antigens are derived from Enteroviruses, while in other embodiments the enterovirus is Poliovirus. In still other embodiments, the antigens are derived from Rhinoviruses.

Enterovirus: Viral antigens include, but are not limited to, those derived from an Enterovirus, such as Poliovirus types 1, 2 or 3, Coxsackie A virus types 1 to 22 and 24, Coxsackie B virus types 1 to 6, Echovirus (ECHO) virus) types 1 to 9, 11 to 27 and 29 to 34 and Enterovirus 68 to 71. In certain embodiments, the enterovirus antigens are selected from one or more of the following Capsid proteins VP0, VP1, VP2, VP3 and VP4. In another embodiment, the enterovirus is an EV71 enterovirus. In another embodiment, the enterovirus is a coxsackie A or B virus.

Bunyavirus: Viral antigens include, but are not limited to, those derived from an Orthobunyavirus, such as California encephalitis virus, a Phlebovirus, such as Rift Valley Fever virus, or a Nairovirus, such as Crimean-Congo hemorrhagic fever virus.

Rhinovirus: Viral antigens include, but are not limted to, those derived from rhinovirus. In certain embodiments, the rhinovirus antigens are selected from one or more of the following Capsid proteins: VP0, VP1, VP2, VP2 and VP4.

Heparnavirus: Viral antigens include, but are not limited to, those derived from a Heparnavirus, such as, by way of example only, Hepatitis A virus (HAV).

Filovirus: Viral immunogens include, but are not limited to, those derived from a filovirus, such as an Ebola virus (including a Zaire, Ivory Coast, Reston or Sudan ebolavirus) or a Marburg virus.

Togavirus: Viral antigens include, but are not limited to, those derived from a Togavirus, such as a Rubivirus, an Alphavirus, or an Arterivirus. In certain embodiments, the antigens are derived from Rubivirus, such as by way of example only, Rubella virus. In certain embodiments, the togavirus antigens are selected from E1, E2, E3, C, NSP-1, NSPO-2, NSP-3 or NSP-4. In certain embodiments, the togavirus antigens are selected.

Flavivirus: Viral antigens include, but are not limited to, those derived from a Flavivirus, such as Tick-borne encephalitis (TBE) virus, Dengue (types 1, 2, 3 or 4) virus, Yellow Fever virus, Japanese encephalitis virus, Kyasanur Forest Virus, West Nile encephalitis virus, St. Louis encephalitis virus, Russian spring-summer encephalitis virus, Powassan encephalitis virus. In certain embodiments, the flavivirus antigens are selected from PrM, M, C, E, NS-1, NS-2a, NS2b, NS3, NS4a, NS4b, and NS5. In certain embodiments, the flavivirus antigens are selected from PrM, M and E.

Pestivirus: Viral antigens include, but are not limited to, those derived from a Pestivirus, such as Bovine viral diarrhea (BVDV), Classical swine fever (CSFV) or Border disease (BDV).

Hepadnavirus: Viral antigens include, but are not limited to, those derived from a Hepadnavirus, such as Hepatitis B virus. In certain embodiments, the hepadnavirus antigens are selected from surface antigens (L, M and S), core antigens (HBc, HBe).

Hepatitis C virus: Viral antigens include, but are not limited to, those derived from a Hepatitis C virus (HCV). In certain embodiments, the HCV antigens are selected from one or more of E1, E2, E1/E2, NS345 polyprotein, NS 345-core polyprotein, core, and/or peptides from the nonstructural regions. In certain embodiments, the Hepatitis C virus antigens include one or more of the following: HCV E1 and or E2 proteins, E1/E2 heterodimer complexes, core proteins and non-structural proteins, or fragments of these antigens, wherein the non-structural proteins can optionally be modified to remove enzymatic activity but retain immunogenicity Rhabdovirus: Viral antigens include, but are not limited to, those derived from a Rhabdovirus, such as a Lyssavirus (Rabies virus) and Vesiculovirus (VSV). Rhabdovirus antigens may be selected from glycoprotein (G), nucleoprotein (N), large protein (L), nonstructural proteins (NS).

Caliciviridae; Viral antigens include, but are not limited to, those derived from Calciviridae, such as Norwalk virus, and Norwalk-like Viruses, such as Hawaii Virus and Snow Mountain Virus.

Coronavirus: Viral antigens include, but are not limited to, those derived from a Coronavirus, SARS, Human respiratory coronavirus, Avian infectious bronchitis (IBV), Mouse hepatitis virus (MHV), and Porcine transmissible gastroenteritis virus (TGEV). In certain embodiments, the coronavirus antigens are selected from spike (S), envelope (E), matrix (M), nucleocapsid (N), and Hemagglutinin-esterase glycoprotein (HE). In certain embodiments, the coronavirus antigen is derived from a SARS virus. In certain embodiments, the coronavirus is derived from a SARS viral antigen as described in WO 04/92360.

Retrovirus: Viral antigens include, but are not limited to, those derived from a Retrovirus, such as an Oncovirus, a Lentivirus or a Spumavirus. In certain embodiments, the oncovirus antigens are derived from HTLV-1, HTLV-2 or HTLV-5. In certain embodiments, the lentivirus antigens are derived from HIV-1 or HIV-2. In certain embodiments, the antigens are derived from HIV-1 subtypes (or clades), including, but not limited to, HIV-1 subtypes (or clades) A, B, C, D, F, G, H, J, K, O. In other embodiments, the antigens are derived from HIV-1 circulating recombinant forms (CRFs), including, but not limited to, A/B, A/E, A/G, A/G/I, etc. In certain embodiments, the retrovirus antigens are selected from gag, pol, env, tax, tat, rex, rev, nef, vif, vpu, and vpr. In certain embodiments, the HIV antigens are selected from gag (p24gag and p55gag), env (gp160 and gp41), pol, tat, nef, rev vpu, miniproteins, (preferably p55 gag and gp140v delete). In certain embodiments, the HIV antigens are derived from one or more of the following strains: $HIV_{IIIb}$, $HIV_{SF2}$, $HIV_{LAV}$, $HIV_{LAI}$, $HIV_{MN}$, $HIV-1_{CM235}$, $HIV-1_{US4}$, $HIV-1_{SF1625}$, $HIV-1_{TV1}$, $HIV-1_{MJ4}$. In certain embodiments, the antigens are derived from endogenous human retroviruses, including, but not limited to, HERV-K ("old" HERV-K and "new" HERV-K).

Reovirus: Viral antigens include, but are not limited to, those derived from a Reovirus, such as an Orthoreovirus, a Rotavirus, an Orbivirus, or a Coltivirus. In certain embodiments, the reovirus antigens are selected from structural proteins $\lambda 1$, $\lambda 2$, $\lambda 3$, $\mu 1$, $\mu 2$, $\sigma 1$, $\sigma 2$, or $\sigma 3$, or nonstructural proteins $\sigma NS$, $\mu NS$, or $\sigma 1s$. In certain embodiments, the reovirus antigens are derived from a Rotavirus. In certain embodiments, the rotavirus antigens are selected from VP1, VP2, VP3, VP4 (or the cleaved product VP5 and VP8), NSP 1, VP6, NSP3, NSP2, VP7, NSP4, or NSP5. In certain embodiments, the rotavirus antigens include VP4 (or the cleaved product VP5 and VP8), and VP7.

Parvovirus: Viral antigens include, but are not limited to, those derived from a Bocavirus and Parvovirus, such as Parvovirus B19. In certain embodiments, the Parvovirus antigens are selected from VP-1, VP-2, VP-3, NS-1 and NS-2. In certain embodiments, the Parvovirus antigen is capsid protein VP1 or VP-2.

Delta hepatitis virus (HDV): Viral antigens include, but are not limited to, those derived from HDV, particularly δ-antigen from HDV.

Hepatitis E virus (HEV): Viral antigens include, but are not limited to, those derived from HEV.

Hepatitis G virus (HGV): Viral antigens include, but are not limited to, those derived from HGV.

Human Herpesvirus: Viral antigens include, but are not limited to, those derived from a Human Herpesvirus, such as, by way of example only, Herpes Simplex Viruses (HSV), Varicella-zoster virus (VZV), Epstein-Barr virus (EBV), Cytomegalovirus (CMV), Human Herpesvirus 6 (HHV6), Human Herpesvirus 7 (HHV7), and Human Herpesvirus 8 (HHV8). In certain embodiments, the Human Herpesvirus antigens are selected from immediate early proteins ($\alpha$), early proteins ($\beta$), and late proteins ($\gamma$). In certain embodiments, the HSV antigens are derived from HSV-1 or HSV-2 strains. In certain embodiments, the HSV antigens are selected from glycoproteins gB, gC, gD and gH, fusion protein (gB), or immune escape proteins (gC, gE, or gI). In certain embodiments, the VZV antigens are selected from core, nucleocapsid, tegument, or envelope proteins. In certain embodiments, the EBV antigens are selected from early antigen (EA) proteins, viral capsid antigen (VCA), and glycoproteins of the membrane antigen (MA). In certain embodiments, the CMV antigens are selected from capsid proteins, envelope glycoproteins (such as gB and gH), and tegument proteins. In other embodiments, CMV antigens may be selected from one or more of the following proteins: pp 65, IE1, gB, gD, gH, gL, gM, gN, gO, UL128, UL129, gUL130, UL150, UL131, UL33, UL78, US27, US28, RL5A, RL6, RL10, RL11, RL12, RL13, UL1, UL2, UL4, UL5, UL6, UL7, UL8, UL9, UL10, UL11, UL14, UL15A, UL16, UL17, UL18, UL22A, UL38, UL40, UL41A, UL42, UL116, UL119, UL120, UL121, UL124, UL132, UL147A, UL148, UL142, UL144, UL141, UL140, UL135, UL136, UL138, UL139, UL133, UL135, UL148A, UL148B, UL148C, UL148D, US2, US3, US6, US7, US8, US9, US10, US11, US12, US13, US14, US15, US16, US17, US18, US19, US20, US21, US29, US30 and US34A. CMV antigens may also be fusions of one or more CMV proteins, such as, by way of example only, pp 65/IE1 (Reap et al., Vaccine (2007) 25:7441-7449).

Papovaviruses: Antigens include, but are not limited to, those derived from Papovaviruses, such as Papillomaviruses and Polyomaviruses. In certain embodiments, the Papillomaviruses include HPV serotypes 1, 2, 4, 5, 6, 8, 11, 13, 16, 18, 31, 33, 35, 39, 41, 42, 47, 51, 57, 58, 63 and 65. In certain embodiments, the HPV antigens are derived from serotypes 6, 11, 16 or 18. In certain embodiments, the HPV antigens are selected from capsid proteins (L1) and (L2), or E1-E7, or fusions thereof. In certain embodiments, the Polyomyavirus viruses include BK virus and JK virus. In certain embodiments, the Polyomavirus antigens are selected from VP1, VP2 or VP3.

Adenovirus: Antigens include those derived from Adenovirus. In certain embodiments, the Adenovirus antigens are derived from Adenovirus serotype 36 (Ad-36). In certain embodiments, the antigen is derived from a protein or peptide sequence encoding an Ad-36 coat protein or fragment thereof (WO 2007/120362).

Arenavirus: Viral antigens include, but are not limited to, those derived from Arenaviruses.

Fish Viruses: In some embodiments, the antigen elicits an immune response against a virus which infects fish, such as: infectious salmon anemia virus (ISAV), salmon pancreatic disease virus (SPDV), infectious pancreatic necrosis virus (IPNV), channel catfish virus (CCV), fish lymphocystis disease virus (FLDV), infectious hematopoietic necrosis virus (1HNV), koi herpesvirus, salmon picorna-like virus (also known as picorna-like virus of atlantic salmon), landlocked salmon virus (LSV), atlantic salmon rotavirus (ASR), trout strawberry disease virus (TSD), coho salmon tumor virus (CSTV), or viral hemorrhagic septicemia virus (VHSV).

Bacterial Antigens

Bacterial antigens suitable for the present invention include, but are not limited to, proteins and peptides from a bacteria. Bacterial antigens include antigens derived from one or more of the bacteria set forth below as well as the specific antigens examples identified below. In some embodiments, the antigen elicits an immune response against one of these bacteria:

Neisseria meningitidis: Antigens include, but are not limited to, membrane proteins such as adhesins, autotransporters, toxins, iron acquisition proteins, and factor H binding protein. A combination of three useful polypeptides is disclosed in Giuliani et al. (2006) Proc. Natl. Acad. Sci. USA 103(29):10834-10839.

Streptococcus pneumoniae: Streptococcus pneumoniae antigens include, but are not limited to, antigens disclosed in WO2009/016515. These include, but are not limited to, the RrgB pilus subunit, the beta-N-acetyl-hexosaminidase precursor (spr0057), spr0096, General stress protein GSP-781 (spr2021, SP2216), serine/threonine kinase StkP(SP1732), and pneumococcal surface adhesin PsaA.

Streptococcus pyogenes (Group A Streptococcus): Group A Streptococcus antigens include, but are not limited to, a protein identified in WO 02/34771 or WO 2005/032582 (including GAS 40), fusions of fragments of GAS M proteins (including those described in WO 02/094851, and Dale (1999) Vaccine 17:193-200, and Dale (1996) Vaccine 14(10): 944-948), fibronectin binding protein (Sfb1), Streptococcal heme-associated protein (Shp), and Streptolysin S (SagA).

Moraxella catarrhalis: Moraxella antigens include, but are not limited to, antigens identified in WO 02/18595 and WO 99/58562, outer membrane protein antigens (HMW-OMP), C-antigen, and/or LPS.

Bordetella pertussis: Pertussis antigens include, but are not limited to, pertussis holotoxin (PT) and filamentous haemagglutinin (FHA) from B. pertussis, optionally also combination with pertactin and/or agglutinogens 2 and 3.

Burkholderia: Burkholderia antigens include, but are not limited to Burkholderia mallei, Burkholderia pseudomallei and Burkholderia cepacia.

Staphylococcus aureus: Antigens include, but are not limited to antigens derived from surface proteins, invasins (leukocidin, kinases, hyaluronidase), surface factors that inhibit phagocytic engulfment (capsule, Protein A), carotenoids, catalase production, Protein A, coagulase, clotting factor, and/or membrane-damaging toxins (optionally detoxified) that lyse eukaryotic cell membranes (hemolysins, leukotoxin, leukocidin). In certain embodiments, useful antigens may be selected from a protein identified in WO 02/094868, WO 2008/019162, WO 02/059148, WO 02/102829, WO 03/011899, WO 2005/079315, WO 02/077183, WO 99/27109, WO 01/70955, WO 00/12689, WO 00/12131, WO 2006/032475, WO 2006/032472, WO 2006/032500, WO 2007/113222, WO 2007/113223, WO 2007/113224, PCT/IB2010/000998. In other embodiments, antigens may be selected from IsdA, IsdB, IsdC, SdrC, SdrD, SdrE, ClfA, Clfl3, SasF, SasD, SasH (AdsA), Spa, EsaC, EsxA, EsxB, Emp, H1aH35L, hemolysin, ferrichrome-binding protein (sta006) and/or the sta011 lipoprotein.

Staphylococcus epidermis: S. epidermidis antigens include, but are not limited to, slime-associated antigen (SAA).

Clostridium tetani (Tetanus): Tetanus antigens include, but are not limited to, tetanus toxoid (TT).

Clostridium perfringens: Antigens include, but are not limited to, Epsilon toxin from Clostridium perfringen.

Clostridium botulinums (Botulism): Botulism antigens include, but are not limited to, those derived from C. botulinum.

Cornynebacterium diphtheriae (Diphtheria): Diphtheria antigens include, but are not limited to, diphtheria toxin, preferably detoxified, such as $CRM_{197}$.

Haemophilus influenzae B (Hib): Hib antigens include, but are not limited to, antigens derived from Haemophilus influenzae B.

Pseudomonas aeruginosa: Pseudomonas antigens include, but are not limited to, those derived from Pseudomonas aeruginosa, such as endotoxin A and Wzz protein.

*Coxiella burnetii*. Bacterial antigens derived from *Coxiella burnetii*.

*Brucella*. Bacterial antigens derived from *Brucella*, including but not limited to, *B. abortus, B. canis, B. melitensis, B. neotomae, B. ovis, B. suis* and *B. pinnipediae*.

*Francisella*. Bacterial antigens derived from *Francisella*, including but not limited to, *F. novicida, F. philomiragia* and *F. tularensis*.

*Streptococcus agalactiae* (Group B *Streptococcus*): Group B *Streptococcus* antigens include, but are not limited to, a protein antigen identified in WO 02/34771, WO 03/093306, WO 04/041157, or WO 2005/002619 (including proteins GBS 80, GBS 104, GBS 276 and GBS 322).

*Neiserria gonorrhoeae*: Gonorrhoeae antigens include, but are not limited to, Por (or porin) protein, such as PorB (see Zhu et al., *Vaccine* (2004) 22:660-669), a transferring binding protein, such as TbpA and TbpB (See Price et al., Infect. Immun. (2004) 71(1):277-283), a opacity protein (such as Opa), a reduction-modifiable protein (Rmp).

*Chlamydia trachomatis: Chlamydia trachomatis* antigens include, but are not limited to, antigens derived from serotypes A, B, Ba and C (agents of trachoma, a cause of blindness), serotypes $L_1$, $L_2$ & $L_3$ (associated with Lymphogranuloma venereum), and serotypes, D-K. In certain embodiments, chlamydia trachomas antigens include, but are not limited to, an antigen identified in WO 00/37494, WO 03/049762, WO 03/068811, or WO 05/002619, including PepA (CT045), LcrE (CT089), ArtJ (CT381), DnaK (CT396), CT398, OmpH-like (CT242), L7/L12 (CT316), OmcA (CT444), AtosS (CT467), CT547, Eno (CT587), HrtA (CT823), and MurG (CT761).

*Treponema pallidum* (Syphilis): Syphilis antigens include, but are not limited to, TmpA antigen.

*Haemophilus* ducreyi (causing chancroid): Ducreyi antigens include, but are not limited to, outer membrane protein (DsrA).

*Enterococcus faecalis* or *Enterococcus faecium*: Antigens include, but are not limited to, a trisaccharide repeat or other *Enterococcus* derived antigens.

*Helicobacter pylori*: H pylori antigens include, but are not limited to, Cag, Vac, Nap, HopX, HopY and/or urease antigen.

*Staphylococcus saprophyticus*: Antigens include, but are not limited to, the 160 kDa hemagglutinin of *S. saprophyticus* antigen.

*Yersinia enterocolitica* Antigens include, but are not limited to, LPS.

*E. coli*: Antigens include, but are not limited to, antigens derived from enterotoxigenic *E. coli* (ETEC), enteroaggregative *E. coli* (EAggEC), diffusely adhering *E. coli* (DAEC), enteropathogenic *E. coli* (EPEC), extraintestinal pathogenic *E. coli* (ExPEC) and/or enterohemorrhagic *E. coli* (EHEC). ExPEC strains include uropathogenic *E. coli* (UPEC) and meningitis/sepsis-associated *E. coli* (MNEC). Antigens include, but are not limited to, accessory colonization factor (orf3526), orf353, bacterial Ig-like domain (group 1) protein (orf405), orf1364, NodT-family outer-membrane-factor-lipoprotein efflux transporter (orf1767), gspK (orf3515), gspJ (orf3516), tonB-dependent siderophore receptor (orf3597), fimbrial protein (orf3613), upec-948, upec-1232, A chain precursor of the type-1 fimbrial protein (upec-1875), yap H homolog (upec-2820), and hemolysin A (recp-3768). Useful UPEC polypeptide antigens are disclosed in WO2006/091517 and WO2008/020330. Useful MNEC antigens are disclosed in WO2006/089264. A useful antigen for several *E. coli* types is AcfD WO2009/104092.

*Bacillus anthracis* (anthrax): *B. anthracis* antigens include, but are not limited to, A-components (lethal factor (LF) and edema factor (EF)), both of which can share a common B-component known as protective antigen (PA). In certain embodiments, *B. anthracis* antigens are optionally detoxified.

*Yersinia pestis* (plague): Plague antigens include, but are not limited to, F1 capsular antigen, LPS, *Yersinia pestis* V antigen.

*Mycobacterium tuberculosis*: Tuberculosis antigens include, but are not limited to, lipoproteins, LPS, BCG antigens, a fusion protein of antigen 85B (Ag85B), ESAT-6 optionally formulated in cationic lipid vesicles, *Mycobacterium tuberculosis* (Mtb) isocitrate dehydrogenase associated antigens, and MPT51 antigens.

*Rickettsia*: Antigens include, but are not limited to, outer membrane proteins, including the outer membrane protein A and/or B (OmpB), LPS, and surface protein antigen (SPA).

*Listeria monocytogenes*: Bacterial antigens include, but are not limited to, those derived from *Listeria monocytogenes*.

*Chlamydia pneumoniae: Antigens include, but are not limited to, those identified in WO* 02/02606.

*Vibrio cholerae*: Antigens include, but are not limited to, proteinase antigens, LPS, particularly lipopolysaccharides of *Vibrio cholerae* II, 01 Inaba O-specific polysaccharides, *V. cholera* 0139, antigens of IEM108 vaccine and Zonula occludens toxin (Zot).

*Salmonella typhi* (typhoid fever): Antigens include, but are not limited to, those derived from *Salmonella typhi*.

*Borrelia burgdorferi* (Lyme disease): Antigens include, but are not limited to, lipoproteins (such as OspA, OspB, Osp C and Osp D), other surface proteins such as OspE-related proteins (Erps), decorin-binding proteins (such as DbpA), and antigenically variable VI proteins, such as antigens associated with P39 and P13 (an integral membrane protein, V1sE Antigenic Variation Protein.

*Porphyromonas gingivalis*: Antigens include, but are not limited to, *P. gingivalis* outer membrane protein (OMP). *Klebsiella*: Antigens include, but are not limited to, an OMP, including OMP A.

Fungal Antigens

Fungal antigens may be derived from Dermatophytres, including: *Epidermophyton floccusum, Microsporum audouini, Microsporum canis, Microsporum distortum, Microsporum equinum, Microsporum gypsum, Microsporum nanum, Trichophyton concentricum, Trichophyton equinum, Trichophyton gallinae, Trichophyton gypseum, Trichophyton megnini, Trichophyton mentagrophytes, Trichophyton quinckeanum, Trichophyton rubrum, Trichophyton schoenleini, Trichophyton tonsurans, Trichophyton verrucosum, T. verrucosum* var. *album*, var. *discoides*, var. *ochraceum, Trichophyton violaceum*, and/or *Trichophyton faviforme*; or from *Aspergillus fumigatus, Aspergillus flavus, Aspergillus niger, Aspergillus nidulans, Aspergillus terreus, Aspergillus sydowi, Aspergillus flavatus, Aspergillus glaucus, Blastoschizomyces capitatus, Candida albicans, Candida enolase, Candida tropicalis, Candida glabrata, Candida krusei, Candida parapsilosis, Candida stellatoidea, Candida kusei, Candida parakwsei, Candida lusitaniae, Candida pseudotropicalis, Candida guilliermondi, Cladosporium carrionii, Coccidioides immitis, Blastomyces dermatidis, Cryptococcus neoformans, Geotrichum clavatum, Histoplasma capsulatum, Klebsiella pneumoniae, Microsporidia, Encephalitozoon* spp., *Septata intestinalis* and *Enterocytozoon bieneusi*; the less common are *Brachiola* spp, *Microsporidium* spp., *Nosema* spp., *Pleistophora* spp., *Trachipleistophora* spp., *Vittaforma* spp *Paracoccidioides brasiliensis, Pneumocystis carinii, Pythiumn insidiosum, Pityrosporum ovale, Sacharomyces cerevisae, Saccharomyces boulardii, Saccharomyces pombe, Scedosporium apiosperum, Sporothrix schenckii, Trichosporon beigelii, Toxoplasma gondii, Penicillium marneffei, Malassezia* spp., *Fonsecaea* spp., *Wangiella* spp., *Sporothrix* spp., *Basidiobolus* spp., *Conidiobolus* spp., *Rhizopus* spp, *Mucor* spp, *Absidia* spp, *Mortierella* spp, *Cunninghamella* spp, *Saksenaea* spp., *Alternaria* spp, *Curvularia* spp, *Helminthosporium* spp, *Fusarium* spp, *Aspergillus* spp, *Penicillium* spp, *Monolinia* spp, *Rhizoctonia* spp, *Paecilomyces* spp, *Pithomyces* spp, and *Cladosporium* spp.

Protazoan Antigens/Pathogens

Protazoan antigens/pathogens for use herein include, but are not limited to, those derived from one or more of the following protozoa: *Entamoeba histolytica, Giardia lambli, Cryptosporidium parvum, Cyclospora cayatanensis* and *Toxoplasma*.

Plant Antigens/Pathogens

Plant antigens/pathogens for use herein include, but are not limited to, those derived from *Ricinus communis*.

Tumor Antigens

In certain embodiments, a tumor antigen, or cancer antigen, is used in the invention. In certain embodiments, the tumor antigens are peptide-containing tumor antigens, such as a polypeptide tumor antigen or glycoprotein tumor antigens.

Tumor antigens appropriate for the use herein encompass a wide variety of molecules, such as (a) polypeptide-containing tumor antigens, including polypeptides (which can range, for example, from 8-20 amino acids in length, although lengths outside this range are also common), lipopolypeptides and glycoproteins.

In certain embodiments, tumor antigens are, for example, (a) full length molecules associated with cancer cells, (b) homologs and modified forms of the same, including molecules with deleted, added and/or substituted portions, and (c) fragments of the same. Tumor antigens include, for example, class I-restricted antigens recognized by CD8+ lymphocytes or class II-restricted antigens recognized by CD4+ lymphocytes.

In certain embodiments, tumor antigens include, but are not limited to, (a) cancer-testis antigens such as NY-ESO-1, SSX$_2$, SCP1 as well as RAGE, BAGE, GAGE and MAGE family polypeptides, for example, GAGE-1, GAGE-2, MAGE-1, MAGE-2, MAGE-3, MAGE-4, MAGE-5, MAGE-6, and MAGE-12 (which can be used, for example, to address melanoma, lung, head and neck, NSCLC, breast, gastrointestinal, and bladder tumors), (b) mutated antigens, for example, p53 (associated with various solid tumors, e.g., colorectal, lung, head and neck cancer), p21/Ras (associated with, e.g., melanoma, pancreatic cancer and colorectal cancer), CDK4 (associated with, e.g., melanoma), MUM1 (associated with, e.g., melanoma), caspase-8 (associated with, e.g., head and neck cancer), CIA 0205 (associated with, e.g., bladder cancer), HLA-A2-R1701, beta catenin (associated with, e.g., melanoma), TCR (associated with, e.g., T-cell non-Hodgkins lymphoma), BCR-abl (associated with, e.g., chronic myelogenous leukemia), triosephosphate isomerase, KIA 0205, CDC-27, and LDLR-FUT, (c) over-expressed antigens, for example, Galectin 4 (associated with, e.g., colorectal cancer), Galectin 9 (associated with, e.g., Hodgkin's disease), proteinase 3 (associated with, e.g., chronic myelogenous leukemia), WT 1 (associated with, e.g., various leukemias), carbonic anhydrase (associated with, e.g., renal cancer), aldolase A (associated with, e.g., lung cancer), PRAME (associated with, e.g., melanoma), HER-2/neu (associated with, e.g., breast, colon, lung and ovarian cancer), alpha-fetoprotein (associated with, e.g., hepatoma), KSA (associated with, e.g., colorectal cancer), gastrin (associated with, e.g., pancreatic and gastric cancer), telomerase catalytic protein, MUC-1 (associated with, e.g., breast and ovarian cancer), G-250 (associated with, e.g., renal cell carcinoma), p53 (associated with, e.g., breast, colon cancer), and carcinoembryonic antigen (associated with, e.g., breast cancer, lung cancer, and cancers of the gastrointestinal tract such as colorectal cancer), (d) shared antigens, for example, melanoma-melanocyte differentiation antigens such as MART-1/Melan A, gp100, MC1R, melanocyte-stimulating hormone receptor, tyrosinase, tyrosinase related protein-1/TRP1 and tyrosinase related protein-2/TRP2 (associated with, e.g., melanoma), (e) prostate associated antigens such as PAP, PSA, PSMA, PSH-P1, PSM-P1, PSM-P2, associated with e.g., prostate cancer, (f) immunoglobulin idiotypes (associated with myeloma and B cell lymphomas, for example).

In certain embodiments, tumor antigens include, but are not limited to, p15, Hom/Mel-40, H-Ras, E2A-PRL, H4-RET, IGH-IGK, MYL-RAR, Epstein Barr virus antigens, EBNA, human papillomavirus (HPV) antigens, including E6 and E7, hepatitis B and C virus antigens, human T-cell lymphotropic virus antigens, TSP-180, p185erbB2, p180erbB-3, c-met, mn-23H1, TAG-72-4, CA 19-9, CA 72-4, CAM 17.1, NuMa, K-ras, p16, TAGE, PSCA, CT7, 43-9F,5T4, 791 Tgp72, beta-HCG, BCA225, BTAA, CA 125, CA 15-3 (CA 27.29\BCAA), CA 195, CA 242, CA-50, CAM43, CD68\KP1, CO-029, FGF-5, Ga733 (EpCAM), HTgp-175, M344, MA-50, MG7-Ag, MOV18, NB/70K, NY—CO-1, RCAS1, SDCCAG16, TA-90 (Mac-2 binding protein\cyclophilin C-associated protein), TAAL6, TAG72, TLP, TPS, and the like.

Parasite Antigens

In some embodiments, the antigen elicits an immune response against a parasite from the *Plasmodium* genus, such as *P. falciparum, P. vivax, P. malariae* or *P. ovale*. Thus the invention may be used for immunising against malaria.

Allegens

In some embodiments the antigen elicits an immune response against: pollen allergens (tree-, herb, weed-, and grass pollen allergens); insect or arachnid allergens (inhalant, saliva and venom allergens, e.g. mite allergens, cockroach and midges allergens, hymenopthera venom allergens); animal hair and dandruff allergens (from e.g. dog, cat, horse, rat, mouse, etc.); and food allergens (e.g. a gliadin). Important pollen allergens from trees, grasses and herbs are such originating from the taxonomic orders of Fagales, Oleales, Pinales and platanaceae including, but not limited to, birch (Betula), alder (Alnus), hazel (Corylus), hornbeam (Carpinus) and olive (Olea), cedar (Cryptomeria and *Juniperus*), plane tree (Platanus), the order of Poales including grasses of the genera *Lolium, Phleum, Poa, Cynodon, Dactylis, Holcus, Phalaris, Secale*, and *Sorghum*, the orders of Asterales and Urticales including herbs of the genera *Ambrosia, Artemisia*, and *Parietaria*. Other important inhalation allergens are those from house dust mites of the genus *Dermatophagoides* and *Euroglyphus*, storage mite e.g. *Lepidoglyphys, Glycyphagus* and *Tyrophagus*, those from cockroaches, midges and fleas e.g. Blatella, Periplaneta, Chironomus and Ctenocepphalides, and those from mammals such as cat, dog and horse, venom allergens including such originating from stinging or biting insects such as those from the taxonomic order of Hymenoptera including bees (Apidae), wasps (Vespidea), and ants (Formicoidae).

It is readily apparent that the present invention can be used to raise antibodies to a large number of antigens for diagnostic and immunopurification purposes, as well as to prevent or treat a wide variety of diseases.

4. Immunological Adjuvants

As noted above, immunogenic compositions in accordance with the invention may include one or more optional immunological adjuvants. Immunological adjuvants for use with the invention include, but are not limited to, one or more of the following set forth below:

A. Mineral Containing Compositions

Mineral containing compositions suitable for use as immunological adjuvants include mineral salts, such as aluminum salts and calcium salts. The invention includes mineral salts such as hydroxides (e.g. oxyhydroxides), phosphates (e.g. hydroxyphosphates, orthophosphates), sulfates, etc. (see, e.g., *Vaccine Design: The Subunit and Adjuvant Approach* (Powell, M. F. and Newman, M. J. eds.) (New York: Plenum Press) 1995, Chapters 8 and 9), or mixtures of different mineral compounds (e.g. a mixture of a phosphate and a hydroxide adjuvant, optionally with an excess of the phosphate), with the compounds taking any suitable form (e.g. gel, crystalline, amorphous, etc.), and with adsorption to the salt(s) being preferred. The mineral containing compositions may also be formulated as a particle of metal salt (WO 00/23105).

The adjuvants known as "aluminium hydroxide" are typically aluminium oxyhydroxide salts, which are usually at least partially crystalline. Aluminium oxyhydroxide, which can be represented by the formula AlO(OH), can be distinguished from other aluminium compounds, such as aluminium hydroxide Al(OH)$_3$, by infrared (IR) spectroscopy, in particular by the presence of an adsorption band at 1070 cm$^{-1}$ and a strong shoulder at 3090-3100 cm$^{-1}$ [chapter 9 of *Vaccine Design* . . . (1995) eds. Powell & Newman. ISBN: 030644867X. Plenum.] The degree of crystallinity of an aluminum hydroxide adjuvant is reflected by the width of the diffraction band at half height (WHH), with poorly-crystalline particles showing greater line broadening due to smaller crystallite sizes. The surface area increases as WHH increases, and adjuvants with higher WHH values have been seen to have greater capacity for antigen adsorption. A fibrous morphology (e.g. as seen in transmission electron micrographs) is typical for aluminum hydroxide adjuvants. The pI of aluminium hydroxide adjuvants is typically about 11 i.e. the adjuvant itself has a positive surface charge at physiological pH. Adsorptive capacities of between 1.8-2.6 mg protein per mg Al$^{+++}$ at pH 7.4 have been reported for aluminium hydroxide adjuvants.

The adjuvants known as "aluminium phosphate" are typically aluminium hydroxyphosphates, often also containing a small amount of sulfate (i.e. aluminium hydroxyphosphate sulfate). They may be obtained by precipitation, and the reaction conditions and concentrations during precipitation influence the degree of substitution of phosphate for hydroxyl in the salt. Hydroxyphosphates generally have a PO$_4$/Al molar ratio between 0.3 and 1.2. Hydroxyphosphates can be distinguished from strict AlPO$_4$ by the presence of hydroxyl groups. For example, an IR spectrum band at 3164 cm$^{-1}$ (e.g. when heated to 200° C.) indicates the presence of structural hydroxyls [ch. 9 of *Vaccine Design* . . . (1995) eds. Powell & Newman. ISBN: 030644867X. Plenum.].

The PO$_4$/Al$^{3+}$ molar ratio of an aluminium phosphate adjuvant will generally be between 0.3 and 1.2, preferably between 0.8 and 1.2, and more preferably 0.95±0.1. The aluminium phosphate will generally be amorphous, particularly for hydroxyphosphate salts. A typical adjuvant is amorphous aluminium hydroxyphosphate with PO$_4$/Al molar ratio between 0.84 and 0.92, included at 0.6 mg Al$^{3+}$/ml. The aluminium phosphate will generally be particulate (e.g. plate-like morphology as seen in transmission electron micrographs). Typical diameters of the particles are in the range 0.5-20 μm (e.g. about 5-10 μm) after any antigen adsorption. Adsorptive capacities of between 0.7-1.5 mg protein per mg Al$^{+++}$ at pH 7.4 have been reported for aluminium phosphate adjuvants.

The point of zero charge (PZC) of aluminium phosphate is inversely related to the degree of substitution of phosphate for hydroxyl, and this degree of substitution can vary depending on reaction conditions and concentration of reactants used for preparing the salt by precipitation. PZC is also altered by changing the concentration of free phosphate ions in solution (more phosphate=more acidic PZC) or by adding a buffer such as a histidine buffer (makes PZC more basic). Aluminium phosphates used according to the invention will generally have a PZC of between 4.0 and 7.0, more preferably between 5.0 and 6.5 e.g. about 5.7.

Suspensions of aluminium salts used to prepare compositions of the invention may contain a buffer (e.g. a phosphate or a histidine or a Tris buffer), but this is not always necessary. The suspensions are preferably sterile and pyrogen-free. A suspension may include free aqueous phosphate ions e.g. present at a concentration between 1.0 and 20 mM, preferably between 5 and 15 mM, and more preferably about 10 mM. The suspensions may also comprise sodium chloride.

In one embodiment, an adjuvant component includes a mixture of both an aluminium hydroxide and an aluminium phosphate. In this case there may be more aluminium phosphate than hydroxide e.g. a weight ratio of at least 2:1 e.g. ≥5:1, ≥6:1, ≥7:1, ≥8:1, ≥9:1, etc.

The concentration of Al$^{+++}$ in a composition for administration to a patient is preferably less than 10 mg/ml e.g. ≤5 mg/ml, ≤4 mg/ml, ≤3 mg/ml, ≤2 mg/ml, ≤1 mg/ml, etc. A preferred range is between 0.3 and 1 mg/ml. A maximum of <0.85 mg/dose is preferred.

B. Oil-Emulsions

Oil-emulsion compositions and formulations suitable for use as immunological adjuvants (with or without other specific immunostimulating agents such as muramyl peptides or bacterial cell wall components) include squalene-water emulsions, such as MF59 (5% Squalene, 0.5% Tween 80, and 0.5% Span 85, formulated into submicron particles using a microfluidizer). See WO 90/14837. See also, Podda (2001) *Vaccine* 19: 2673-2680; Frey et al. (2003) *Vaccine* 21:4234-4237. MF59 is used as the adjuvant in the FLUAD™ influenza virus trivalent subunit vaccine.

Adjuvants for use in the compositions include submicron oil-in-water emulsions. Preferred submicron oil-in-water emulsions for use herein are squalene/water emulsions optionally containing varying amounts of MTP-PE, such as a submicron oil-in-water emulsion containing 4-5% w/v squalene, 0.25-1.0% w/v Tween 80™ (polyoxyethylenesorbitan monooleate), and/or 0.25-1.0% Span 85™ (sorbitan trioleate), and, optionally, N-acetylmuramyl-L-alanyl-D-isogluatminyl-L-alanine-2-(1'-2'-dipalmitoyl-sn-glycero-3-huydroxyphosphosphoryloxy)-ethylamine (MTP-PE), for example, the submicron oil-in-water emulsion known as "MF59" (WO 90/14837; U.S. Pat. No. 6,299,884; U.S. Pat. No. 6,451,325; and Ott et al., "MF59—Design and Evaluation of a Safe and Potent Adjuvant for Human Vaccines" in *Vaccine Design: The Subunit and Adjuvant Approach* (Powell, M. F. and Newman, M. J. eds.) (New York: Plenum Press) 1995, pp. 277-296). MF59 contains 4-5% w/v Squalene (e.g. 4.3%), 0.25-0.5% w/v Tween 80™, and 0.5% w/v Span 85™ and optionally contains various amounts of MTP-PE, formulated into submicron particles using a microfluidizer such as Model 110Y microfluidizer (Microfluidics, Newton, Mass.).

For example, MTP-PE may be present in an amount of about 0-500 µg/dose, more preferably 0-250 µg/dose and most preferably, 0-100 µg/dose. As used herein, the term "MF59-0" refers to the above submicron oil-in-water emulsion lacking MTP-PE, while the term MF59-MTP denotes a formulation that contains MTP-PE. For instance, "MF59-100" contains 100 µg MTP-PE per dose, and so on. MF69, another submicron oil-in-water emulsion for use herein, contains 4.3% w/v squalene, 0.25% w/v Tween 80™, and 0.75% w/v Span 85™ and optionally MTP-PE. Yet another submicron oil-in-water emulsion is MF75, also known as SAF, containing 10% squalene, 0.4% Tween 80™, 5% pluronic-blocked polymer L121, and thr-MDP, also microfluidized into a submicron emulsion. MF75-MTP denotes an MF75 formulation that includes MTP, such as from 100-400 µg MTP-PE per dose.

Submicron oil-in-water emulsions, methods of making the same and immunostimulating agents, such as muramyl peptides, for use in the compositions, are described in detail in WO 90/14837; U.S. Pat. No. 6,299,884; and U.S. Pat. No. 6,451,325.

Complete Freund's adjuvant (CFA) and incomplete Freund's adjuvant (IFA) may also be used as adjuvants in the invention.

C. Saponin Formulations

Saponin formulations are also suitable for use as immunological adjuvants in the invention. Saponins are a heterologous group of sterol glycosides and triterpenoid glycosides that are found in the bark, leaves, stems, roots and even flowers of a wide range of plant species. Saponins isolated from the bark of the *Quillaia saponaria* Molina tree have been widely studied as adjuvants. Saponins can also be commercially obtained from *Smilax ornata* (sarsaprilla), *Gypsophilla paniculata* (brides veil), and *Saponaria officianalis* (soap root). Saponin adjuvant formulations include purified formulations, such as QS21, as well as lipid formulations, such as ISCOMs. Saponin adjuvant formulations include STIMULON® adjuvant (Antigenics, Inc., Lexington, Mass.).

Saponin compositions have been purified using High Performance Thin Layer Chromatography (HP-TLC) and Reversed Phase High Performance Liquid Chromatography (RP-HPLC). Specific purified fractions using these techniques have been identified, including QS7, QS17, QS18, QS21, QH-A, QH-B and QH-C. Preferably, the saponin is QS21. A method of production of QS21 is disclosed in U.S. Pat. No. 5,057,540. Saponin formulations may also comprise a sterol, such as cholesterol (see WO 96/33739).

Combinations of saponins and cholesterols can be used to form unique particles called Immunostimulating Complexes (ISCOMs). ISCOMs typically also include a phospholipid such as phosphatidylethanolamine or phosphatidylcholine. Any known saponin can be used in ISCOMs. Preferably, the ISCOM includes one or more of Quil A, QHA and QHC. ISCOMs are further described in EP 0 109 942, WO 96/11711 and WO 96/33739. Optionally, the ISCOMS may be devoid of (an) additional detergent(s). See WO 00/07621.

A review of the development of saponin based adjuvants can be found in Barr et al. (1998) *Adv. Drug Del. Rev.* 32:247-271. See also Sjolander et al. (1998) *Adv. Drug Del. Rev.* 32:321-338.

D. Virosomes and Virus Like Particles (VLPS)

Virosomes and Virus Like Particles (VLPs) are also suitable as immunological adjuvants. These structures generally contain one or more proteins from a virus optionally combined or formulated with a phospholipid. They are generally non-pathogenic, non-replicating and generally do not contain any of the native viral genome. The viral proteins may be recombinantly produced or isolated from whole viruses. These viral proteins suitable for use in virosomes or VLPs include proteins derived from influenza virus (such as HA or NA), Hepatitis B virus (such as core or capsid proteins), Hepatitis E virus, measles virus, Sindbis virus, Rotavirus, Foot-and-Mouth Disease virus, Retrovirus, Norwalk virus, human Papilloma virus, HIV, RNA-phages, Qβ-phage (such as coat proteins), GA-phage, fr-phage, AP205 phage, and Ty (such as retrotransposon Ty protein p1). VLPs are discussed further in WO 03/024480; WO 03/024481; Niikura et al. (2002) *Virology* 293:273-280; Lenz et al. (2001) *J. Immunol.* 166(9):5346-5355; Pinto et al. (2003) *J. Infect. Dis.* 188:327-338; and Gerber et al. (2001) *J. Virol.* 75(10):4752-4760. Virosomes are discussed further in, for example, Gluck et al. (2002) *Vaccine* 20:B10-B16. Immunopotentiating reconstituted influenza virosomes (IRIV) are used as the subunit antigen delivery system in the intranasal trivalent INFLEXAL™ product (Mischler and Metcalfe (2002) *Vaccine* 20 Suppl 5:B17-B23) and the INFLUVAC PLUS™ product.

E. Bacterial or Microbial Derivatives

Immunological adjuvants suitable for use in the invention include bacterial or microbial derivatives such as:

(1) Non-toxic derivatives of enterobacterial lipopolysaccharide (LPS): Such derivatives include Monophosphoryl lipid A (MPL) and 3-O-deacylated MPL (3dMPL). 3dMPL is a mixture of 3 De-O-acylated monophosphoryl lipid A with 4, 5 or 6 acylated chains. A preferred "small particle" form of 3 De-O-acylated monophosphoryl lipid A is disclosed in EP 0 689 454. Such "small particles" of 3dMPL are small enough to be sterile filtered through a 0.22 micron membrane (see EP 0 689 454). Other non-toxic LPS derivatives include monophosphoryl lipid A mimics, such as aminoalkyl glucosaminide phosphate derivatives, e.g., RC-529. See Johnson et al. (1999) *Bioorg. Med. Chem. Lett.* 9:2273-2278.

(2) Lipid A Derivatives: Lipid A derivatives include derivatives of lipid A from *Escherichia coli* such as OM-174. OM-174 is described for example in Meraldi et al. (2003) *Vaccine* 21:2485-2491; and Pajak et al. (2003) *Vaccine* 21:836-842.

(3) Immunostimulatory oligonucleotides: Immunostimulatory oligonucleotides or polymeric molecules suitable for use as adjuvants in the invention include nucleotide sequences containing a CpG motif (a sequence containing an unmethylated cytosine followed by guanosine and linked by a phosphate bond). Bacterial double stranded RNA or oligonucleotides containing palindromic or poly(dG) sequences have also been shown to be immunostimulatory. The CpG's can include nucleotide modifications/analogs such as phosphorothioate modifications and can be double-stranded or single-stranded. Optionally, the guanosine may be replaced with an analog such as 2'-deoxy-7-deazaguanosine. See Kandimalla et al. (2003) *Nucl. Acids Res.* 31(9): 2393-2400; WO 02/26757; and WO 99/62923 for examples of possible analog substitutions. The adjuvant effect of CpG oligonucleotides is further discussed in Krieg (2003) *Nat. Med.* 9(7):831-835; McCluskie et al. (2002) *FEMS Immunol. Med. Microbiol.* 32:179-185; WO 98/40100; U.S. Pat. No. 6,207,646; U.S. Pat. No. 6,239,116; and U.S. Pat. No. 6,429,199. The CpG sequence may be directed to TLR9, such as the motif GTCGTT or TTCGTT. See Kandimalla et al. (2003) *Biochem. Soc. Trans.* 31 (part 3):654-658. The CpG sequence may be specific for inducing a Th1 immune response, such as a CpG-A ODN, or it may be more specific for inducing a B cell response, such a CpG-B ODN. CpG-A and CpG-B ODNs are discussed in Blackwell et al. (2003) *J. Immunol.* 170(8): 4061-4068; Krieg (2002) *TRENDS Immunol.* 23(2): 64-65; and WO 01/95935. Preferably, the CpG is a CpG-A ODN.

Preferably, the CpG oligonucleotide is constructed so that the 5' end is accessible for receptor recognition. Optionally, two CpG oligonucleotide sequences may be attached at their 3' ends to form "immunomers". See, for example, Kandimalla et al. (2003) *BBRC* 306:948-953; Kandimalla et al. (2003) *Biochem. Soc. Trans.* 31(part 3):664-658; Bhagat et al. (2003) *BBRC* 300:853-861; and WO03/035836.

Immunostimulatory oligonucleotides and polymeric molecules also include alternative polymer backbone structures such as, but not limited to, polyvinyl backbones (Pitha et al. (1970) *Biochem. Biophys. Acta* 204(1):39-48; Pitha et al. (1970) *Biopolymers* 9(8):965-977), and morpholino backbones (U.S. Pat. No. 5,142,047; U.S. Pat. No. 5,185,444). A variety of other charged and uncharged polynucleotide analogs are known in the art. Numerous backbone modifications are known in the art, including, but not limited to, uncharged linkages (e.g., methyl phosphonates, phosphotriesters, phosphoamidates, and carbamates) and charged linkages (e.g., phosphorothioates and phosphorodithioates).

(4) ADP-ribosylating toxins and detoxified derivatives thereof: Bacterial ADP-ribosylating toxins and detoxified derivatives thereof may be used as adjuvants in the invention. Preferably, the protein is derived from *E. coli* (i.e., *E. coli* heat labile enterotoxin "LT"), cholera ("CT"), or pertussis ("PT"). The use of detoxified ADP-ribosylating toxins as mucosal adjuvants is described in WO 95/17211 and as parenteral adjuvants in WO 98/42375. Preferably, the adjuvant is a detoxified LT mutant such as LT-K63, LT-R72, and LTR192G. The use of ADP-ribosylating toxins and detoxified derivatives thereof, particularly LT-K63 and LT-R72, as adjuvants can be found in the following references: Beignon et al. (2002) *Infect. Immun.* 70(6):3012-3019; Pizza et al. (2001) *Vaccine* 19:2534-2541; Pizza et al. (2000) *Int. J. Med. Microbiol.* 290(4-5):455-461; Scharton-Kersten et al. (2000) *Infect. Immun.* 68(9):5306-5313; Ryan et al. (1999) *Infect. Immun.* 67(12):6270-6280; Partidos et al. (1999) *Immunol. Lett.* 67(3):209-216; Peppoloni et al. (2003) *Vaccines* 2(2):285-293; and Pine et al. (2002) *J. Control Release* 85(1-3):263-270. Numerical reference for amino acid substitutions is preferably based on the alignments of the A and B subunits of ADP-ribosylating toxins set forth in Domenighini et al. (1995) *Mol. Microbiol.* 15(6):1165-1167.

Compounds of formula I, II or III, or salts thereof, can also be used as adjuvants:

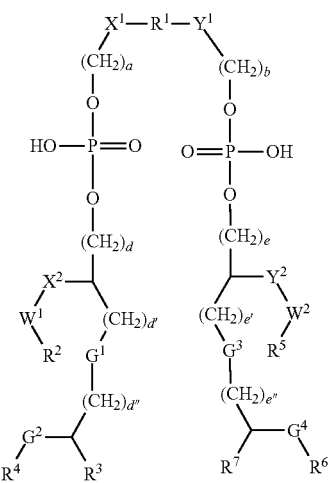

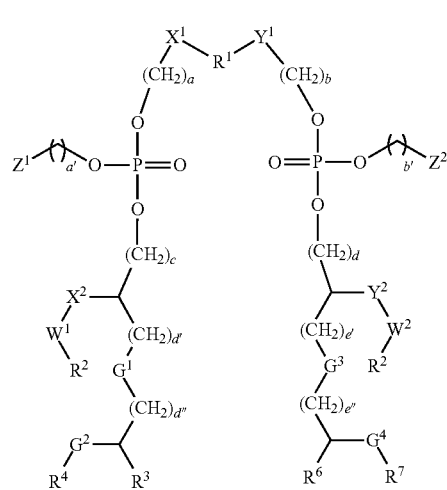

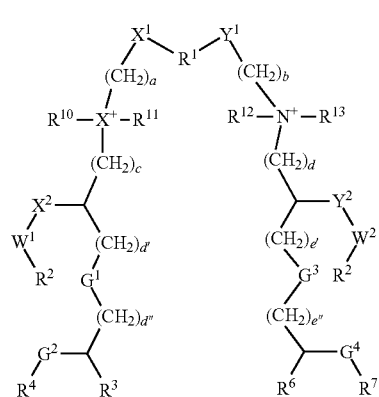

as defined in WO03/011223, such as 'ER 803058', 'ER 803732', 'ER 804053', ER 804058', 'ER 804059', 'ER 804442', 'ER 804680', 'ER 804764', ER 803022 or 'ER 804057' e.g.:

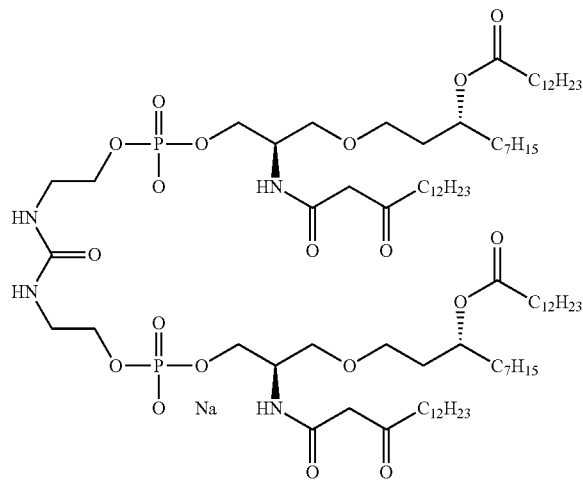

ER804057

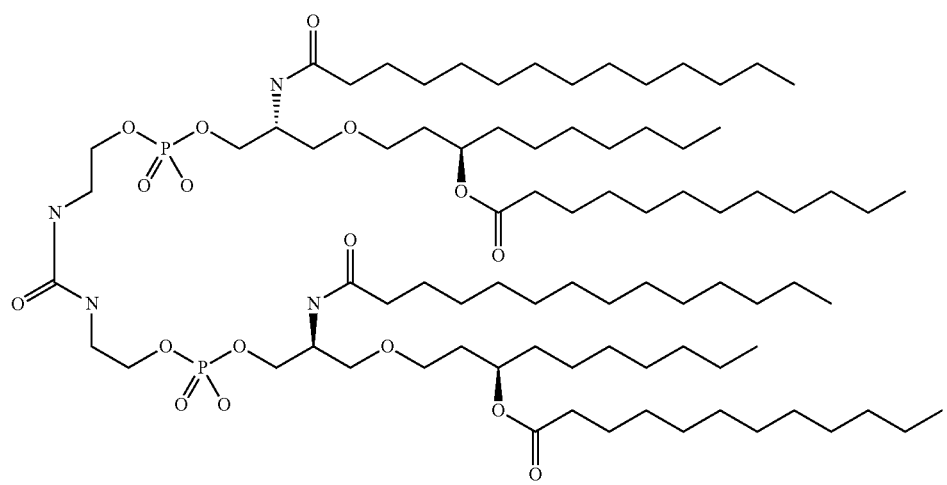

ER-803022

F. Human Immunomodulators

Human immunomodulators suitable for use as immunological adjuvants include cytokines, such as interleukins (e.g. IL-1, IL-2, IL-4, IL-5, IL-6, IL-7, IL-12, etc.), interferons (e.g. interferon-γ), macrophage colony stimulating factor (M-CSF), and tumor necrosis factor (TNF).

G. Bioadhesives and Mucoadhesives

Bioadhesives and mucoadhesives may also be used as immunological adjuvants. Suitable bioadhesives include esterified hyaluronic acid microspheres (Singh et al. (2001) *J. Cont. Release* 70:267-276) or mucoadhesives such as cross-linked derivatives of polyacrylic acid, polyvinyl alcohol, polyvinyl pyrollidone, polysaccharides and carboxymethylcellulose. Chitosan and derivatives thereof may also be used as adjuvants in the invention (see WO 99/27960).

H. Liposomes

Examples of liposome formulations suitable for use as immunological adjuvants are described in U.S. Pat. No. 6,090,406; U.S. Pat. No. 5,916,588; and EP Patent Publication No. EP 0 626 169.

I. Polyoxyethylene Ether and Polyoxyethylene Ester Formulations

Immunological adjuvants suitable for use in the invention include polyoxyethylene ethers and polyoxyethylene esters (see, e.g., WO 99/52549). Such formulations further include polyoxyethylene sorbitan ester surfactants in combination with an octoxynol (WO 01/21207) as well as polyoxyethylene alkyl ethers or ester surfactants in combination with at least one additional non-ionic surfactant such as an octoxynol (WO 01/21152).

Preferred polyoxyethylene ethers are selected from the following group:
polyoxyethylene-9-lauryl ether (laureth 9), polyoxyethylene-9-steoryl ether, polyoxytheylene-8-steoryl ether, polyoxyethylene-4-lauryl ether, polyoxyethylene-35-lauryl ether, and polyoxyethylene-23-lauryl ether.

J. Polyphosphazene (PCPP)

PCPP formulations suitable for use as immunological adjuvants are described, for example, in Andrianov et al. (1998) *Biomaterials* 19(1-3):109-115; and Payne et al. (1998) *Adv. Drug Del. Rev.* 31(3):185-196.

K. Muramyl Peptides

Examples of muramyl peptides suitable for use as immunological adjuvants include N-acetyl-muramyl-L-threonyl-D-isoglutamine (thr-MDP), N-acetyl-normuramyl-1-alanyl-d-isoglutamine (nor-MDP), and N-acetylmuramyl-1-alanyl-d-isoglutaminyl-1-alanine-2-(1'-2'-dipalmitoyl-sn-glycero-3-hydroxyphosphoryloxy)-ethylamine MTP-PE).

L. Imidazoquinoline Compounds

Examples of imidazoquinoline compounds suitable for use as immunological adjuvants include Imiquimod and its analogues, which are described further in Stanley (2002) *Clin.*

*Exp. Dermatol.* 27(7):571-577; Jones (2003) *Curr. Opin. Investig. Drugs* 4(2):214-218; and U.S. Pat. Nos. 4,689,338; 5,389,640; 5,268,376; 4,929,624; 5,266,575; 5,352,784; 5,494,916; 5,482,936; 5,346,905; 5,395,937; 5,238,944; and 5,525,612.

Imidazoquinolines for the practice of the present invention include imiquimod, resiquimod,

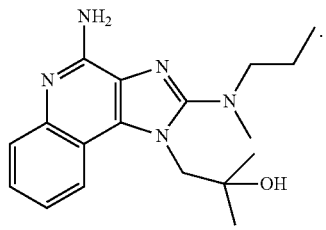 [SMILES: CCCN(C)c1nc2c(N)nc3ccccc3c2n1CC(C)(C)O]

See, e.g., Int. Pub. Nos. WO 2006/031878 to Valiante et al. and WO 2007/109810 to Sutton et al. Such compounds are known to be TLR7 agonists.

M. Thiosemicarbazone Compounds

Examples of thiosemicarbazone compounds suitable for use as immunological adjuvants, as well as methods of formulating, manufacturing, and screening for such compounds, include those described in WO 04/60308. The thiosemicarbazones are particularly effective in the stimulation of human peripheral blood mononuclear cells for the production of cytokines, such as TNF-α.

N. Tryptanthrin Compounds

Examples of tryptanthrin compounds suitable for use as immunological adjuvants, as well as methods of formulating, manufacturing, and screening for such compounds, include those described in WO 04/64759. The tryptanthrin compounds are particularly effective in the stimulation of human peripheral blood mononuclear cells for the production of cytokines, such as TNF-α.

O. Nucleoside Analogs

Various nucleoside analogs can be used as immunological adjuvants, such as (a) Isatorabine (ANA-245; 7-thia-8-oxoguanosine):

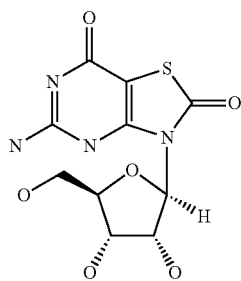 [SMILES: Nc1nc(=O)c2sc(=O)n([C@@H]3O[C@H](CO)[C@@H](O)[C@H]3O)c2[nH]1]

an U d prodrugs thereof; (b) ANA975; (c) ANA-025-1; (d) ANA380; (e) the compounds disclosed in U.S. Pat. No. 6,924,271; U.S. Publication No. 2005/0070556; and U.S. Pat. No. 5,658,731; (f) a compound having the formula:

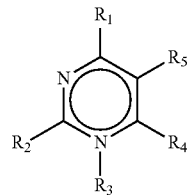

wherein:

$R_1$ and $R_2$ are each independently H, halo, $-NR_aR_b$, $-OH$, $C_{1-6}$ alkoxy, substituted $C_{1-6}$ alkoxy, heterocyclyl, substituted heterocyclyl, $C_{6-10}$ aryl, substituted $C_{6-10}$ aryl, $C_{1-6}$ alkyl, or substituted $C_{1-6}$ alkyl;

$R_3$ is absent, H, $C_{1-6}$ alkyl, substituted $C_{1-6}$ alkyl, $C_{6-10}$ aryl, substituted $C_{6-10}$ aryl, heterocyclyl, or substituted heterocyclyl;

$R_4$ and $R_5$ are each independently H, halo, heterocyclyl, substituted heterocyclyl, $-C(O)-R_d$, $C_{1-6}$ alkyl, substituted $C_{1-6}$ alkyl, or bound together to form a 5 membered ring as in $R_{4-5}$:

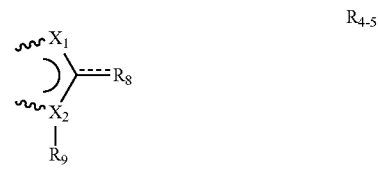

the binding being achieved at the bonds indicated by a $\sim\!\!\sim$ $X_1$ and $X_2$ are each independently N, C, O, or S;

$R_8$ is H, halo, $-OH$, $C_{1-6}$ alkyl, $C_{2-6}$ alkenyl, $C_{2-6}$ alkynyl, $-OH$, $-NR_aR_b$, $-(CH_2)_n-O-R_c$, $-O-(C_{1-6}$ alkyl), $-S(O)_pR_e$, or $-C(O)-R_d$;

$R_9$ is H, $C_{1-6}$ alkyl, substituted $C_{1-6}$ alkyl, heterocyclyl, substituted heterocyclyl or $R_{9a}$, wherein $R_{9a}$ is:

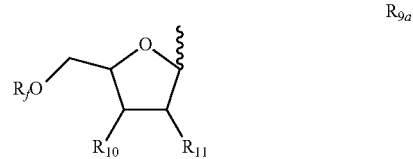

the binding being achieved at the bond indicated by a $\sim\!\!\sim$ $R_{10}$ and $R_{11}$ are each independently H, halo, $C_{1-6}$ alkoxy, substituted $C_{1-6}$ alkoxy, $-NR_aR_b$, or $-OH$;

each $R_a$ and $R_b$ is independently H, $C_{1-6}$ alkyl, substituted $C_{1-6}$ alkyl, $-C(O)R_d$, $C_{6-10}$ aryl;

each $R_c$ is independently H, phosphate, diphosphate, triphosphate, $C_{1-6}$ alkyl, or substituted $C_{1-6}$ alkyl;

each $R_d$ is independently H, halo, $C_{1-6}$ alkyl, substituted $C_{1-6}$ alkyl, $C_{1-6}$ alkoxy, substituted $C_{1-6}$ alkoxy, $-NH_2$, $-NH(C_{1-6}$ alkyl), $-NH($ substituted $C_{1-6}$ alkyl$)$, $-N(C_{1-6}$ alkyl$)_2$, $-N($ substituted $C_{1-6}$ alkyl$)_2$, $C_{6-10}$ aryl, or heterocyclyl;

each $R_e$ is independently H, $C_{1-6}$ alkyl, substituted $C_{1-6}$ alkyl, $C_{6-10}$ aryl, substituted $C_{6-10}$ aryl, heterocyclyl, or substituted heterocyclyl;

each $R_f$ is independently H, $C_{1-6}$ alkyl, substituted $C_{1-6}$ alkyl, $-C(O)R_d$, phosphate, diphosphate, or triphosphate;

each n is independently 0, 1, 2, or 3;
each p is independently 0, 1, or 2; or
or (g) a pharmaceutically acceptable salt of any of (a) to (f), a tautomer of any of (a) to (f), or a pharmaceutically acceptable salt of the tautomer.

P. Lipids Linked to a Phosphate-Containing Acyclic Backbone

Immunological adjuvants containing lipids linked to a phosphate-containing acyclic backbone include the TLR4 antagonist E5564 (Wong et al. (2003) *J. Clin. Pharmacol.* 43(7):735-742; US2005/0215517):

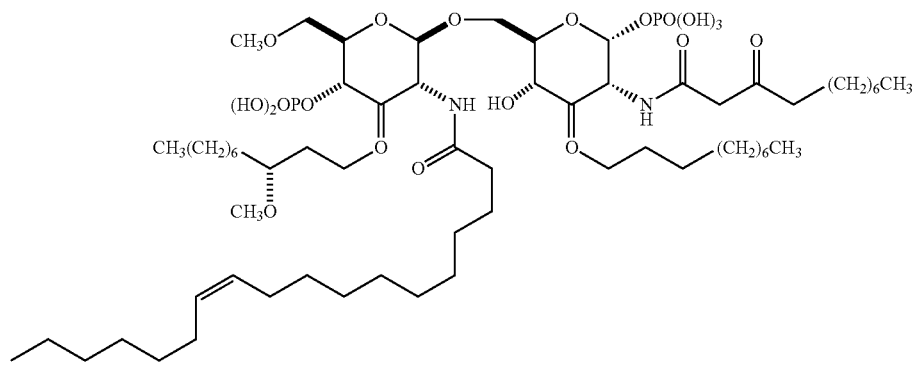

Q. Small Molecule Immunopotentiators (Smips)
SMIPs include:
N2-methyl-1-(2-methylpropyl)-1H-imidazo[4,5-c]quinoline-2,4-diamine;
N2,N2-dimethyl-1-(2-methylpropyl)-1H-imidazo[4,5-c]quinoline-2,4-diamine;
N2-ethyl-N2-methyl-1-(2-methylpropyl)-1H-imidazo[4,5-c]quinoline-2,4-diamine;
N2-methyl-1-(2-methylpropyl)-N2-propyl-1H-imidazo[4,5-c]quinoline-2,4-diamine;
1-(2-methylpropyl)-N2-propyl-1H-imidazo[4,5-c]quinoline-2,4-diamine;
N2-butyl-1-(2-methylpropyl)-1H-imidazo[4,5-c]quinoline-2,4-diamine;
N2-butyl-N2-methyl-1-(2-methylpropyl)-1H-imidazo[4,5-c]quinoline-2,4-diamine;
N2-methyl-1-(2-methylpropyl)-N2-pentyl-1H-imidazo[4,5-c]quinoline-2,4-diamine;
N2-methyl-1-(2-methylpropyl)-N2-prop-2-enyl-1H-imidazo[4,5-c]quinoline-2,4-diamine;
1-(2-methylpropyl)-2-[(phenylmethyl)thio]-1H-imidazo[4,5-c]quinolin-4-amine;
1-(2-methylpropyl)-2-(propylthio)-1H-imidazo[4,5-c]quinolin-4-amine;
2-[[4-amino-1-(2-methylpropyl)-1H-imidazo[4,5-c]quinolin-2-yl](methyl)amino]ethanol;
2-[[4-amino-1-(2-methylpropyl)-1H-imidazo[4,5-c]quinolin-2-yl](methyl)amino]ethyl acetate;
4-amino-1-(2-methylpropyl)-1,3-dihydro-2H-imidazo[4,5-c]quinolin-2-one;
N2-butyl-1-(2-methylpropyl)-N4,N4-bis(phenylmethyl)-1H-imidazo[4,5-c]quinoline-2,4-diamine;
N2-butyl-N2-methyl-1-(2-methylpropyl)-N4,N4-bis(phenylmethyl)-1H-imidazo[4,5-c]quinoline-2,4-diamine;
N2-methyl-1-(2-methylpropyl)-N4,N4-bis(phenylmethyl)-1H-imidazo[4,5-c]quinoline-2,4-diamine;
N2,N2-dimethyl-1-(2-methylpropyl)-N4,N4-bis(phenylmethyl)-1H-imidazo[4,5-c]quinoline-2,4-diamine;
1-{4-amino-2-[methyl(propyl)amino]-1H-imidazo[4,5-c]quinolin-1-yl}-2-methylpropan-2-ol;
1-[4-amino-2-(propylamino)-1H-imidazo[4,5-c]quinolin-1-yl]-2-methylpropan-2-ol;
N4,N4-dibenzyl-1-(2-methoxy-2-methylpropyl)-N2-propyl-1H-imidazo[4,5-c]quinoline-2,4-diamine.

R. Proteosomes

One adjuvant is an outer membrane protein proteosome preparation prepared from a first Gram-negative bacterium in combination with a liposaccharide preparation derived from a second Gram-negative bacterium, wherein the outer membrane protein proteosome and liposaccharide preparations form a stable non-covalent adjuvant complex. Such complexes include "IVX-908", a complex comprised of *Neisseria meningitidis* outer membrane and lipopolysaccharides. They have been used as adjuvants for influenza vaccines (WO02/072012).

S. Lipeptides

Lipopeptides (i.e., compounds comprising one or more fatty acid residues and two or more amino acid residues) are also known to have immunostimulating character. Lipopeptides based on glycerylcysteine are of particularly suitable for use as adjuvants. Specific examples of such peptides include compounds of the following formula

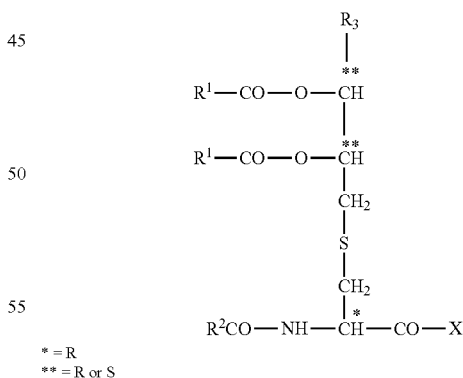

* = R
** = R or S in which each of $R^1$ and $R^2$ represents a saturated or unsaturated, aliphatic or mixed aliphatic-cycloaliphatic hydrocarbon radical having from 8 to 30, preferably 11 to 21, carbon atoms that is optionally also substituted by oxygen functions, $R^3$ represents hydrogen or the radical $R_1$—CO—O—CH$_2$— in which $R^1$ has the same meaning as above, and X represents an amino acid bonded by a peptide linkage and having a free, esterified or amidated carboxy group, or an amino acid sequence of from 2 to 10 amino acids of which the terminal carboxy group is in free, esterified or amidated form. In certain embodiments, the amino acid sequence comprises a D-amino acid, for example, D-glutamic acid (D-Glu) or D-gamma-carboxy-glutamic acid (D-Gla).

Bacterial lipopeptides generally recognize $TLR^2$, without requiring $TLR^6$ to participate. (TLRs operate cooperatively to provide specific recognition of various triggers, and TLR2 plus TLR6 together recognize peptidoglycans, while TLR2 recognizes lipopeptides without TLR6.) These are sometimes classified as natural lipopeptides and synthetic lipopeptides. Synthetic lipopeptides tend to behave similarly, and are primarily recognized by TLR2.

Lipopeptides suitable for use as adjuvants include compounds of Formula I:

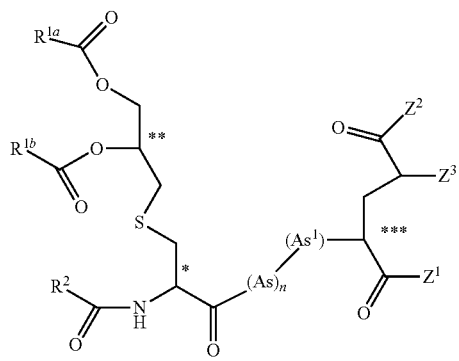

$R^2$ is an aliphatic or cycloaliphatic hydrocarbon group having 1-21 carbon atoms and optionally substituted by oxygen functions;

n is 0 or 1;

As represents either —O-Kw-CO— or —NH-Kw-CO—, where Kw is an aliphatic hydrocarbon group having 1-12 carbon atoms;

$As^1$ is a D- or L-alpha-amino acid;

$Z^1$ and $Z^2$ each independently represent —OH or the N-terminal radical of a D- or L-alpha amino acid of an amino-(lower alkane)-sulfonic acid or of a peptide having up to 6 amino acids selected from the D- and L-alpha aminocarboxylic acids and amino-lower alkyl-sulfonic acids; and $Z^3$ is H or —CO—$Z^4$, wher $Z^4$ is —OH or the N-terminal radical of a D- or L-alpha amino acid of an amino-(lower alkane)-sulfonic acid or of a peptide having up to 6 amino acids selected from the D and L-alpha aminocarboxylic acids and amino-lower alkyl-sulfonic acids; or an ester or amide formed from the carboxylic acid of such compounds. Suitable amides include —$NH_2$ and NH (lower alkyl), and suitable esters include C1-C4 alkyl esters. (lower alkyl or lower alkane, as used herein, refers to C1-C6 straight chain or branched alkyls).

Such compounds are described in more detail in U.S. Pat. No. 4,666,886. In one preferred embodiment, the lipopeptide is of the following formula:

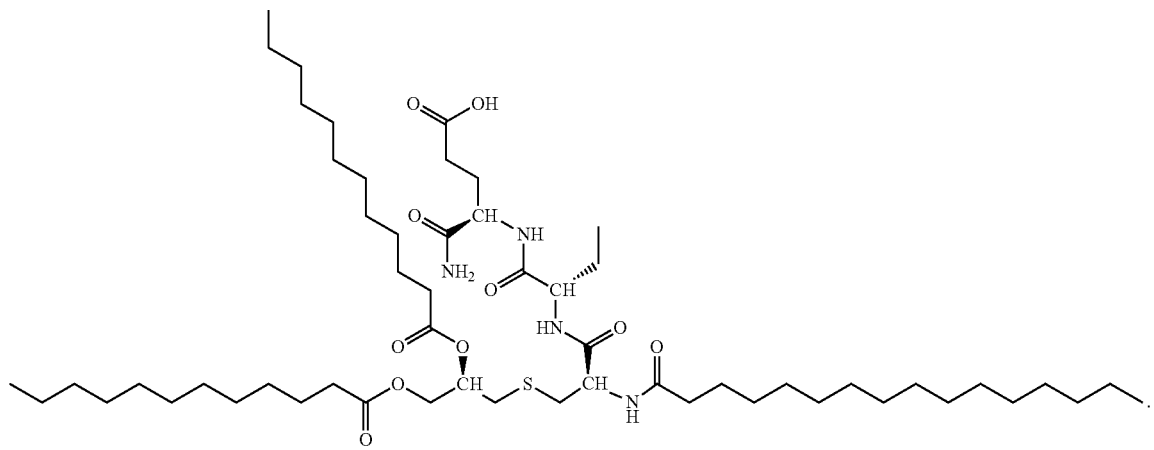 [SMILES: CCCCCCCCCCCCCCCC(=O)N[C@@H](CSC[C@@H](COC(=O)CCCCCCCCCCC)OC(=O)CCCCCCCCCCC)C(=O)N[C@@H](CC)C(=O)N[C@H](CCC(=O)O)C(N)=O]

where the chiral center labeled * and the one labeled * * * are both in the R configuration;

the chiral center labeled ** is either in the R or S configuration;

each $R^{1a}$ and $R^{1b}$ is independently an aliphatic or cycloaliphatic-aliphatic hydrocarbon group having 7-21 carbon atoms, optionally substituted by oxygen functions, or one of $R^{1a}$ and $R^{1b}$, but not both, is H;

Another example of a lipopeptide species is called LP40, and is an agonist of TLR2. Akdis, et al., Eur. J. Immunology, 33: 2717-26 (2003).

These are related to a known class of lipopeptides from E. coli, referred to as murein lipoproteins. Certain partial degradation products of those proteins called murein lipopetides are described in Hantke, et al., Eur. J. Biochem., 34: 284-296 (1973). These comprise a peptide linked to N-acetyl muramic acid and are thus related to Muramyl peptides, which are described in Baschang, et al., *Tetrahedron*, 45(20): 6331-6360 (1989).

T. Benzonaphthyridines

Examples of benzonaphthyridine compounds suitable for use as adjuvants in the invention are described in WO 2009/111337.

U. Other Adjuvants

Other substances that act as immunological adjuvants are disclosed in Burdman, J. R. et al. (eds) (1995) (*Vaccine Design: Subunit and Adjuvant Approach* (Springer) (Chapter 7) and O'Hagan, D. T. (2000) (*Vaccine Adjuvants: Preparation Methods and Research Protocols* (Humana Press) (Volume 42 of *Methods in Molecular Medicine* series)).

Further useful adjuvant substances include:

Methyl inosine 5'-monophosphate ("MIMP") (Signorelli & Hadden (2003) *Int. Immunopharmacol.* 3(8):1177-1186).

A polyhydroxlated pyrrolizidine compound (WO2004/064715), such as one having formula:

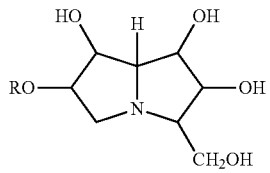

where R is selected from the group comprising hydrogen, straight or branched, unsubstituted or substituted, saturated or unsaturated acyl, alkyl (e.g. cycloalkyl), alkenyl, alkynyl and aryl groups, or a pharmaceutically acceptable salt or derivative thereof. Examples include, but are not limited to: casuarine, casuarine-6-α-D-glucopyranose, 3-epi-casuarine, 7-epi-casuarine, 3,7-diepicasuarine, etc.

A gamma inulin (Cooper (1995) *Pharm. Biotechnol.* 6:559-580) or derivative thereof, such as algammulin.

Compounds disclosed in PCT/US2005/022769.

Compounds disclosed in WO2004/87153, including: Acylpiperazine compounds, Indoledione compounds, Tetrahydraisoquinoline (THIQ) compounds, Benzocyclodione compounds, Aminoazavinyl compounds, Aminobenzimidazole quinolinone (ABIQ) compounds (U.S. Pat. No. 6,605,617; WO 02/18383), Hydrapthalamide compounds, Benzophenone compounds, Isoxazole compounds, Sterol compounds, Quinazilinone compounds, Pyrrole compounds (WO2004/018455), Anthraquinone compounds, Quinoxaline compounds, Triazine compounds, Pyrazalopyrimidine compounds, and Benzazole compounds (WO03/082272).

Loxoribine (7-allyl-8-oxoguanosine) (U.S. Pat. No. 5,011,828).

A formulation of a cationic lipid and a (usually neutral) co-lipid, such as aminopropyl-dimethyl-myristoleyloxy-propanaminium bromide-diphytanoylphosphatidyl-ethanolamine ("Vaxfectin™") or aminopropyl-dimethyl-bis-dodecyloxy-propanaminium bromide-dioleoylphosphatidyl-ethanolamine ("GAP-DLRIE: DOPE"). Formulations containing (±)—N-(3-aminopropyl)-N,N-dimethyl-2,3-bis(syn-9-tetradeceneyloxy)-1-propanaminium salts are preferred (U.S. Pat. No. 6,586,409).

The invention may also comprise combinations of aspects of one or more of the immunological adjuvants identified above. For example, the following adjuvant compositions may be used in the invention: (1) a saponin and an oil-in-water emulsion (WO 99/11241); (2) a saponin (e.g., QS21)+a non-toxic LPS derivative (e.g. 3dMPL) (see WO 94/00153); (3) a saponin (e.g., QS21)+a non-toxic LPS derivative (e.g. 3dMPL)+a cholesterol; (4) a saponin (e.g., QS21)+3dMPL+IL-12 (optionally +a sterol) (WO 98/57659); (5) combinations of 3dMPL with, for example, QS21 and/or oil-in-water emulsions (see EP 0 835 318; EP 0 735 898; and EP 0 761 231); (6) SAF, containing 10% Squalane, 0.4% Tween 80, 5% pluronic-block polymer L121, and thr-MDP, either microfluidized into a submicron emulsion or vortexed to generate a larger particle size emulsion; (7) Ribi™ adjuvant system (RAS), (Ribi Immunochem, Hamilton, Mont.) containing 2% Squalene, 0.2% Tween 80, and one or more bacterial cell wall components from the group consisting of monophosphorylipid A (MPL), trehalose dimycolate (TDM), and cell wall skeleton (CWS), preferably MPL+CWS (Detox™); (8) one or more mineral salts (such as an aluminum salt)+a non-toxic derivative of LPS (such as 3dPML); (9) one or more mineral salts (such as an aluminum salt)+an immunostimulatory oligonucleotide (such as a nucleotide sequence including a CpG motif).

5. Additional Components

As previously noted, particle compositions in accordance with the invention can include additional components. Such additional components include, for example, components that prevent substantial particle agglomeration from occurring when microparticle suspensions in accordance with the invention are lyophilized and subsequently resuspended.

Additional components include (a) amino acids such as glutamic acid and arginine, among others; (b) polyols, including diols such as ethylene glycol, propanediols such as 1,2-propylene glycol and 1,3-propylene glycol, and butane diols such as 2,3-butylene glycol, among others, triols such as glycerol, among others, as well as other higher polyols; (c) carbohydrates including, for example, (i) monosaccharides (e.g., glucose, galactose, and fructose, among others), (ii) polysaccharides including disaccharides (e.g., sucrose, lactose, trehalose, maltose, gentiobiose, cellobiose, carboxymethyl cellulose and sorbitol, among others), trisaccharides (e.g., raffinose, among others), tetrasaccharides (e.g., stachyose among others), pentasaccharides (e.g., verbascose among others), as well as numerous other higher polysaccharides, and (iii) alditols such as xylitol, sorbitol, and mannitol, among others (in this regard, is noted that alditols are higher polyols, as well as being carbohydrates); and (d) nonionic surfactants such as polyvinyl alcohol (PVA), povidone (also known as polyvinylpyrrolidone or PVP), sorbitan esters, polysorbates, polyoxyethylated glycol monoethers, polyoxyethylated alkyl phenols, poloxamers, polyethylene glycol, and polypropylene glycol, among others.

Compositions in accordance with the invention can contain varying amounts of such additional components, where provided, typically depending on the amount that is effective to prevent substantial particle agglomeration from occurring when the lyophilized compositions of the invention are resuspended without affecting RNA adsorption and integrity.

In certain preferred embodiments, compositions in accordance with the invention will contain one, two or all of the following additional components in the following amounts: (a) non-ionic surfactant (e.g., PVA) in an amount ranging from 0.5 to 20% w/w (e.g., ranging from 0.5 to 1 to 2 to 10 to 15 to 20% w/w) relative to the amount of polymer (e.g., PLG) in the composition; (b) polyol (e.g, an alditol such as mannitol) in an amount ranging from 0.5 to 10% w/v (e.g., ranging from 0.5 to 1 to 2 to 5 to 10% w/v) relative to the reconstituted volume of the composition, and (c) carbohydrate (e.g., a saccharide such as sucrose) in an amount ranging from 0.5 to 10% w/v (e.g., ranging from 0.5 to 1 to 2 to 5 to 10% w/v) relative to the reconstituted volume of the composition. As noted below, lyophilized compositions in accordane with the present invention may be provided with instructions regarding the proper volume of fluid (e.g, water for injection, etc.) to be used for resuspension/reconstitution of the composition.

6. Further Excipients

As discussed above, one or more additional pharmaceutically acceptable excipients such as biological buffering substances, tonicity adjusting agents, and the like, may also be present in the particle compositions of the present invention.

7. Administration

Once formulated (and resuspended as necessary), the particle compositions of the invention can be administered parenterally, e.g., by injection (which may be needleless), among other routes of administration. In this regard, the particle compositions are typically supplied lyophilized in a vial or other container which is supplied with a septum or other suitable means for supplying a resuspension medium (e.g., Water for Injection) and for withdrawing the resultant suspension. A suitable syringe may also be supplied for injection. The compositions can be injected subcutaneously, intradermally, intramuscularly, intravenously, intraarterially, or intraperitoneally, for example. Other modes of administration include nasal, mucosal, intraoccular, rectal, vaginal, oral and pulmonary administration, and transdermal or transcutaneous applications.

In some embodiments, the compositions of the present invention can be used for site-specific targeted delivery. For example, intravenous administration of the compositions can be used for targeting the lung, liver, spleen, blood circulation, or bone marrow.

Treatment may be conducted according to a single dose schedule or a multiple dose schedule. A multiple dose schedule is one in which a primary course of administration may be given, for example, with 1-10 separate doses, followed by other doses given at subsequent time intervals, chosen to maintain and/or reinforce the therapeutic response, for example at 1-4 months for a second dose, and if needed, a subsequent dose(s) after several months. The dosage regimen will also be, at least in part, determined by the need of the subject and be dependent on the judgment of the practitioner.

Furthermore, if prevention of disease is desired, the compositions are generally administered prior to the arrival of the primary occurrence of the infection or disorder of interest. If other forms of treatment are desired, e.g., the reduction or elimination of symptoms or recurrences, the compositions are generally administered subsequent to the arrival of the primary occurrence of the infection or disorder of interest.

7. Kits

This invention encompasses kits which can simplify the administration of appropriate amounts of immunological compositions to a subject.

A typical kit of the invention comprises a unit dosage form of a lyophilized particle composition in accordance with the invention (i.e., one comprising, inter alia, an RNA replicon adsorbed to positively charged particles), preferably in a sealed container.

In certain embodiments, such a sealed container may be provided along with a label indicating one or more members of the group consisting of the following: (a) storage information, (b) dosing information, and (c) instructions regarding how to administer the microparticle formation. For lyophilized compositions, the instructions will typically include the volume of fluid (e.g., water for injection, etc.) to be used for resuspension/reconstitution of the composition. In some instances, the sealed container and label may be contained within a suitable packaging material.

Kits of the invention can further comprise a sealed container which contains one or more immunological adjuvants. The adjuvants may be in lyophilized form or provided in the form of an aqueous fluid.

Kits of the invention can further comprise a sealed container which contains a pharmaceutically acceptable vehicle that can be used to suspend and administer the lyophilized particle composition and in some embodiments to suspend/dissolve any adjuvant composition that is supplied.

The kit may further include one or more devices that can be used to administer the compositions of the invention to a vertebrate subject. Examples of such devices include, but are not limited to, syringes, drip bags, and inhalers.

For instance, a syringe may be used to introduce a suitable pharmaceutically acceptable vehicle (e.g., Water for Injection) to a lyophilized particle composition in accordance with the invention (i.e., one comprising, inter alia, an RNA replicon adsorbed to positively charged particles). The resulting particle-containing suspension may then be withdrawn from the container and administered to a subject.

C. EXPERIMENTAL

Below are examples of specific embodiments for carrying out the present invention. The examples are offered for illustrative purposes only, and are not intended to limit the scope of the present invention in any way.

Efforts have been made to ensure accuracy with respect to numbers used (e.g., amounts, temperatures, etc.), but some experimental error and deviation should, of course, be allowed for.

Example 1

RNA Synthesis

Plasmid DNA encoding alphavirus replicons served as a template for synthesis of RNA in vitro. Plasmid encoding pT7-mVEEV-FL.RSVF (A317) is set forth in FIG. 1 (SEQ ID NO:1); plasmid encoding pT7-mVEEV-SEAP (A306) is set forth in FIG. 2 (SEQ ID NO:2); and plasmid encoding VEE/SIN self-replicating RNA containing full length RSV-F and SP6 promoter (A4) is set forth in FIG. 3 (SEQ ID NO:3). Replicons contain the genetic elements required for RNA replication but lack those encoding gene products necessary for particle assembly; the structural genes of the alphavirus genome are replaced by sequences encoding a heterologous protein. Upon delivery of the replicons to eukaryotic cells, the positive-stranded RNA is translated to produce four non-structural proteins, which together replicate the genomic RNA and transcribe abundant subgenomic mRNAs encoding the heterologous gene product. Due to the lack of expression of the alphavirus structural proteins, replicons are incapable of inducing the generation of infectious particles. A bacteriophage (T7 or SP6) promoter upstream of the alphavirus cDNA facilitates the synthesis of the replicon RNA in vitro and the hepatitis delta virus (HDV) ribozyme immediately downstream of the poly(A)-tail generates the correct 3'-end through its self-cleaving activity.

Following linearization of the plasmid DNA downstream of the HDV ribozyme with a suitable restriction endonuclease, run-off transcripts were synthesized in vitro using T7 or SP6 bacteriophage derived DNA-dependent RNA polymerase. Transcriptions were performed for 2 hours at 37° C.

in the presence of 7.5 mM (T7 RNA polymerase) or 5 mM (SP6 RNA polymerase) of each of the nucleoside triphosphates (ATP, CTP, GTP and UTP) following the instructions provided by the manufacturer (Ambion, Austin, Tex.). Following transcription, the template DNA was digested with TURBO DNase (Ambion, Austin, Tex.). The replicon RNA was precipitated with LiCl and reconstituted in nuclease-free water. To generate capped RNAs, in vitro transcription reactions were supplemented with 6 mM (T7 RNA polymerase) or 4 mM (SP6 RNA polymerase) RNA cap structure analog (New England Biolabs, Beverly, Mass.) while lowering the concentration of GTP to 1.5 mM (T7 RNA polymerase) or 1 mM (SP6 RNA polymerase). Alternatively, uncapped RNA was capped post-transcripionally with Vaccinia Capping Enzyme (VCE) using the ScriptCap m$^7$G Capping System (Epicentre Biotechnologies, Madison, Wis.) as outlined in the user manual. Post-transcriptionally capped RNA was precipitated with LiCl and reconstituted in nuclease-free water. The concentration of the RNA samples was determined by measuring the optical density at 260 nm. Integrity of the in vitro transcripts was confirmed by denaturing agarose gel electrophoresis.

Example 2

DOTAP Liposome Formation

For formation of DOTAP liposomes, 24 mg of DOTAP (Lipoid, Ludwigshafen Germany) was dissolved in 10 mL dichloromethane and added to 40 mL water with 0.25% w/v PVA. The mixture was homogenized using Omni Macro homogenizer (Omni International) at 12,900 rpm for 10 min. The resulting emulsion was stirred at 1000 rpm for 2 hours in a ventilated fume hood to evaporate dichloromethane. 10 mL of liposomes were dialyzed against 2 L water overnight at room temperature using 100 kDa molecular weight cut-off membranes (Spectrum Laboratories, USA). Dialyzed liposomes were stored at 2-8° C.

Example 3

PLG Microparticle Formation

For the formation of PLG microparticles, 0 mg (0% w/w), 6 mg (1% w/w), 24 mg (4% w/w) or 60 mg (10% w/w) of DOTAP was dissolved along with 600 mg RG503 PLG (Boehringer Ingelheim, USA) in 10 mL dichloromethane and added to 40 mL water with 0.25% w/v PVA. The mixture was homogenized using an Omni Macro homogenizer (Omni International) at 12,900 rpm for 10 min. The resulting emulsion was stirred at 1000 rpm for 2 hours in a ventilated fume hood to evaporate dichloromethane. 10 mL of PLG microparticles were dialyzed against 2 L water overnight at room temperature using 100 kDa molecular weight cut-off membranes (Spectrum Laboratories, USA). Dialyzed PLG microparticles were stored at 2-8° C.

For the evaluation of different cationic surfactants, 24 mg of DDA (Avanti Polar Lipids, USA) or DC-Cholesterol (Avanti Polar Lipids, USA) were used in place of DOTAP as described for the 4% w/w formulation above.

Example 4

RNA Adsorption to Microparticles and Liposomes

For RNA adsorption in Example 10 below, 100 µL of 100 µg/mL of A306 RNA (Example 1, FIG. 2, SEQ ID NO:2) was added dropwise to 1.4 mL (1% w/w), 350 µL (4% w/w), or 140 µL (10% w/w) of PLG microparticles. In case of 0% w/w PLG microparticles, 350 µL of PLG microparticles were pre-incubated with 350 µL of DOTAP liposomes (see Example 2 above) for 30 minutes, followed by RNA addition. The sample was allowed to sit at room temperature for 30 min. To each vial, 300 µL 15% w/v mannitol and 100 µL 15% w/v sucrose were added, and the sample was lyophilized overnight using benchtop lyophilizer (LabConco, USA). The lyophilized vials were stored at 2-8° C.

The N:P (Nitrogen to Phosphate) ratio is calculated as follows: The protonated nitrogen on the cationic surfactant (i.e., DOTAP, DDA or DC-Cholesterol) and phosphates on the RNA are used for this calculation. Each 1 µg of self-replicating RNA molecule was assumed to contain 3 nmoles of anionic phosphate, each 1 µg of DOTAP was assumed to contain 1.4 nmoles of cationic nitrogen, each 1 µg of DDA was assumed to contain 1.6 nmoles of cationic nitrogen, and each 1 µg of DC-cholesterol was assumed to contain 1.9 nmoles of cationic nitrogen.

Based on PLG recovery, in Example 13, 12 µg A4 RNA (Example 1, FIG. 3, SEQ ID NO:3) was adsorbed to PLG microparticles at different N:P ratios using 470 µL (N:P=10: 1), 187 µL (N:P=4:1) or 12 µL (N:P=1:4) of 4% w/w PLG/DOTAP; using 346 µL (N:P=10:1), 138 µL (N:P=4:1) or 9 µL (N:P=1:4) of 4% w/w PLG/DDA; and using 335 µL (N:P=10: 1), 134 µL (N:P=4:1) or 8 µL (N:P=1:4) of 4% w/w PLG/DC-Cholesterol. The formulations were lyophilized as described above.

For RNA adsorption at N:P ratio of 10:1 using DOTAP liposomes in Example 10, 100 µL of 100 µg/mL of RNA was added dropwise to 350 µL DOTAP liposomes (see Example 2 above). The sample was allowed to sit at room temperature for 30 min. To each vial, 300 µL 15% w/v mannitol and 100 µL 15% w/v sucrose were added, and the sample was lyophilized overnight using benchtop lyophilizer (LabConco, USA). The lyophilized vials were stored at 2-8° C.

Example 5

PLG Nanoparticle Formation

Positively charged PLG nanoparticles containing a biodegradable polymer and a cationic surfactant were formed using the solvent extraction method. Specifically, 500 mg of RG503 PLG and 5 mg (1% w/w) or 20 mg (4% w/w) of DOTAP were dissolved in 50 mL acetone (Type I). For ethyl acetate-based PLG nanoparticle (Type II), 500 mg of RG503 PLG and 20 mg (4% w/w) of DOTAP were dissolved in 50 mL ethyl acetate. The PLG/DOTAP solution was added dropwise to 50 mL water with homogenization using Omni Macro Homogenizer (Omni International) at 1000 rpm. After complete addition, homogenization speed was increased to 6000 rpm for 30 seconds. Particle suspension was shaken at 150 rpm overnight on a DS-500 Orbital Shaker (VWR International, USA) to evaporate acetone or ethyl acetate. Particle suspension was filtered using 40 µm sterile cell strainer (BD Biosciences, USA) to remove large aggregates.

Two batches of 4% w/w PLG/DOTAP nanoparticles were prepared using the above procedure with acetone solvent. Each batch was characterized for particle size and zeta potential as described in Example 7 below. Batch #1 (used in Example 10) and Batch #2 (used in Example 11) had Z average particle sizes of 220 and 194 nm, respectively, and zeta potentials of +57.7 and +66.8 mV, respectively.

Example 6

RNA Adsorption to Nanoparticles

Based on PLG recovery of nanoparticles, for RNA adsorption in Examples 10 and 11 at N:P ratio of 10:1, 100 µL of 100 µg/mL of RNA was added dropwise to 3.2 mL (1% w/w) or 800 µL (4% w/w) of PLG nanoparticles from Example 5. To each vial, 300 µL 15% w/v mannitol, 100 µL 15% w/v sucrose, and 25 µL (1% w/w) or 6 µL (4% w/w) of 4% w/v PVA were added, and the sample was lyophilized overnight using benchtop lyophilizer (LabConco, USA). The excipients corresponded to 4.5% w/v of mannitol and 1.5% w/v of sucrose in the final reconstitution volume, and 10% w/w of PVA. The lyophilized vials were stored at 2-8° C.

Example 7

Particle Size and Zeta Potential Measurement

Particle size of DOTAP liposomes and nanoparticles were measured using a Zetasizer Nano ZS (Malvern Instruments, Worcestershire, UK) according to the manufacturer's instructions. Particle sizes are reported as the Z-Average (ZAve), along with the polydispersity index (pdi). All samples were diluted 50-fold in water prior to measurements.

Particle size of microparticles was measured using a Horiba LA-930 particle sizer (Horiba Scientific, USA). Microparticle samples were diluted 200-fold prior to measurements. Particle size is reported as D(v,0.5) (designated "D50" in Table 2 below) and D(v,0.9) (designated "D90" in Table 2 below).

Zeta potential for both microparticles and nanoparticles was measured using Zetasizer Nano ZS using 50-fold diluted samples according to the manufacturer's instructions.

Example 8

Gel electrophoresis

Denaturing gel electrophoresis was performed to evaluate the integrity of the RNA after the formulation process and to assess the RNAse protection of the adsorbed RNA. The gel was cast as follows: 0.4 g of agarose (Bio-Rad, Hercules, Calif.) was added to 36 ml of DEPC treated water and heated in a microwave until dissolved and then cooled until warm. 4 ml of 10× denaturing gel buffer (Ambion, Austin, Tex.), was then added to the agarose solution. The gel was poured and was allowed to set for at least 30 minutes at room temperature. The gel was then placed in a gel tank, and 1× Northernmax running buffer (Ambion, Austin, Tex.) was added to cover the gel by a few millimeters.

Example 9

RNase Protection Assay

An RNase protection assay was performed for microparticles and nanoparticles with adsorbed A4 RNA (Example 1, FIG. 3, SEQ ID NO:3) and A306 RNA (Example 1, FIG. 2, SEQ ID NO:2), respectively. RNase digestion was achieved by incubation of PLG microparticles from Example 4 (used in Example 13) and PLG nanoparticles from Example 6 (used in Example 11) with 3.8 mAU of RNase A per microgram of RNA (Ambion, Hercules, and CA) for 30 minutes at room temperature. RNase was inactivated with Protenase K (Novagen, Darmstadt, Germany) by incubating the sample at 55° C. for 10 minutes. Post RNase inactivation, 1000 µg of heparin sulfate per microgram of RNA was added to desorb the RNA from the PLG particles into the aqueous phase. As a control for each sample, RNA was desorbed from untreated PLG particles using 1000 µg heparin sulfate per µg of RNA to determine the integrity of adsorbed RNA. Samples were mixed by vortexing for a few seconds and then placed on a centrifuge for 15 minutes at 12k RPM.

To determine RNA adsorption efficiency, PLG particles without any treatment were centrifuged for 15 minutes at 12k rpm.

In all cases the supernatant was removed and used to analyze the RNA.

Figure 5:
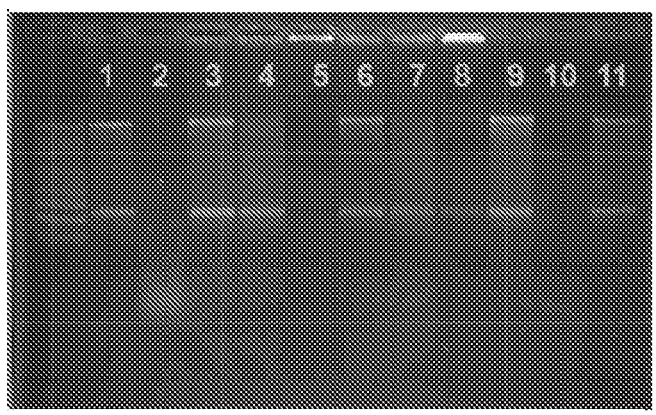

Prior to loading (400 ng RNA per well) (theoretical amount assuming all RNA is adsorbed and all is desorbed) all the samples were incubated with formaldehyde loading dye, denatured for 10 minutes at 65° C. and cooled to room temperature. Ambion Millennium markers were used to approximate the molecular weight of the RNA construct. The gel was run at 90 V. The gel was stained using 0.1% SYBR gold according to the manufacturer's guidelines (Invitrogen, Carlsbad, Calif.) in water by rocking at room temperature for 1 hour. Gel images were taken on a Bio-Rad Chemidoc XRS imaging system (Hercules, Calif.). RNAse protection assay gels for PLG nanoparticles and microparticles are shown in FIGS. 4 and 5, respectively. In FIG. 4, PLG nanoparticles were evaluated at N:P ratio of 10:1. In FIG. 5, microparticles were evaluated at N:P ratios of 10:1, 4:1 and 1:4.

The results in FIG. 4 show that RNA is completely adsorbed to PLG nanoparticles (Type I) and remains intact as shown by desorption using heparin sulfate and that the PLG nanoparticles (Type I) protect adsorbed RNA from degradation by RNAse. RNA was observed to be completely adsorbed to PLG nanoparticles (Type II) but did not desorb completely from PLG nanoparticles using heparin sulfate suggesting stronger adsorption of RNA to the Type II nanoparticles. These results demonstrate that PLG nanoparticles (Type I) adsorb RNA and protect RNA from degradation by RNAses.

FIG. 5 shows that RNA is completely adsorbed to PLG microparticles at N:P 10:1, partially adsorbed at N:P 4:1 and nearly completely unadsorbed at N:P 1:4. Upon desorption of RNA from PLG microparticles, RNA is shown to be intact at all N:P ratios. RNA adsorbed to PLG microparticles at N:P 10:1 and 4:1 showed protection when treated with RNAse whereas RNA adsorbed to PLG microparticles at N:P 1:4 was digested by RNAse. These results demonstrate that adsorption of RNA to PLG microparticles is necessary to provide protection against degradation by RNAse.

Example 10

Secreted Alkaline Phosphatase (SEAP) Assay I

To assess the kinetics and amount of antigen production in vivo, 1 µg (microgram) of an RNA replicon that expresses secreted alkaline phosphatase (SEAP) (Example 1, SEQ ID NO:2, also referred to as "A306" or "vA306") was administered with and without formulation to mice via intramuscularly injection. Groups of 5 female BALB/c mice aged 8-10 weeks and weighing about 20g were immunized.

Figure 6A:
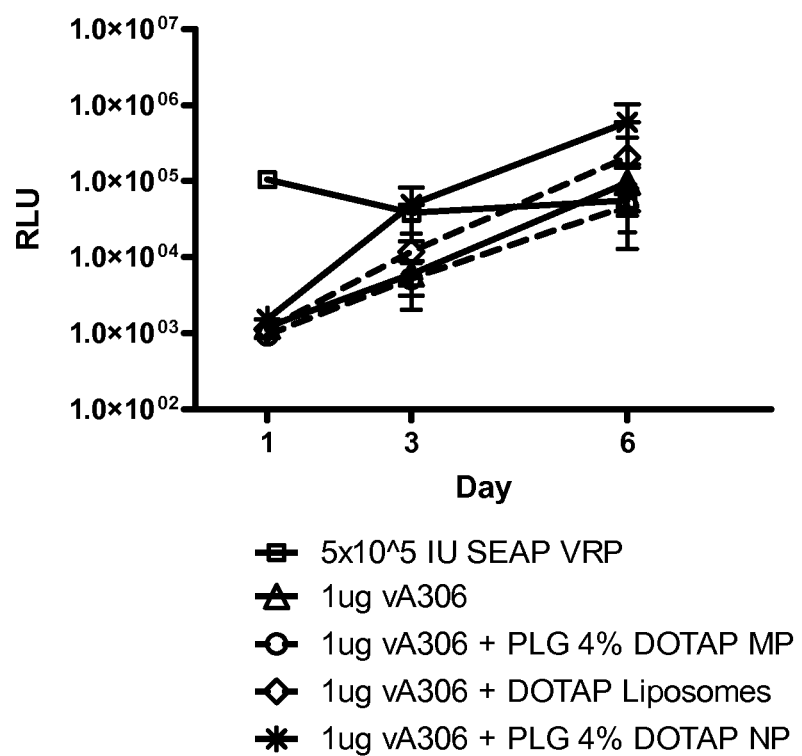
Figure 6B:
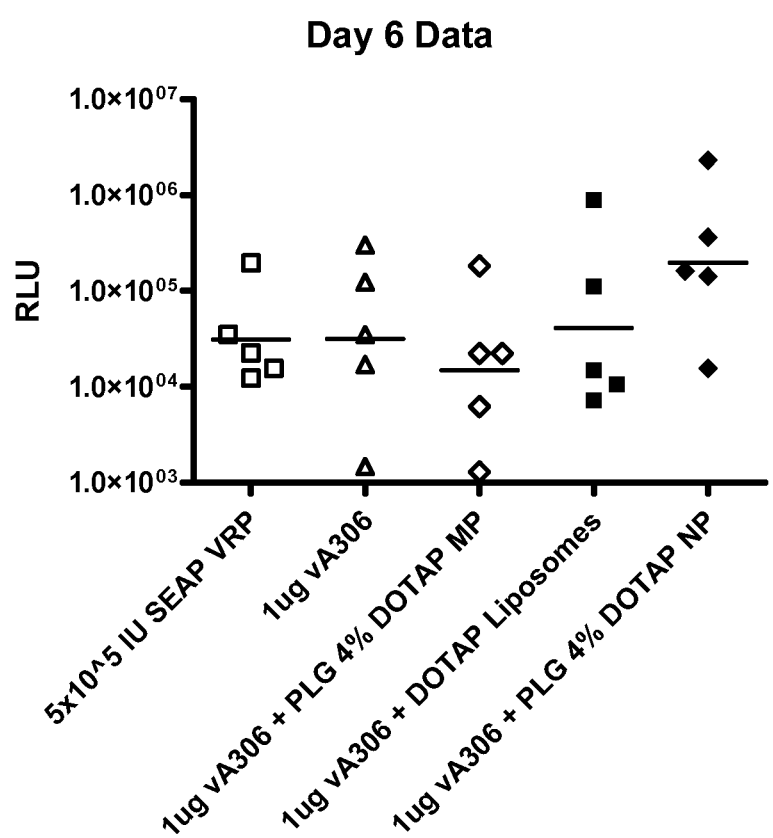

As a positive control, one group was injected with viral replicon particles (VRPs) at a dose of $5\times10^5$ infectious units (IU) (see Example 12) (designated "5×10^5 IU SEAP VRP" in FIGS. 6A-6B and "VRP" in Table 1).

In another group, naked self-replicating RNA was administered in RNase free 1×PBS (designated "vA306" in FIGS. 6A-6B and "Naked A306 RNA" in Table 1).

In a further group, self-replicating RNA was adsorbed to DOTAP liposomes prepared as described in Example 4 with an N:P ratio of 10:1 (designated "1 ug vA306+DOTAP Liposomes" in FIGS. 6A-6B and "DOTAP Liposomes" in Tables 1 and 2).

To evaluate the effect of PLG microparticles co-delivered with DOTAP liposomes, DOTAP liposomes were pre-incubated with 0% w/w PLG microparticles (no DOTAP) followed by RNA addition as described in Example 4 (designated "0% PLG MP+DOTAP Liposomes" in Table 1 and "0% PLG MP" in Table 2).

In other groups, PLG microparticles were used which contained DOTAP at different weight ratios to PLG, specifically, 1%, 4% and 10% w/w. PLG nanoparticles were also used which contained DOTAP at weight ratios to PLG of 1% and 4% w/w.

In particular, groups of mice were injected with the following: (1) self-replicating RNA adsorbed to 1% w/w PLG/DOTAP microparticles prepared as described in Example 4 with a N:P ratio of 10:1 (designated "1% PLG MP" in Tables 1 and 2); (2) self-replicating RNA adsorbed to 4% w/w PLG/DOTAP microparticles prepared as described in Example 4 with a N:P ratio of 10:1 (designated "1 ug vA306+PLG 4% DOTAP MP" in FIGS. 6A-6B and "4% PLG MP" in Tables 1 and 2); (3) self-replicating RNA adsorbed to 10% w/w PLG/DOTAP microparticles prepared as described in Example 4 with a N:P ratio of 10:1 (designated "10% PLG MP" in Tables 1 and 2); (4) RNA adsorbed to 1% w/w PLG/DOTAP nanoparticles prepared as described in Example 6 with a N:P ratio of 10:1 using acetone as a solvent (designated "1% PLG NP" in Tables 1 and 2); and (5) RNA adsorbed to 4% w/w PLG/DOTAP nanoparticles prepared as described in Example 6 with a N:P ratio of 10:1 using acetone as a solvent (designated "1 ug vA306+PLG 4% DOTAP NP" in FIGS. 6A-6B and "4% PLG NP" in Tables 1 and 2).

A 100 µl dose was administered to each mouse (50 µl per site) in the quadriceps muscle. Blood samples were taken 1, 3, and 6 days post injection. Serum was separated from the blood immediately after collection, and stored at −30° C. until use.

A chemiluminescent SEAP assay Phospha-Light System (Applied Biosystems, Bedford, Mass.) was used to analyze the serum. Mouse sera were diluted 1:4 in 1× Phospha-Light dilution buffer. Samples were placed in a water bath sealed with aluminum sealing foil and heat inactivated for 30 minutes at 65° C. After cooling on ice for 3 minutes, and equilibrating to room temperature, 50 µL of Phospha-Light assay buffer was added to the wells and the samples were left at room temperature for 5 minutes. Then, 50 µL of reaction buffer containing 1:20 CSPD® (chemiluminescent alkaline phosphate substrate) substrate was added, and the luminescence was measured after 20 minutes of incubation at room temperature. Luminescence was measured on a Berthold Centro LB 960 luminometer (Oak Ridge, Tenn.) with a 1 second integration per well. The activity of SEAP in each sample was measured in duplicate and the mean of these two measurements taken.

Results are shown in FIGS. 6A-6B and Table 1. As seen from these data, serum SEAP levels increased when the RNA was adsorbed to PLG nanoparticles relative to the naked RNA control and PLG microparticles. SEAP expression on day 6 was increased when the RNA was adsorbed to PLG nanoparticles relative to the VRP control, but the kinetics of expression was very different.

TABLE 1

| Group | Dose (µg) | DAY 1 | DAY 3 | DAY 6 |
|---|---|---|---|---|
| VRP | $5 \times 10^5$ IU | 105,829 | 38,546 | 56,155 |
| Naked A306 RNA | 1 | 1,212 | 6,007 | 95,380 |
| 1% PLG MP | 1 | 1,103 | 10,083 | 109,168 |
| 4% PLG MP | 1 | 950 | 5,208 | 46,920 |
| 10% PLG MP | 1 | 1,222 | 6,775 | 137,121 |
| DOTAP Liposomes | 1 | 1,131 | 11,800 | 206,007 |
| 0% PLG MP + DOTAP Liposomes | 1 | 1,179 | 4,740 | 35,194 |
| 1% PLG NP | 1 | 990 | 4,117 | 64,765 |
| 4% PLG NP | 1 | 1,528 | 49,233 | 600,080 |

Particle size and zeta potential for several of the formulations was also measured as described in Example 7 and the results are shown in Table 2.

TABLE 2

| Group | ZAve for Nano-particles (nm) | D50/D90 (µm) (for Micro-particles) | PDI (for Nano-particles) | Zeta Potential (mV) |
|---|---|---|---|---|
| 0% PLG MP | N/A | 0.74/1.84 | N/A | N/A |
| 1% PLG MP | N/A | 0.60/0.92 | N/A | 48.9 |
| 4% PLG MP | N/A | 0.87/3.11 | N/A | 62.3 |
| 10% PLG MP | N/A | 0.77/2.66 | N/A | 66.3 |
| DOTAP Liposomes | 179.2 | | 0.303 | 43.8 |
| 1% PLG NP | 297.6 | | 0.201 | 26.4 |
| 4% PLG NP | 244.5 | | 0.127 | 57.7 |

As can be seen from the preceding data, the formulation process produced PLG nanoparticles with a typical mean particle size of ~200 nm and PLG microparticles with a median particle size of ~1 µm.

Example 11

Secreted Alkaline Phosphatase (SEAP) Assay II

As in Example 9, 1 µg (microgram) of an RNA replicon that expresses secreted alkaline phosphatase (SEAP) was administered with and without formulation to mice via intramuscularly injection. Groups of 5 female BALB/c mice aged 8-10 weeks and weighing about 20 g were immunized.

As a control, one group of mice was injected with naked self-replicating RNA in RNase free 1×PBS (designated "Naked A306 RNA" in Table 3). In other groups, formulations contained RNA adsorbed to PLG nanoparticles with DOTAP at weight ratio to PLG of 4% w/w (see Example 6). PLG nanoparticles that were evaluated in this study were synthesized using either acetone (Type I) or ethyl acetate (Type II) as organic solvent. RNA was adsorbed on all the evaluated formulations at N:P of 10:1.

A 100 µl dose was administered to each mouse (50 µl per site) in the quadriceps muscle. Blood samples were taken 1, 3, and 6 days post injection. Serum was separated from the blood immediately after collection, and stored at −30° C. until use. A chemiluminescent SEAP assay Phospha-Light System (Applied Biosystems, Bedford, Mass.) was used to analyze the serum. Results are shown in Table 3 and FIG. 7.

TABLE 3

| Group | Dose (µg) | DAY 1 | DAY 3 | DAY 6 |
|---|---|---|---|---|
| Naked A306 RNA | 1 | 1,164 | 6,435 | 41,668 |
| 4% PLG NP Type I | 1 | 998 | 9,423 | 108,888 |
| 4% PLG NP Type II | 1 | 1,206 | 2,091 | 3,069 |

Figure 7:
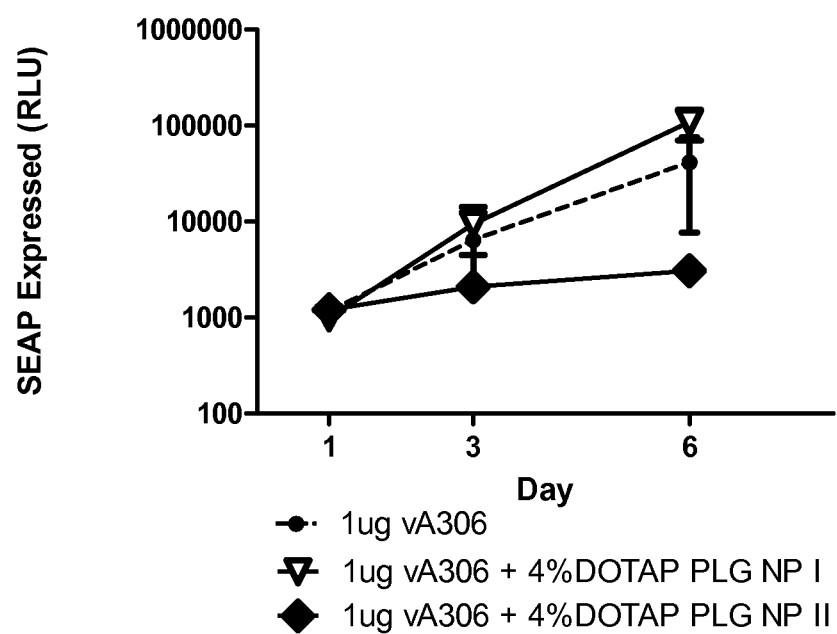
Figure 8A:
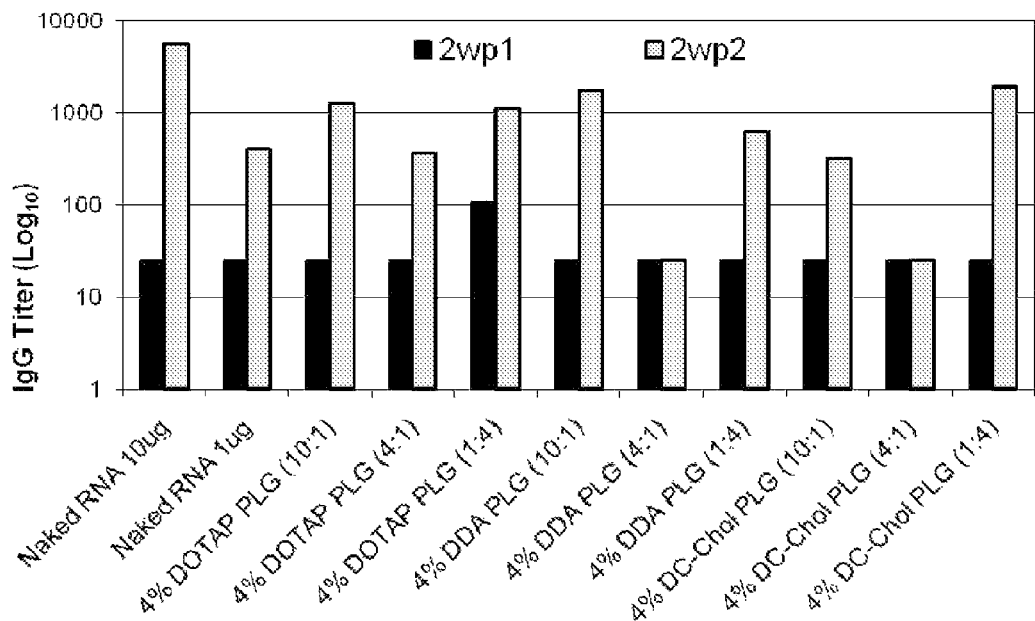
Figure 8B:
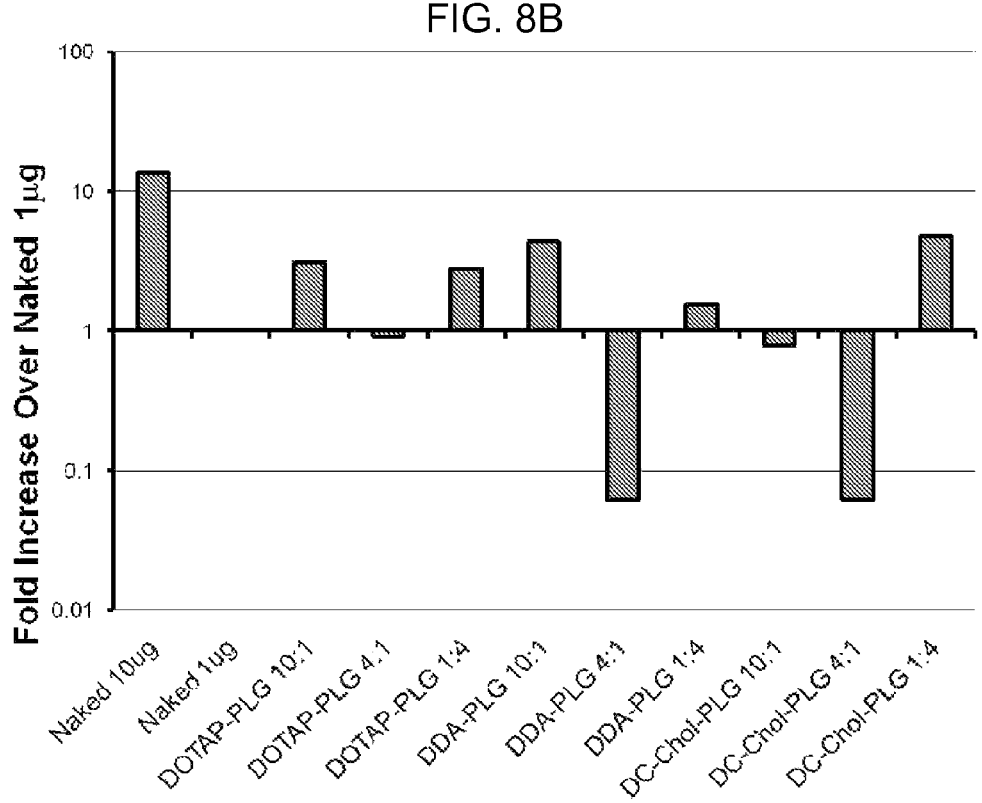

As see from Table 3 and FIG. 7, Serum SEAP levels increased when the RNA was adsorbed to Type I PLG nanoparticles relative to the naked RNA control and Type II PLG nanoparticles.

Particle size and zeta potential for the nanoparticle formulations was also measured as described in Example 7 and the results are shown in Table 4.

TABLE 4

| Group | ZAve for Nanoparticles (nm) | PDI (for Nanoparticles) | Zeta Potential (mV) |
|---|---|---|---|
| PLG Type I (Acetone) | 215.5 | 0.121 | 66.8 |
| PLG Type II (Ethyl Acetate) | 547.8 | 0.527 | 41.0 |

As see from Table 4, the formulation process produced PLG nanoparticles (synthesized using acetone) with a particle size of 200 nm (Type I). PLG nanoparticles synthesized using ethyl acetate had an initial particle size of 200 nm pre-lyophilization but aggregated to a particle size of 600 nm post-RNA adsorption and lyophilization (Type II).

Example 12

Viral Replicon Particles (VRP)

To compare RNA vaccines to traditional RNA-vectored approaches for achieving in vivo expression of reporter genes or antigens, we utilized viral replicon particles (VRPs) produced in BHK cells by the methods described by Perri et al., "An alphavirus replicon particle chimera derived from venezuelan equine encephalitis and sindbis viruses is a potent gene-based vaccine delivery vector," *J Virol* 77: 10394-10403 (2003). In this system, the antigen (or reporter gene) replicons consisted of alphavirus chimeric replicons (VCR) derived from the genome of Venezuelan equine encephalitis virus (VEEV) engineered to contain the 3'terminal sequences (3'UTR) of Sindbis virus and a Sindbis virus packaging signal (PS) (see FIG. 2 of Perri et al). These replicons were packaged into VRPs by co-electroporating them into baby hamster kidney (BHK) cells along with defective helper RNAs encoding the Sindbis virus capsid and glycoprotein genes (see FIG. 2 of Perri et al). The VRPs were then harvested and titrated by standard methods and inoculated into animals in culture fluid or other isotonic buffers.

Example 13

Murine Immunogenicity Studies

The A4 replicon that expresses the surface fusion glycoprotein of respiratory syncytial virus (RSV-F) was used for this experiment (Example 1, SEQ ID NO:3) also referred to as "A4". BALB/c mice, 10 animals per group, were given bilateral intramuscular vaccinations (50 µL per leg) on days 0 and 14 with the following: (1) naked self-replicating RNA (A4, 1 µg and 10 µg), and (2) PLG microparticle formulations (1 µg RNA/dose) prepared using particles synthesized using DOTAP, DDA or DC-Cholesterol at weight ratio to PLG of 4% w/w (see Example 3), followed by A4 RNA adsorption to these PLG microparticles at N:P ratios of 10:1, 4:1 and 1:4 (see Example 4). Serum was collected for antibody analysis on days 13 (2wp1) and 28 (2wp2).

Individual serum samples were assayed for the presence of RSV F-specific IgG by enzyme-linked immunosorbent assay (ELISA). ELISA plates (MaxiSorp 96-well, Nunc) were coated overnight at 4° C. with 1 µg/ml purified RSV F (delp23-furdel-trunc uncleaved) in PBS. After washing (PBS with 0.1% Tween-20), plates were blocked with Superblock Blocking Buffer in PBS (Thermo Scientific) for at least 1.5 hr at 37° C. The plates were then washed, serial dilutions of serum in assay diluent (PBS with 0.1% Tween-20 and 5% goat serum) from experimental or control cotton rats were added, and plates were incubated for 2 hr at 37° C. After washing, plates were incubated with horse radish peroxidase (HRP)-conjugated chicken anti-cotton rat IgG (Immunology Consultants Laboratory, Inc, diluted 1:5,000 in assay diluent) for 1 hr at 37° C. Finally, plates were washed and 100 µl of TMB peroxidase substrate solution (Kirkegaard & Perry Laboratories, Inc) was added to each well. Reactions were stopped by addition of 100 µl of 1M $H_3PO_4$, and absorbance was read at 450 nm using a plate reader. For each serum sample, a plot of optical density (OD) versus logarithm of the reciprocal serum dilution was generated by nonlinear regression (GraphPad Prism). Titers were defined as the reciprocal serum dilution at an OD of approximately 0.5 (normalized to standard, pooled sera from RSV-infected cotton rats with a defined titer of 1:2500 that was included on every plate).

Day 13 and 28 F-specific serum IgG titers for mice immunized with naked RNA and RNA adsorbed to PLG microparticles containing DOTAP, DDA and DC-Cholesterol at N:P ratios 10:1, 4:1 and 1:4 are shown in FIG. 7A. Serum IgG titers normalized to naked 1 µg RNA titers on day 28 are shown in FIG. 7B.

PLG microparticles showed 1 to 4-fold increase in F-specific IgG titers over naked RNA. The results demonstrate that PLG formulations can be used to deliver self-replicating RNA at N:P ratios ranging from 1:4 to 10:1.

Although preferred embodiments of the subject invention have been described in some detail, it is understood that obvious variations can be made without departing from the spirit and the scope of the invention.

In the claims:

1. An immunogenic composition comprising:
   (a) positively charged nanoparticles that comprise a biodegradable polymer and greater than 1% (w/w) of a cationic surfactant, wherein:
      (i) the biodegradable polymer is a poly(α-hydroxy acid), and
      (ii) the nanoparticles have Z average mean particle size value that is between 100 and 500 nanometers, and a zeta potential greater than +50 mV;
   (b) an RNA replicon comprising at least one polynucleotide encoding at least one antigen adsorbed to said positively charged nanoparticles; and
   (c) a non-ionic surfactant.

2. The immunogenic composition of claim 1, wherein the biodegradable polymer is a poly(lactide-co-glycolide).

3. The immunogenic composition of claim 1, wherein the biodegradable polymer is a poly(lactide-co-glycolide) having a lactide:glycolide molar ratio ranging from 40:60 to 60:40.

4. The immunogenic composition of claim 1, wherein the cationic surfactant is selected from (1,2-dioleoyloxypropyl)-N,N,N-trimethylammonium salt (DOTAP), dimethyldioctadecylammonium salt (DDA), and 3-beta-[N—(N',N'-dimethylaminoethane)carbamoyl]cholesterol (DC-Chol).

5. The immunogenic composition of claim 1, wherein the cationic surfactant comprises an ammonium group and a saturated or unsaturated hydrocarbon chain having between 12 to 20 carbon atoms.

6. The composition of claim 1, wherein said non-ionic surfactant is poly(vinyl alcohol).

7. The immunogenic composition of claim 1, wherein said composition further comprises at least one additional component selected from polyols, carbohydrates and combinations thereof.

8. The immunogenic composition of claim 7, wherein said at least one additional component comprises an alditol and a saccharide.

9. The immunogenic composition of claim 1, wherein said RNA replicon is an alphavirus replicon.

10. The immunogenic composition of claim 9, wherein the alphavirus replicon is derived from an alphavirus selected from the group consisting of: Sindbis (SIN), Venezuelan equine encephalitis (VEE), Semliki Forest virus (SFV) and combinations thereof.

11. The immunogenic composition of claim 1, wherein the at least one antigen is selected from a viral antigen, a bacterial antigen and a tumor antigen.

12. The immunogenic composition of claim 1, wherein the at least one antigen is selected from an influenza virus, a respiratory syncytial virus (RSV), a parainfluenza virus (PIV), hepatitis B virus (HBV), a hepatitis C virus (HCV), a human immunodeficiency virus (HIV), a herpes simplex virus (HSV), and a human papilloma virus (HPV), yellow fever, pandemic flu, tuberculosis, dengue, norovirus, measles, rhinovirus, west nile virus, polio, hepatitis A and cytomegalo virus (CMV).

13. The immunogenic composition of claim 1, further comprising an immunological adjuvant.

14. The immunogenic composition of claim 13, wherein the immunological adjuvant is selected from small molecule immune potentiators, toll like receptor ligands, and immunostimulatory oligonulcleotides.

15. The immunogenic composition of claim 13, wherein the immunological adjuvant is adsorbed or entrapped within nanoparticles that may be the same or different from the positively charged nanoparticles comprising the adsorbed RNA replicon.

16. The immunogenic composition of claim 1, wherein the immunogenic composition is an injectable composition.

17. The immunogenic composition of claim 1, wherein the immunogenic composition is lyophilized.

18. An immunogenic composition comprising:
   (a) positively charged nanoparticles that comprise a biodegradable polymer and about 4% (w/w) of a cationic surfactant selected from (1,2-dioleoyloxypropyl)-N,N,N-trimethylammonium salt (DOTAP), dimethyldioctadecylammonium salt (DDA), and 3-beta-[N—(N',N'-dimethylaminoethane)carbamoyl]cholesterol (DC-Chol) wherein:
      (i) the biodegradable polymer is a poly(lactide-co-glycolide), and
      (ii) the nanoparticles have Z average mean particle size value that is between 100 and 250 nanometers, and a zeta potential greater than +50 mV, and
   (b) an RNA replicon comprising at least one polynucleotide encoding at least one antigen adsorbed to said positively charged nanoparticles, wherein ratio of the number of moles of cationic nitrogen in said cationic surfactant to the number of moles of anionic phosphate in said RNA replicon (N:P ratio) is about 4:1, or more.

19. A method of stimulating an immune response in a vertebrate host animal comprising administering to the animal the immunogenic composition of claim 1.

20. A method of forming the immunogenic composition of claim 1, comprising: (a) combining (i) a first liquid that comprises said biodegradable polymer and said cationic surfactant dissolved in an organic solvent with (ii) a second liquid that comprises water, whereupon a first suspension of nanoparticles comprising said biodegradable polymer and said cationic surfactant is formed, (b) adsorbing said RNA replicon to said nanoparticles in said first suspension to form a second suspension, (c) adding at least one additional component comprising a non-ionic surfactant to said second suspension to form a third suspension, and (d) lyophilizing said third suspension.

21. The method of claim 20, wherein said at least one additional component is selected from polyols, carbohydrates and combinations thereof.

22. The composition of claim 18, wherein the nanoparticles have Z average mean particle size value that is between about 200 and about 250 nanometers with a polydispersity index of less than about 0.2.

23. The composition of claim 22, wherein the nanoparticles are formed by solvent extraction, wherein the poly(lactide-co-glycolide) and cationic surfactant are dissolved in acetone solvent.

24. The composition of claim 23, wherein the cationic surfactant is (1,2-dioleoyloxypropyl)-N,N,N-trimethylammonium salt (DOTAP).

25. The composition of claim 24, wherein the composition further comprises about 0.5 to about 20% (w/w) non-ionic surfactant.

26. The composition of claim 1, wherein:

(a) the nanoparticles have Z average mean particle size value that is between about 200 and about 250 nanometers with a polydispersity index of less than about 0.2, (b) the cationic surfactant is (1,2-dioleoyloxypropyl)-N,N,N-trimethylammonium salt (DOTAP), which is present at about 4% (w/w), and (c) the nanoparticles are formed by solvent extraction, wherein the poly(α-hydroxy acid) and cationic surfactant are dissolved in acetone solvent.

* * * * *

SEQUENCE LISTING

```
<160> NUMBER OF SEQ ID NOS: 3

<210> SEQ ID NO 1
<211> LENGTH: 12463
<212> TYPE: DNA
<213> ORGANISM: Artificial sequence
<220> FEATURE:
```

<223> OTHER INFORMATION: Description of Artificial Sequence: Synthetic
polynucleotide

<400> SEQUENCE: 1

```
ataggcggcg catgagagaa gcccagacca attacctacc caaaatggag aaagttcacg      60
ttgacatcga ggaagacagc ccattcctca gagctttgca gcggagcttc ccgcagtttg     120
aggtagaagc caagcaggtc actgataatg accatgctaa tgccagagcg ttttcgcatc     180
tggcttcaaa actgatcgaa acggaggtgg acccatccga cacgatcctt gacattggaa     240
gtgcgcccgc ccgcagaatg tattctaagc acaagtatca ttgtatctgt ccgatgagat     300
gtgcggaaga tccggacaga ttgtataagt atgcaactaa gctgaagaaa aactgtaagg     360
aaataactga taaggaattg gacaagaaaa tgaaggagct cgccgccgtc atgagcgacc     420
ctgacctgga aactgagact atgtgcctcc acgacgacga gtcgtgtcgc tacgaagggc     480
aagtcgctgt ttaccaggat gtatacgcgg ttgacggacc gacaagtctc tatcaccaag     540
ccaataaggg agttagagtc gcctactgga taggctttga caccacccct tttatgttta     600
agaacttggc tggagcatat ccatcatact ctaccaactg ggccgacgaa accgtgttaa     660
cggctcgtaa cataggccta tgcagctctg acgttatgga gcggtcacgt agagggatgt     720
ccattcttag aaagaagtat ttgaaaccat ccaacaatgt tctattctct gttggctcga     780
ccatctacca cgagaagagg gacttactga ggagctggca cctgccgtct gtatttcact     840
tacgtggcaa gcaaaattac acatgtcggt gtgagactat agttagttgc gacgggtacg     900
tcgttaaaag aatagctatc agtccaggcc tgtatgggaa gccttcaggc tatgctgcta     960
cgatgcaccg cgagggattc ttgtgctgca aagtgacaga cacattgaac ggggagaggg    1020
tctcttttcc cgtgtgcacg tatgtgccag ctacattgtg tgaccaaatg actggcatac    1080
tggcaacaga tgtcagtgcg gacgacgcgc aaaaactgct ggttgggctc aaccagcgta    1140
tagtcgtcaa cggtcgcacc cagagaaaca ccaataccat gaaaaattac cttttgcccg    1200
tagtggccca ggcatttgct aggtgggcaa aggaatataa ggaagatcaa gaagatgaaa    1260
ggccactagg actacgagat agacagttag tcatggggtg ttgttgggct tttagaaggc    1320
acaagataac atctatttat aagcgcccgg atacccaaac catcatcaaa gtgaacagcg    1380
atttccactc attcgtgctg cccaggatag gcagtaacac attggagatc gggctgagaa    1440
caagaatcag gaaaatgtta gaggagcaca aggagccgtc acctctcatt accgccgagg    1500
acgtacaaga agctaagtgc gcagccgatg aggctaagga ggtgcgtgaa gccgaggagt    1560
tgcgcgcagc tctaccacct ttggcagctg atgttgagga gcccactctg gaagccgatg    1620
tagacttgat gttacaagag gctggggccg gctcagtgga gacacctcgt ggcttgataa    1680
aggttaccag ctacgatggc gaggacaaga tcggctctta cgctgtgctt tctccgcagg    1740
ctgtactcaa gagtgaaaaa ttatcttgca tccaccctct cgctgaacaa gtcatagtga    1800
taacacactc tggccgaaaa gggcgttatg ccgtggaacc ataccatggt aaagtagtgg    1860
tgccagaggg acatgcaata cccgtccagg actttcaagc tctgagtgaa agtgccacca    1920
ttgtgtacaa cgaacgtgag ttcgtaaaca ggtacctgca ccatattgcc acacatggag    1980
gagcgctgaa cactgatgaa gaatattaca aaactgtcaa gcccagcgag cacgacggcg    2040
aatacctgta cgacatcgac aggaaacagt gcgtcaagaa agaactagtc actgggctag    2100
ggctcacagg cgagctggtg gatcctcct tccatgaatt cgcctacgag agtctgagaa    2160
cacgaccagc cgctccttac caagtaccaa ccataggggt gtatggcgtg ccaggatcag    2220
```

```
gcaagtctgg catcattaaa agcgcagtca ccaaaaaaga tctagtggtg agcgccaaga       2280
aagaaaactg tgcagaaatt ataagggacg tcaagaaaat gaaagggctg acgtcaatg        2340 ccagaactgt ggactcagtg ctcttgaatg gatgcaaaca ccccgtagag accctgtata       2400
ttgacgaagc ttttgcttgt catgcaggta ctctcagagc gctcatagcc attataagac       2460
ctaaaaaggc agtgctctgc ggggatccca aacagtgcgg ttttttttaac atgatgtgcc     2520 tgaaagtgca ttttaaccac gagatttgca cacaagtctt ccacaaaagc atctctcgcc      2580
gttgcactaa atctgtgact tcggtcgtct caaccttgtt ttacgacaaa aaaatgagaa       2640
cgacgaatcc gaaagagact aagattgtga ttgacactac cggcagtacc aaacctaagc     2700
aggacgatct cattctcact tgtttcagag ggtgggtgaa gcagttgcaa atagattaca      2760
aaggcaacga aataatgacg gcagctgcct ctcaagggct gacccgtaaa ggtgtgtatg      2820
ccgttcggta caaggtgaat gaaaatcctc tgtacgcacc cacctcagaa catgtgaacg     2880
tcctactgac ccgcacggag gaccgcatcg tgtggaaaac actagccggc gacccatgga     2940
taaaaacact gactgccaag taccctggga atttcactgc cacgatagag gagtggcaag     3000
cagagcatga tgccatcatg aggcacatct tggagagacc ggaccctacc gacgtcttcc    3060
agaataaggc aaacgtgtgt ggggccaagg ctttagtgcc ggtgctgaag accgctggca    3120
tagacatgac cactgaacaa tggaacactg tggattattt tgaaacggac aaagctcact    3180
cagcagagat agtattgaac caactatgcg tgaggttctt tggactcgat ctggactccg    3240
gtctattttc tgcacccact gttccgttat ccattaggaa taatcactgg gataactccc    3300
cgtcgcctaa catgtacggg ctgaataaag aagtggtccg tcagctctct cgcaggtacc    3360
cacaactgcc tcgggcagtt gccactggaa gagtctatga catgaacact ggtacactgc    3420
gcaattatga tccgcgcata aacctagtac ctgtaaacag aagactgcct catgctttag    3480
tcctccacca taatgaacac ccacagagtg acttttcttc attcgtcagc aaattgaagg    3540
gcagaactgt cctggtggtc ggggaaaagt tgtccgtccc aggcaaaatg gttgactggt    3600
tgtcagaccg gcctgaggct accttcagag ctcggctgga tttaggcatc ccaggtgatg    3660
tgcccaaata tgacataata tttgttaatg tgaggaccc atataaatac catcactatc     3720
agcagtgtga agaccatgcc attaagctta gcatgttgac caagaaagct tgtctgcatc    3780
tgaatcccgg cggaacctgt gtcagcatag gttatggtta cgctgacagg ccagcgaaa     3840 gcatcattgg tgctatagcg cggcagttca agttttcccg ggtatgcaaa ccgaaatcct    3900
cacttgaaga gacggaagtt ctgtttgtat tcattgggta cgatcgcaag gcccgtacgc    3960
acaatcctta caagctttca tcaaccttga ccaacattta tacaggttcc agactccacg    4020
aagccggatg tgcaccctca tatcatgtgg tgcgagggga tattgccacg ccaccgaag    4080 gagtgattat aaatgctgct aacagcaaag gacaacctgg cggagggtg tgcggagcgc    4140 tgtataagaa attcccggaa agcttcgatt tacagccgat cgaagtagga aaagcgcgac    4200
tggtcaaagg tgcagctaaa catatcattc atgccgtagg accaaacttc aacaaagttt    4260
cggaggttga aggtgacaaa cagttggcag aggcttatga gtccatcgct aagattgtca    4320
acgataacaa ttacaagtca gtagcgattc cactgttgtc caccggcatc ttttccggga    4380
acaaagatcg actaacccaa tcattgaacc atttgctgac agctttagac accactgatg    4440
cagatgtagc catatactgc agggacaaga atgggaaat gactctcaag gaagcagtgg     4500
ctaggagaga agcagtggag gagatatgca tatccgacga ctcttcagtg acagaacctg    4560
atgcagagct ggtgagggtg catccgaaga gttctttggc tggaaggaag ggctacagca    4620
```

```
caagcgatgg caaaactttc tcatatttgg aagggaccaa gtttcaccag gcggccaagg    4680
atatagcaga aattaatgcc atgtggcccg ttgcaacgga ggccaatgag caggtatgca    4740
tgtatatcct cggagaaagc atgagcagta ttaggtcgaa atgccccgtc gaagagtcgg    4800
aagcctccac accacctagc acgctgcctt gcttgtgcat ccatgccatg actccagaaa    4860
gagtacagcg cctaaaagcc tcacgtccag aacaaattac tgtgtgctca tcctttccat    4920
tgccgaagta tagaatcact ggtgtgcaga agatccaatg ctcccagcct atattgttct    4980
caccgaaagt gcctgcgtat attcatccaa ggaagtatct cgtggaaaca ccaccggtag    5040
acgagactcc ggagccatcg gcagagaacc aatccacaga ggggacacct gaacaaccac    5100
cacttataac cgaggatgag accaggacta gaacgcctga gccgatcatc atcgaagagg    5160
aagaaggaga tagcataagt ttgctgtcag atggcccgac ccaccaggtg ctgcaagtcg    5220
aggcagacat tcacgggccg ccctctgtat ctagctcatc ctggtccatt cctcatgcat    5280
ccgactttga tgtggacagt ttatccatac ttgacaccct ggaggagct agcgtgacca    5340 gcggggcaac gtcagccgag actaactctt acttcgcaaa gagtatggag tttctggcgc    5400
gaccggtgcc tgcgcctcga acagtattca ggaaccctcc acatcccgct ccgcgcacaa    5460
gaacaccgtc acttgcaccc agcagggcct gctcgagaac cagcctagtt tccaccccgc    5520
caggcgtgaa tagggtgatc actagagagg agctcgaggc gcttacccg tcacgcactc    5580 ctagcaggtc ggtctcgaga accagcctgg tctccaaccc gccaggcgta atagggtga    5640 ttacaagaga ggagtttgag gcgttcgtag cacaacaaca atgacggttt gatgcgggtg    5700
catacatctt ttcctccgac accggtcaag ggcatttaca acaaaaatca gtaaggcaaa    5760
cggtgctatc cgaagtggtg ttggagagga ccgaattgga gatttcgtat gccccgcgcc    5820
tcgaccaaga aaaagaagaa ttactacgca agaaattaca gttaaatccc acacctgcta    5880
acagaagcag ataccagtcc aggaaggtgg agaacatgaa agccataaca gctagacgta    5940
ttctgcaagg cctagggcat tatttgaagg cagaaggaaa agtggagtgc taccgaaccc    6000
tgcatcctgt tcctttgtat tcatctagtg tgaaccgtgc cttttcaagc cccaaggtcg    6060
cagtggaagc ctgtaacgcc atgttgaaag agaactttcc gactgtggct tcttactgta    6120
ttattccaga gtacgatgcc tatttggaca tggttgacgg agcttcatgc tgcttagaca    6180
ctgccagttt tgccctgca aagctgcgca gcttttccaaa gaaacactcc tatttggaac    6240
ccacaatacg atcggcagtg ccttcagcga tccagaacac gctccagaac gtcctggcag    6300
ctgccacaaa aagaaattgc aatgtcacgc aaatgagaga attgcccgta ttggattcgg    6360
cggcctttaa tgtggaatgc ttcaagaaat atgcgtgtaa taatgaatat tgggaaacgt    6420
ttaaagaaaa ccccatcagg cttactgaag aaaacgtggt aaaattacatt accaaattaa    6480 aaggaccaaa agctgctgct cttttttgcga agacacataa tttgaatatg ttgcaggaca    6540
taccaatgga caggtttgta atggacttaa agagagacgt gaaagtgact ccaggaacaa    6600
aacatactga agaacggccc aaggtacagg tgatccaggc tgccgatccg ctagcaacag    6660
cgtatctgtg cggaatccac cgagagctgg ttaggagatt aaatgcggtc ctgcttccga    6720
acattcatac actgtttgat atgtcggctg aagactttga cgctattata gccgagcact    6780
tccagcctgg ggattgtgtt ctggaaactg acatcgcgtc gtttgataaa agtgaggacg    6840
acgccatggc tctgaccgcg ttaatgattc tggaagactt aggtgtggac gcagagctgt    6900
tgacgctgat tgaggcggct ttcggcgaaa tttcatcaat acatttgccc actaaaacta    6960
```

```
aatttaaatt cggagccatg atgaaatctg gaatgttcct cacactgttt gtgaacacag    7020
tcattaacat tgtaatcgca agcagagtgt tgagagaacg gctaaccgga tcaccatgtg    7080
cagcattcat tggagatgac aatatcgtga aaggagtcaa atcggacaaa ttaatggcag    7140
acaggtgcgc cacctggttg aatatggaag tcaagattat agatgctgtg gtgggcgaga    7200
aagcgcctta tttctgtgga gggtttattt tgtgtgactc cgtgaccggc acagcgtgcc    7260
gtgtggcaga ccccctaaaa aggctgttta agcttggcaa acctctggca gcagacgatg    7320
aacatgatga tgacaggaga agggcattgc atgaagagtc aacacgctgg aaccgagtgg    7380
gtattctttc agagctgtgc aaggcagtag aatcaaggta tgaaaccgta ggaacttcca    7440
tcatagttat ggccatgact actctagcta gcagtgttaa atcattcagc tacctgagag    7500
gggcccctat aactctctac ggctaacctg aatggactac gacatagtct agtcgacgcc    7560
accatggaac tgctgatcct gaaggccaac gccatcacca ccatcctgac cgccgtgacc    7620
ttctgcttcg ccagcggcca gaacatcacc gaggaattct accagagcac ctgcagcgcc    7680
gtgagcaagg gctacctgag cgccctgcgg accggctggt acaccagcgt gatcaccatc    7740
gagctgtcca acatcaaaga aaacaagtgc aacggcaccg acgccaaggt gaaactgatc    7800
aagcaggaac tggacaagta caagaacgcc gtgaccgagc tgcagctgct gatgcagagc    7860 accccccgcca ccaacaaccg ggccagaaga gagctgcccc ggttcatgaa ctacaccctg    7920
aacaacgcca agaaaaccaa cgtgaccctg agcaagaagc ggaagcggcg gttcctgggc    7980
ttcctgctgg gcgtgggcag cgccatcgcc agcggggtgg ccgtgtccaa ggtgctgcac    8040
ctggaaggcg aggtgaacaa gatcaagtcc gccctgctgt ccaccaacaa ggccgtggtg    8100
tccctgagca acggcgtgag cgtgctgacc agcaaggtgc tggatctgaa gaactacatc    8160
gacaagcagc tgctgcccat cgtgaacaag cagagctgca gcatcagcaa catcgagacc    8220
gtgatcgagt tccagcagaa gaacaaccgg ctgctggaaa tcacccggga gttcagcgtg    8280
aacgccggcg tgaccacccc cgtgagcacc tacatgctga ccaacagcga gctgctgtcc    8340
ctgatcaatg acatgcccat caccaacgac cagaaaaagc tgatgagcaa caacgtgcag    8400
atcgtgcggc agcagagcta ctccatcatg agcatcatca agaagaggt gctggcctac    8460 gtggtgcagc tgcccctgta cggcgtgatc gacacccct gctggaagct gcacaccagc    8520
cccctgtgca ccaccaacac caaagagggc agcaacatct gcctgacccg gaccgaccgg    8580
ggctggtact gcgacaacgc cggcagcgtg agcttcttcc ccaagccga gacctgcaag    8640 gtgcagagca ccgggtgtt ctgcgacacc atgaacagcc tgaccctgcc ctccgaggtg    8700
aacctgtgca acgtggacat cttcaacccc aagtacgact gcaagatcat gacctccaag    8760
accgacgtga gcagctccgt gatcacctcc ctgggcgcca tcgtgagctg ctacggcaag    8820
accaagtgca ccgccagcaa caagaaccgg ggcatcatca gaccttcag caacggctgc    8880 gactacgtga gcaacaaggg cgtggacacc gtgagcgtgg caacacact gtactacgtg    8940 aataagcagg aaggcaagag cctgtacgtg aagggcgagc ccatcatcaa cttctacgac    9000
cccctggtgt tccccagcga cgagttcgac gccagcatca gccaggtcaa cgagaagatc    9060
aaccagagcc tggccttcat ccggaagagc gacgagctgc tgcacaatgt gaatgccggc    9120
aagagcacca ccaatatcat gatcaccaca atcatcatcg tgatcattgt gatcctgctg    9180
tctctgattg ccgtgggcct gctgctgtac tgcaaggccc gcagcacccc tgtgaccctg    9240
tccaaggacc agctgtccgg catcaacaat atcgccttct ccaactgaag tctagacggc    9300
gcgcccaccc agcggccgca tacagcagca attggcaagc tgcttacata gaactcgcgg    9360
```

```
cgattggcat gccgccttaa aattttttatt ttattttttct tttcttttcc gaatcggatt    9420
ttgttttttaa tatttcaaaa aaaaaaaaaa aaaaaaaaaa aaaaaaaaaa agggtcggca    9480
tggcatctcc acctcctcgc ggtccgacct gggcatccga aggaggacgc acgtccactc    9540
ggatggctaa gggagagcca cgtttaaacc agctccaatt cgccctatag tgagtcgtat    9600
tacgcgcgct cactggccgt cgttttacaa cgtcgtgact gggaaaaccc tggcgttacc    9660
caacttaatc gccttgcagc acatcccct ttcgccagct ggcgtaatag cgaagaggcc    9720
cgcaccgatc gcccttccca acagttgcgc agcctgaatg gcgaatggga cgcgccctgt    9780
agcggcgcat taagcgcggc gggtgtggtg gttacgcgca gcgtgaccgc tacacttgcc    9840
agcgccctag cgcccgctcc tttcgctttc ttcccttcct ttctcgccac gttcgccggc    9900
tttccccgtc aagctctaaa tcggggctc cctttagggt tccgatttag tgctttacgg    9960
cacctcgacc ccaaaaaact tgattagggt gatggttcac gtagtgggcc atcgccctga   10020
tagacggttt ttcgcccttt gacgttggag tccacgttct ttaatagtgg actcttgttc   10080
caaactggaa caacactcaa ccctatctcg gtctattctt ttgatttata agggattttg   10140
ccgatttcgg cctattggtt aaaaaatgag ctgatttaac aaaaatttaa cgcgaatttt   10200
aacaaaatat taacgcttac aatttaggtg cacttttcg gggaaatgtg cgcggaaccc   10260
ctatttgttt attttctaa atacattcaa atatgtatcc gctcatgaga caataaccct   10320
gataaatgct tcaataatat tgaaaaagga agagtatgag tattcaacat ttccgtgtcg   10380
cccttattcc cttttttgcg gcattttgcc ttcctgtttt tgctcaccca gaaacgctgg   10440
tgaaagtaaa agatgctgaa gatcagttgg gtgcacgagt gggttacatc gaactggatc   10500
tcaacagcgg taagatcctt gagagttttc gccccgaaga acgttttcca atgatgagca   10560
cttttaaagt tctgctatgt ggcgcggtat tatcccgtat tgacgccggg caagagcaac   10620
tcggtcgccg catacactat tctcagaatg acttggttga gtactcacca gtcacagaaa   10680
agcatcttac ggatggcatg acagtaagag aattatgcag tgctgccata accatgagtg   10740
ataacactgc ggccaactta cttctgacaa cgatcggagg accgaaggag ctaaccgctt   10800
ttttgcacaa catgggggat catgtaactc gccttgatcg ttgggaaccg gagctgaatg   10860
aagccatacc aaacgacgag cgtgacacca cgatgcctgt agcaatggca acaacgttgc   10920
gcaaactatt aactggcgaa ctacttactc tagcttcccg gcaacaatta atagactgga   10980
tggaggcgga taaagttgca ggaccacttc tgcgctcggc ccttccggct ggctggttta   11040
ttgctgataa atctggagcc ggtgagcgtg ggtctcgcgg tatcattgca gcactgggc   11100
cagatggtaa gccctcccgt atcgtagtta tctacacgac ggggagtcag gcaactatgg   11160
atgaacgaaa tagacagatc gctgagatag gtgcctcact gattaagcat tggtaactgt   11220
cagaccaagt ttactcatat atactttaga ttgatttaaa acttcatttt taatttaaaa   11280
ggatctaggt gaagatcctt tttgataatc tcatgaccaa aatcccttaa cgtgagtttt   11340
cgttccactg agcgtcagac cccgtagaaa agatcaaagg atcttcttga gatccttttt   11400
ttctgcgcgt aatctgctgc ttgcaaacaa aaaaaccacc gctaccagcg gtggtttgtt   11460
tgccggatca agagctacca actctttttc cgaaggtaac tggcttcagc agagcgcaga   11520
taccaaatac tgttcttcta gtgtagccgt agttaggcca ccacttcaag aactctgtag   11580
caccgcctac atacctcgct ctgctaatcc tgttaccagt ggctgctgcc agtggcgata   11640
agtcgtgtct taccgggttg gactcaagac gatagttacc ggataaggcg cagcggtcgg   11700
```

| | |
|---|---|
| gctgaacggg gggttcgtgc acacagccca gcttggagcg aacgacctac accgaactga | 11760 |
| gatacctaca gcgtgagcta tgagaaagcg ccacgcttcc cgaagggaga aaggcggaca | 11820 |
| ggtatccggt aagcggcagg gtcggaacag gagagcgcac gagggagctt ccaggggggaa | 11880 |
| acgcctggta tctttatagt cctgtcgggt ttcgccacct ctgacttgag cgtcgatttt | 11940 |
| tgtgatgctc gtcagggggg cggagcctat ggaaaaacgc cagcaacgcg gcctttttac | 12000 |
| ggttcctggc cttttgctgg ccttttgctc acatgttctt tcctgcgtta tcccctgatt | 12060 |
| ctgtggataa ccgtattacc gcctttgagt gagctgatac cgctcgccgc agccgaacga | 12120 |
| ccgagcgcag cgagtcagtg agcgaggaag cggaagagcg cccaatacgc aaaccgcctc | 12180 |
| tccccgcgcg ttggccgatt cattaatgca gctggcacga caggtttccc gactggaaag | 12240 |
| cgggcagtga gcgcaacgca attaatgtga gttagctcac tcattaggca ccccaggctt | 12300 |
| tacactttat gctcccggct cgtatgttgt gtggaattgt gagcggataa caatttcaca | 12360 |
| caggaaacag ctatgaccat gattacgcca agcgcgcaat taaccctcac taaagggaac | 12420 |
| aaaagctggg taccgggccc acgcgtaata cgactcacta tag | 12463 |

<210> SEQ ID NO 2
<211> LENGTH: 12301
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2

| | |
|---|---|
| ataggcggcg catgagagaa gcccagacca attacctacc caaaatggag aaagttcacg | 60 |
| ttgacatcga ggaagacagc ccattcctca gagctttgca gcggagcttc ccgcagtttg | 120 |
| aggtagaagc caagcaggtc actgataatg accatgctaa tgccagagcg ttttcgcatc | 180 |
| tggcttcaaa actgatcgaa acggaggtgg acccatccga cacgatcctt gacattggaa | 240 |
| gtgcgcccgc ccgcagaatg tattctaagc acaagtatca ttgtatctgt ccgatgagat | 300 |
| gtgcggaaga tccggacaga ttgtataagt atgcaactaa gctgaagaaa aactgtaagg | 360 |
| aaataactga taaggaattg gacaagaaaa tgaaggagct cgccgccgtc atgagcgacc | 420 |
| ctgacctgga aactgagact atgtgcctcc acgacgacga gtcgtgtcgc tacgaagggc | 480 |
| aagtcgctgt ttaccaggat gtatacgcgg ttgacgggcc gacaagtctc tatcaccaag | 540 |
| ccaataaggg agttagagtc gcctactgga taggctttga caccaccccct tttatgttta | 600 |
| agaacttggc tggagcatat ccatcatact ctaccaactg ggccgacgaa accgtgttaa | 660 |
| cggctcgtaa cataggccta tgcagctctg acgttatgga gcggtcacgt agagggatgt | 720 |
| ccattcttag aaagaagtat ttgaaaccat ccaacaatgt tctattctct gttggctcga | 780 |
| ccatctacca cgagaagagg gacttactga ggagctggca cctgccgtct gtatttcact | 840 |
| tacgtggcaa gcaaaattac acatgtcggt gtgagactat agttagttgc gacgggtacg | 900 |
| tcgttaaaag aatagctatc agtccaggcc tgtatgggaa gccttcaggc tatgctgcta | 960 |
| cgatgcaccg cgagggattc ttgtgctgca aagtgacaga cattgaac ggggagaggg | 1020 |
| tctctttttcc cgtgtgcacg tatgtgccag ctacattgtg tgaccaaatg actggcatac | 1080 |
| tggcaacaga tgtcagtgcg gacgacgcgc aaaaactgct ggttgggctc aaccagcgta | 1140 |
| tagtcgtcaa cggtcgcacc cagagaaaca ccaataccat gaaaaattac cttttgcccg | 1200 |
| tagtggccca ggcatttgct aggtgggcaa aggaatataa ggaagatcaa gaagatgaaa | 1260 |

```
ggccactagg actacgagat agacagttag tcatggggtg ttgttgggct tttagaaggc    1320
acaagataac atctatttat aagcgcccgg atacccaaac catcatcaaa gtgaacagcg    1380
atttccactc attcgtgctg cccaggatag gcagtaacac attggagatc gggctgagaa    1440
caagaatcag gaaaatgtta gaggagcaca aggagccgtc acctctcatt accgccgagg    1500
acgtacaaga agctaagtgc gcagccgatg aggctaagga ggtgcgtgaa gccgaggagt    1560
tgcgcgcagc tctaccacct ttggcagctg atgttgagga gcccactctg gaagccgatg    1620
tagacttgat gttacaagag gctggggccg gctcagtgga gacacctcgt ggcttgataa    1680
aggttaccag ctacgatggc gaggacaaga tcggctctta cgctgtgctt tctccgcagg    1740
ctgtactcaa gagtgaaaaa ttatcttgca tccaccctct cgctgaacaa gtcatagtga    1800
taacacactc tggccgaaaa gggcgttatg ccgtggaacc ataccatggt aaagtagtgg    1860
tgccagaggg acatgcaata cccgtccagg actttcaagc tctgagtgaa agtgccacca    1920
ttgtgtacaa cgaacgtgag ttcgtaaaca ggtacctgca ccatattgcc acacatggag    1980
gagcgctgaa cactgatgaa gaatattaca aaactgtcaa gcccagcgag cacgacggcg    2040
aatacctgta cgacatcgac aggaaacagt gcgtcaagaa agaactagtc actgggctag    2100
ggctcacagg cgagctggtg gatcctccct tccatgaatt cgcctacgag agtctgagaa    2160
cacgaccagc cgctccttac caagtaccaa ccatagggt gtatggcgtg ccaggatcag    2220
gcaagtctgg catcattaaa agcgcagtca ccaaaaaaga tctagtggtg agcgccaaga    2280
aagaaaactg tgcagaaatt ataagggacg tcaagaaaat gaagggctg acgtcaatg     2340
ccagaactgt ggactcagtg ctcttgaatg gatgcaaaca ccccgtagag accctgtata    2400
ttgacgaagc ttttgcttgt catgcaggta ctctcagagc gctcatagcc attataagac    2460
ctaaaaaggc agtgctctgc ggggatccca acagtgcgg tttttttaac atgatgtgcc    2520
tgaaagtgca ttttaaccac gagatttgca cacaagtctt ccacaaaagc atctctcgcc    2580
gttgcactaa atctgtgact tcggtcgtct caaccttgtt ttacgacaaa aaaatgagaa    2640
cgacgaatcc gaaagagact aagattgtga ttgacactac cggcagtacc aaacctaagc    2700
aggacgatct cattctcact tgtttcagag ggtgggtgaa gcagttgcaa atagattaca    2760
aaggcaacga ataatgacg gcagctgcct ctcaagggct gacccgtaaa ggtgtgtatg     2820
ccgttcggta caaggtgaat gaaaatcctc tgtacgcacc cacctcagaa catgtgaacg    2880
tcctactgac ccgcacggag gaccgcatcg tgtggaaaac actagccggc gacccatgga    2940
taaaaacact gactgccaag taccctggga atttcactgc cacgatagag gagtggcaag    3000
cagagcatga tgccatcatg aggcacatct tggagagacc ggaccctacc gacgtcttcc    3060
agaataaggc aaacgtgtgt tgggccaagg cttagtgcc ggtgctgaag accgctggca     3120
tagacatgac cactgaacaa tggaacactg tggattattt tgaaacggac aaagctcact    3180
cagcagagat agtattgaac caactatgcg tgaggttctt tggactcgat ctggactccg    3240
gtctatttc tgcacccact gttccgttat ccattaggaa taatcactgg gataactccc     3300
cgtcgcctaa catgtacggg ctgaataaag aagtggtccg tcagctctct cgcaggtacc    3360
cacaactgcc tcgggcagtt gccactggaa gagtctatga catgaacact ggtacactgc    3420
gcaattatga tccgcgcata aacctagtac ctgtaaacag aagactgcct catgctttag    3480
tcctccacca taatgaacac ccacagagtg acttttcttc attcgtcagc aaattgaagg    3540
gcagaactgt cctggtggtc gggggaaaagt tgtccgtccc aggcaaaatg gttgactggt    3600
tgtcagaccg gcctgaggct accttcagag ctcggctgga tttaggcatc ccaggtgatg    3660
```

```
tgcccaaata tgacataata tttgttaatg tgaggacccc atataaatac catcactatc    3720
agcagtgtga agaccatgcc attaagctta gcatgttgac caagaaagct tgtctgcatc    3780
tgaatcccgg cggaacctgt gtcagcatag gttatggtta cgctgacagg gccagcgaaa    3840
gcatcattgg tgctatagcg cggcagttca agttttcccg ggtatgcaaa ccgaaatcct    3900
cacttgaaga gacggaagtt ctgtttgtat tcattgggta cgatcgcaag gcccgtacgc    3960
acaatcctta caagctttca tcaaccttga ccaacattta tacaggttcc agactccacg    4020
aagccggatg tgcaccctca tatcatgtgg tgcgagggga tattgccacg gccaccgaag    4080
gagtgattat aaatgctgct aacagcaaag gacaacctgg cggaggggtg tgcggagcgc    4140
tgtataagaa attcccggaa agcttcgatt tacagccgat cgaagtagga aaagcgcgac    4200
tggtcaaagg tgcagctaaa catatcattc atgccgtagg accaaacttc aacaaagttt    4260
cggaggttga aggtgacaaa cagttggcag aggcttatga gtccatcgct aagattgtca    4320
acgataacaa ttacaagtca gtagcgattc cactgttgtc caccggcatc ttttccggga    4380
acaaagatcg actaacccaa tcattgaacc atttgctgac agctttagac accactgatg    4440
cagatgtagc catatactgc agggacaaga aatgggaaat gactctcaag gaagcagtgg    4500
ctaggagaga agcagtggag gagatatgca tatccgacga ctcttcagtg acagaacctg    4560
atgcagagct ggtgagggtg catccgaaga gttctttggc tggaaggaag ggctacagca    4620
caagcgatgg caaaactttc tcatatttgg aagggaccaa gtttcaccag gcggccaagg    4680
atatagcaga aattaatgcc atgtggcccg ttgcaacgga ggccaatgag caggtatgca    4740
tgtatatcct cggagaaagc atgagcagta ttaggtcgaa atgcccgtc gaagagtcgg    4800 aagcctccac accacctagc acgctgcctt gcttgtgcat ccatgccatg actccagaaa    4860
gagtacagcg cctaaaagcc tcacgtccag aacaaattac tgtgtgctca tccttccat    4920 tgccgaagta tagaatcact ggtgtgcaga agatccaatg ctcccagcct atattgttct    4980
caccgaaagt gcctgcgtat attcatccaa ggaagtatct cgtggaaaca ccaccggtag    5040
acgagactcc ggagccatcg gcagagaacc aatccacaga ggggacacct gaacaaccac    5100
cacttataac cgaggatgag accaggacta gaacgcctga gccgatcatc atcgaagagg    5160
aagaagagga tagcataagt ttgctgtcag atggcccgac ccaccaggtg ctgcaagtcg    5220
aggcagacat tcacgggccg ccctctgtat ctagctcatc ctggtccatt cctcatgcat    5280
ccgactttga tgtggacagt ttatccatac ttgacccct ggagggagct agcgtgacca    5340
gcggggcaac gtcagccgag actaactctt acttcgcaaa gagtatggag tttctggcgc    5400
gaccggtgcc tgcgcctcga acagtattca ggaaccctcc acatcccgct ccgcgcacaa    5460
gaacaccgtc acttgcaccc agcagggcct gctcgagaac cagcctagtt tccaccccgc    5520
caggcgtgaa tagggtgatc actagagagg agctcgaggc gcttacccg tcacgcactc    5580 ctagcaggtc ggtctcgaga accagcctgg tctccaaccc gccaggcgta aatagggtga    5640
ttacaagaga ggagtttgag gcgttcgtag cacaacaaca atgacggttt gatgcgggtg    5700
catacatctt ttcctccgac accggtcaag ggcatttaca acaaaaatca gtaaggcaaa    5760
cggtgctatc cgaagtggtg ttggagagga ccgaattgga gatttcgtat gccccgcgcc    5820
tcgaccaaga aaaagaagaa ttactacgca agaaattaca gttaaatccc acacctgcta    5880
acagaagcag ataccagtcc aggaaggtgg agaacatgaa agccataaca gctagacgta    5940
ttctgcaagg cctagggcat tatttgaagg cagaaggaaa agtggagtgc taccgaaccc    6000
```

```
tgcatcctgt tcctttgtat tcatctagtg tgaaccgtgc cttttcaagc cccaaggtcg   6060
cagtggaagc ctgtaacgcc atgttgaaag agaactttcc gactgtggct tcttactgta   6120
ttattccaga gtacgatgcc tatttggaca tggttgacgg agcttcatgc tgcttagaca   6180
ctgccagttt ttgccctgca aagctgcgca gctttccaaa gaaacactcc tatttggaac   6240
ccacaatacg atcggcagtg ccttcagcga tccagaacac gctccagaac gtcctggcag   6300
ctgccacaaa aagaaattgc aatgtcacgc aaatgagaga attgcccgta ttggattcgg   6360
cggcctttaa tgtggaatgc ttcaagaaat atgcgtgtaa taatgaatat tgggaaacgt   6420
ttaaagaaaa ccccatcagg cttactgaag aaaacgtggt aaattacatt accaaattaa   6480
aaggaccaaa agctgctgct cttttttgcga agacacataa tttgaatatg ttgcaggaca   6540
taccaatgga caggtttgta atggacttaa agagagacgt gaaagtgact ccaggaacaa   6600
aacatactga agaacggccc aaggtacagg tgatccaggc tgccgatccg ctagcaacag   6660
cgtatctgtg cggaatccac cgagagctgg ttaggagatt aaatgcggtc ctgcttccga   6720
acattcatac actgtttgat atgtcggctg aagactttga cgctattata gccgagcact   6780
tccagcctgg ggattgtgtt ctggaaactg acatcgcgtc gtttgataaa agtgaggacg   6840
acgccatggc tctgaccgcg ttaatgattc tggaagactt aggtgtggac gcagagctgt   6900
tgacgctgat tgaggcggct ttcggcgaaa tttcatcaat acatttgccc actaaaacta   6960
aatttaaatt cggagccatg atgaaatctg gaatgttcct cacactgttt gtgaacacag   7020
tcattaacat tgtaatcgca agcagagtgt tgagagaacg gctaaccgga tcaccatgtg   7080
cagcattcat tggagatgac aatatcgtga aaggagtcaa atcggacaaa ttaatgcag   7140 acaggtgcgc cacctggttg aatatggaag tcaagattat agatgctgtg gtgggcgaga   7200
aagcgcctta tttctgtgga gggttttattt tgtgtgactc cgtgaccggc acagcgtgcc   7260
gtgtggcaga ccccctaaaa aggctgttta gcttggcaa acctctggca gcagacgatg   7320
aacatgatga tgacaggaga agggcattgc atgaagagtc aacacgctgg aaccgagtgg   7380
gtattctttc agagctgtgc aaggcagtag aatcaaggta tgaaaccgta ggaacttcca   7440
tcatagttat ggccatgact actctagcta gcagtgttaa atcattcagc tacctgagag   7500
gggcccctat aactctctac ggctaacctg aatggactac gacatagtct agtcgacgcc   7560
accatgctgc tgctgctgct gctgctgggc ctgaggctac agctctccct gggcatcatc   7620
ccagttgagg aggagaaccc ggacttctgg aaccgcgagg cagccgaggc cctgggtgcc   7680
gccaagaagc tgcagcctgc acagacagcg gccaagaacc tcatcatctt cctgggcgat   7740
gggatggggg tgtctacggt gacagctgcc aggatcctaa aagggcagaa gaaggacaaa   7800
ctggggcctg agatacccct ggccatggac cgcttcccat atgtggctct gtccaagaca   7860
tacaatgtag acaaacatgt gccagacagt ggagccacag ccacggccta cctgtgcggg   7920
gtcaagggca acttccagac cattggcttg agtgcagccg cccgctttaa ccagtgcaac   7980
acgacacgcg gcaacgaggt catctccgtg atgaatcggg ccaagaaagc agggaagtca   8040
gtgggagtgg taaccaccac acgagtgcag cacgcctcgc cagccggcac ctacgcccac   8100
acggtgaacc gcaactggta ctcggacgcc gacgtgcctg cctcggcccg ccaggagggg   8160
tgccaggaca tcgctacgca gctcatctcc aacatggaca ttgacgtgat cctaggtgga   8220
ggccgaaagt acatgtttcg catgggaacc ccagaccctg agtacccaga tgactacagc   8280
caaggtggga ccaggctgga cgggaagaat ctggtgcagg aatggctggc gaagcgccag   8340
ggtgcccggt atgtgtggaa ccgcactgag ctcatgcagg cttccctgga cccgtctgtg   8400
```

```
acccatctca tgggtctctt tgagcctgga gacatgaaat acgagatcca ccgagactcc   8460
acactggacc cctccctgat ggagatgaca gaggctgccc tgcgcctgct gagcaggaac   8520
ccccgcggct tcttcctctt cgtggagggt ggtcgcatcg accatggtca tcatgaaagc   8580
agggcttacc gggcactgac tgagacgatc atgttcgacg acgccattga gagggcgggc   8640
cagctcacca gcgaggagga cacgctgagc ctcgtcactg ccgaccactc ccacgtcttc   8700
tccttcggag gctaccccct gcgagggagc tccatcttcg ggctggcccc tggcaaggcc   8760
cgggacagga aggcctacac ggtcctccta tacgaaacg gtccaggcta tgtgctcaag    8820
gacggcgccc ggccggatgt taccgagagc gagagcggga gccccgagta tcggcagcag   8880
tcagcagtgc ccctggacga agagacccac gcaggcgagg acgtggcggt gttcgcgcgc   8940
ggcccgcagg cgcacctggt tcacggcgtg caggagcaga ccttcatagc gcacgtcatg   9000
gccttcgccg cctgcctgga gccctacacc gcctgcgacc tggcgccccc cgccggcacc   9060
accgacgccg cgcacccggg ttactctaga gtcggggcgg ccggccgctt cgagcagaca   9120
tgaactagac ggcgcgccca cccagcggcc gcatacagca gcaattggca agctgcttac   9180
atagaactcg cggcgattgg catgccgcct taaaattttt attttatttt tcttttcttt   9240
tccgaatcgg attttgtttt taatatttca aaaaaaaaa aaaaaaaaa aaaaaaaaa      9300 aaaaaaaaag ggtcggcatg gcatctccac ctcctcgcgg tccgacctgg gcatccgaag   9360
gaggacgcac gtccactcgg atggctaagg gagagccacg tttaaaccag ctccaattcg   9420
ccctatagtg agtcgtatta cgcgcgctca ctggccgtcg ttttacaacg tcgtgactgg   9480
gaaaaccctg gcgttaccca acttaatcgc cttgcagcac atcccccttt cgccagctgg   9540
cgtaatagcg aagaggcccg caccgatcgc ccttcccaac agttgcgcag cctgaatggc   9600
gaatgggacg cgccctgtag cggcgcatta agcgcggcgg gtgtggtggt tacgcgcagc   9660
gtgaccgcta cacttgccag cgccctagcg cccgctcctt tcgctttctt cccttccttt   9720
ctcgccacgt tcgccggctt tccccgtcaa gctctaaatc gggggctccc tttagggttc   9780
cgatttagtg ctttacggca cctcgacccc aaaaaacttg attagggtga tggttcacgt   9840
agtgggccat cgccctgata cacggttttt cgccctttga cgttggagtc cacgttcttt   9900
aatagtggac tcttgttcca aactggaaca cactcaacc ctatctcggt ctattctttt    9960
gatttataag ggattttgcc gatttcggcc tattggttaa aaaatgagct gatttaacaa  10020
aaatttaacg cgaattttaa caaaatatta cgcttacaa tttaggtggc acttttcggg   10080
gaaatgtgcg cggaaccct atttgtttat ttttctaaat acattcaaat atgtatccgc    10140
tcatgagaca ataaccctga taaatgcttc aataatattg aaaaggaag agtatgagta    10200 ttcaacattt ccgtgtcgcc cttattccct ttttgcggc attttgcctt cctgtttttg    10260
ctcacccaga aacgctggtg aaagtaaaag atgctgaaga tcagttgggt gcacgagtgg   10320
gttacatcga actggatctc aacagcggta agatccttga gttttcgc cccgaagaac     10380 gttttccaat gatgagcact tttaaagttc tgctatgtgg cgcggtatta tcccgtattg   10440
acgccgggca agagcaactc ggtcgccgca tacactattc tcagaatgac ttggttgagt   10500
actcaccagt cacagaaaag catcttacgg atggcatgac agtaagagaa ttatgcagtg   10560
ctgccataac catgagtgat aacactgcgg ccaacttact tctgacaacg atcggaggac   10620
cgaaggagct aaccgctttt ttgcacaaca tgggggatca tgtaactcgc cttgatcgtt   10680
gggaaccgga gctgaatgaa gccataccaa acgacgagcg tgacaccacg atgcctgtag   10740
```

```
caatggcaac aacgttgcgc aaactattaa ctggcgaact acttactcta gcttcccggc   10800
aacaattaat agactggatg gaggcggata aagttgcagg accacttctg cgctcggccc   10860
ttccggctgg ctggtttatt gctgataaat ctggagccgg tgagcgtggg tctcgcggta   10920
tcattgcagc actggggcca gatggtaagc cctcccgtat cgtagttatc tacacgacgg   10980
ggagtcaggc aactatggat gaacgaaata dacagatcgc tgagataggt gcctcactga   11040
ttaagcattg gtaactgtca gaccaagttt actcatatat actttagatt gatttaaaac   11100
ttcattttta atttaaaagg atctaggtga agatcctttt tgataatctc atgaccaaaa   11160
tcccttaacg tgagttttcg ttccactgag cgtcagaccc cgtagaaaag atcaaaggat   11220
cttcttgaga tccttttttt ctgcgcgtaa tctgctgctt gcaaacaaaa aaaccaccgc   11280
taccagcggt ggtttgtttg ccggatcaag agctaccaac tctttttccg aaggtaactg   11340
gcttcagcag agcgcagata ccaaatactg tccttctagt gtagccgtag ttaggccacc   11400
acttcaagaa ctctgtagca ccgcctacat acctcgctct gctaatcctg ttaccagtgg   11460
ctgctgccag tggcgataag tcgtgtctta ccgggttgga ctcaagacga tagttaccgg   11520
ataaggcgca gcggtcgggc tgaacggggg gttcgtgcac acagcccagc ttggagcgaa   11580
cgacctacac cgaactgaga tacctacagc gtgagctatg agaaagcgcc acgcttcccg   11640
aagggagaaa ggcggacagg tatccggtaa gcggcagggt cggaacagga gagcgcacga   11700
gggagcttcc agggggaaac gcctggtatc tttatagtcc tgtcgggttt cgccacctct   11760
gacttgagcg tcgatttttg tgatgctcgt caggggggcg gagcctatgg aaaaacgcca   11820
gcaacgcggc ctttttacgg ttcctggcct tttgctggcc ttttgctcac atgttctttc   11880
ctgcgttatc ccctgattct gtggataacc gtattaccgc ctttgagtga gctgataccg   11940
ctcgccgcag ccgaacgacc gagcgcagcg agtcagtgag cgaggaagcg gaagagcgcc   12000
caatacgcaa accgcctctc cccgcgcgtt ggccgattca ttaatgcagc tggcacgaca   12060
ggtttcccga ctggaaagcg ggcagtgagc gcaacgcaat taatgtgagt tagctcactc   12120
attaggcacc ccaggcttta cactttatgc ttccggctcg tatgttgtgt ggaattgtga   12180
gcggataaca atttcacaca ggaaacagct atgaccatga ttacgccaag cgcgcaatta   12240
accctcacta aagggaacaa aagctgggta ccgggcccac gcgtaatacg actcactata   12300
g                                                                    12301
```

<210> SEQ ID NO 3
<211> LENGTH: 12761
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3

```
atgggcggcg catgagagaa gcccagacca attacctacc caaaatggag aaagttcacg     60
ttgacatcga ggaagacagc ccattcctca gagctttgca gcggagcttc ccgcagtttg    120
aggtagaagc caagcaggtc actgataatg accatgctaa tgccagagcg ttttcgcatc    180
tggcttcaaa actgatcgaa acggaggtgg acccatccga cacgatcctt gacattggaa    240
gtgcgcccgc ccgcagaatg tattctaagc acaagtatca ttgtatctgt ccgatgagat    300
gtgcggaaga tccggacaga ttgtataagt atgcaactaa gctgaagaaa aactgtaagg    360
aaataactga taaggaattg gacaagaaaa tgaaggagct cgccgccgtc atgagcgacc    420
```

```
ctgacctgga aactgagact atgtgcctcc acgacgacga gtcgtgtcgc tacgaagggc      480
aagtcgctgt ttaccaggat gtatacgcgg ttgacggacc gacaagtctc tatcaccaag      540
ccaataaggg agttagagtc gcctactgga taggctttga caccacccct tttatgttta      600
agaacttggc tggagcatat ccatcatact ctaccaactg ggccgacgaa accgtgttaa      660
cggctcgtaa cataggccta tgcagctctg acgttatgga gcggtcacgt agagggatgt      720
ccattcttag aaagaagtat ttgaaaccat ccaacaatgt tctattctct gttggctcga      780
ccatctacca cgagaagagg gacttactga ggagctggca cctgccgtct gtatttcact      840
tacgtggcaa gcaaaattac acatgtcggt gtgagactat agttagttgc gacgggtacg      900
tcgttaaaag aatagctatc agtccaggcc tgtatgggaa gccttcaggc tatgctgcta      960
cgatgcaccg cgagggattc ttgtgctgca aagtgacaga cacattgaac ggggagaggg     1020 tctctttttcc cgtgtgcacg tatgtgccag ctacattgtg tgaccaaatg actggcatac     1080
tggcaacaga tgtcagtgcg gacgacgcgc aaaaactgct ggttgggctc aaccagcgta     1140
tagtcgtcaa cggtcgcacc cagagaaaca ccaataccat gaaaaattac cttttgcccg     1200
tagtggccca ggcatttgct aggtgggcaa aggaatataa ggaagatcaa gaagatgaaa     1260
ggccactagg actacgagat agacagttag tcatggggtg ttgttgggct tttagaaggc     1320
acaagataac atctatttat aagcgcccgg atacccaaac catcatcaaa gtgaacagcg     1380
atttccactc attcgtgctg cccaggatag gcagtaacac attggagatc gggctgagaa     1440
caagaatcag gaaaatgtta gaggagcaca aggagccgtc acctctcatt accgccgagg     1500
acgtacaaga agctaagtgc gcagccgatg aggctaagga ggtgcgtgaa gccgaggagt     1560
tgcgcgcagc tctaccacct ttggcagctg atgttgagga gcccactctg gaagccgatg     1620
tcgacttgat gttacaagag gctggggccg gctcagtgga gacacctcgt ggcttgataa     1680
aggttaccag ctacgctggc gaggacaaga tcggctctta cgctgtgctt tctccgcagg     1740
ctgtactcaa gagtgaaaaa ttatcttgca tccaccctct cgctgaacaa gtcatagtga     1800
taacacactc tggccgaaaa gggcgttatg ccgtggaacc ataccatggt aaagtagtgg     1860
tgccagaggg acatgcaata cccgtccagg actttcaagc tctgagtgaa agtgccacca     1920
ttgtgtacaa cgaacgtgag ttcgtaaaca ggtacctgca ccatattgcc acacatggag     1980
gagcgctgaa cactgatgaa gaatattaca aaactgtcaa gcccagcgag cacgacggcg     2040
aatacctgta cgacatcgac aggaaacagt gcgtcaagaa agaactagtc actgggctag     2100
ggctcacagg cgagctggtg gatcctcccct tccatgaatt cgcctacgag agtctgagaa     2160
cacgaccagc cgctccttac caagtaccaa ccatagggt gtatggcgtg ccaggatcag     2220
gcaagtctgg catcattaaa agcgcagtca ccaaaaaaga tctagtggtg agcgccaaga     2280
aagaaaactg tgcagaaatt ataagggacg tcaagaaaat gaagggctg acgtcaatg     2340 ccagaactgt ggactcagtg ctcttgaatg gatgcaaaca ccccgtagag accctgtata     2400
ttgacgaagc ttttgcttgt catgcaggta ctctcagagc gctcatagcc attataagac     2460
ctaaaaaggc agtgctctgc ggggatcccca aacagtgcgg ttttttaac atgatgtgcc     2520 tgaaagtgca ttttaaccac gagatttgca cacaagtctt ccacaaaagc atctctcgcc     2580
gttgcactaa atctgtgact tcggtcgtct caaccttgtt ttacgacaaa aaaatgagaa     2640
cgacgaatcc gaaagagact aagattgtga ttgacactac cggcagtacc aaacctaagc     2700
aggacgatct cattctcact tgtttcagag ggtgggtgaa gcagttgcaa atagattaca     2760
aaggcaacga aataatgacg gcagctgcct ctcaagggct gacccgtaaa ggtgtgtatg     2820
```

```
ccgttcggta caaggtgaat gaaaatcctc tgtacgcacc cacctcagaa catgtgaacg    2880
tcctactgac ccgcacggag gaccgcatcg tgtggaaaac actagccggc gacccatgga    2940
taaaaacact gactgccaag taccctggga atttcactgc cacgatagag gagtggcaag    3000
cagagcatga tgccatcatg aggcacatct tggagagacc ggaccctacc gacgtcttcc    3060
agaataaggc aaacgtgtgt tgggccaagg ctttagtgcc ggtgctgaag accgctggca    3120
tagacatgac cactgaacaa tggaacactg tggattattt tgaaacggac aaagctcact    3180
cagcagagat agtattgaac caactatgcg tgaggttctt tggactcgat ctggactccg    3240
gtctattttc tgcacccact gttccgttat ccattaggaa taatcactgg gataactccc    3300
cgtcgcctaa catgtacggg ctgaataaag aagtggtccg tcagctctct cgcaggtacc    3360
cacaactgcc tcgggcagtt gccactggaa gagtctatga catgaacact ggtacactgc    3420
gcaattatga tccgcgcata aacctagtac ctgtaaacag aagactgcct catgctttag    3480
tcctccacca taatgaacac ccacagagtg acttttcttc attcgtcagc aaattgaagg    3540
gcagaactgt cctggtggtc ggggaaaagt tgtccgtccc aggcaaaatg gttgactggt    3600
tgtcagaccg gcctgaggct accttcagag ctcggctgga tttaggcatc ccaggtgatg    3660
tgcccaaata tgacataata tttgttaatg tgaggacccc atataaatac catcactatc    3720
agcagtgtga agaccatgcc attaagctta gcatgttgac caagaaagct tgtctgcatc    3780
tgaatcccgg cggaacctgt gtcagcatag gttatggtta cgctgacagg gccagcgaaa    3840
gcatcattgg tgctatagcg cggcagttca agttttcccg ggtatgcaaa ccgaaatcct    3900
cacttgaaga gacggaagtt ctgtttgtat tcattgggta cgatcgcaag gcccgtacgc    3960
acaatcctta caagctttca tcaaccttga ccaacattta tacaggttcc agactccacg    4020
aagccggatg tgcaccctca tatcatgtgg tgcgagggga tattgccacg gccaccgaag    4080
gagtgattat aaatgctgct aacagcaaag gacaacctgg cggaggggtg tgcggagcgc    4140
tgtataagaa attcccggaa agcttcgatt tacagccgat cgaagtagga aaagcgcgac    4200
tggtcaaagg tgcagctaaa catatcattc atgccgtagg accaaacttc aacaaagttt    4260
cggaggttga aggtgacaaa cagttggcag aggcttatga gtccatcgct aagattgtca    4320
acgataacaa ttacaagtca gtagcgattc cactgttgtc caccggcatc tttccgggaa    4380
acaaagatcg actaacccaa tcattgaacc atttgctgac agctttagac accactgatg    4440
cagatgtagc catatactgc agggacaaga atgggaaat gactctcaag gaagcagtgg    4500
ctaggagaga agcagtggag gagatatgca tatccgacga ctcttcagtg acagaacctg    4560
atgcagagct ggtgagggtg catccgaaga gttcttggc tggaaggaag ggctacagca    4620
caagcgatgc caaaacttc tcatatttgg aagggaccaa gtttcaccag gcggccaagg    4680
atatagcaga aattaatgcc atgtggcccg ttgcaacgga ggccaatgag caggtatgca    4740
tgtatatcct cggagaaagc atgagcagta ttaggtcgaa atgccccgtc gaagagtcgg    4800
aagcctcctc accacctagc acgctgcctt gcttgtgcat ccatgccatg actccagaaa    4860
gagtacagcg cctaaaagcc tcacgtccag aacaaattac tgtgtgctca tcctttccat    4920
tgccgaagta tagaatcact ggtgtgcaga agatccaatg ctcccagcct atattgttct    4980
caccgaaagt gcctgcgtat attcatccaa ggaagtatct cgtggaaaca ccaccggtag    5040
acgagactcc ggagccatcg gcagagaacc aatccacaga ggggacacct gaacaaccac    5100
cacttataac cgaggatgag accaggacta gaacgcctga gccgatcatc atcgaagagg    5160
```

```
aagaagagga tagcataagt tgctgtcag atggcccgac ccaccaggtg ctgcaagtcg   5220
aggcagacat tcacgggccg ccctctgtat ctagctcatc ctggtccatt cctcatgcat   5280
ccgactttga tgtggacagt ttatccatac ttgacaccct ggagggagct agcgtgacca   5340
gcggggcaac gtcagccgag actaactctt acttcgcaaa gagtatggag tttctggcgc   5400
gaccggtgcc tgcgcctcga acagtattca ggaaccctcc acatcccgct ccgcgcacaa   5460
gaacaccgtc acttgcaccc agcagggcct gctcgagagg gatcacggga gaaaccgtgg   5520
gatacgcggt tacacacaat agcgagggct tcttgctatg caaagttact gacacagtaa   5580
aaggagaacg ggtatcgttc cctgtgtgca cgtacatccc ggccaccata aactcgagaa   5640
ccagcctggt ctccaacccg ccaggcgtaa atagggtgat tacaagagag gagtttgagg   5700
cgttcgtagc acaacaacaa tgacggtttg atgcgggtgc atacatcttt tcctccgaca   5760
ccggtcaagg gcatttacaa caaaaatcag taaggcaaac ggtgctatcc gaagtggtgt   5820
tggagaggac cgaattggag atttcgtatg ccccgcgcct cgaccaagaa aaagaagaat   5880
tactacgcaa gaaattacag ttaaatccca cacctgctaa cagaagcaga taccagtcca   5940
ggaaggtgga gaacatgaaa gccataacag ctagacgtat tctgcaaggc ctagggcatt   6000
atttgaaggc agaaggaaaa gtggagtgct accgaaccct gcatcctgtt cctttgtatt   6060
catctagtgt gaaccgtgcc ttttcaagcc ccaaggtcgc agtggaagcc tgtaacgcca   6120
tgttgaaaga gaacttttcg actgtggctt cttactgtat tattccagag tacgatgcct   6180
atttggacat ggttgacgga gcttcatgct gcttagacac tgccagtttt tgccctgcaa   6240
agctgcgcag ctttccaaag aaacactcct atttggaacc cacaatacga tcggcagtgc   6300
cttcagcgat ccagaacacg ctccagaacg tcctggcagc tgccacaaaa agaaattgca   6360
atgtcacgca aatgagagaa ttgcccgtat tggattcggc ggcctttaat gtggaatgct   6420
tcaagaaata tgcgtgtaat aatgaatatt gggaaacgtt taaagaaaac cccatcaggc   6480
ttactgaaga aaacgtggta aattacatta ccaaattaaa aggaccaaaa gctgctgctc   6540
tttttgcgaa gacacataat ttgaatatgt tgcaggacat accaatggac aggtttgtaa   6600
tggacttaaa gagagacgtg aaagtgactc caggaacaaa acatactgaa gaacggccca   6660
aggtacaggt gatccaggct gccgatccgc tagcaacagc gtatctgtgc ggaatccacc   6720
gagagctggt taggagatta aatgcggtcc tgcttccgaa cattcataca ctgtttgata   6780
tgtcggctga agactttgac gctattatag ccgagcactt ccagcctggg gattgtgttc   6840
tggaaactga catcgcgtcg tttgataaaa gtgaggacga cgccatggct ctgaccgcgt   6900
taatgattct ggaagactta ggtgtggacg cagagctgtt gacgctgatt gaggcggctt   6960
tcggcgaaat ttcatcaata catttgccca ctaaaactaa atttaaattc ggagccatga   7020
tgaaatctgg aatgttcctc acactgtttg tgaacacagt cattaacatt gtaatcgcaa   7080
gcagagtgtt gagagaacgg ctaaccggat caccatgtgc agcattcatt ggagatgaca   7140
atatcgtgaa aggagtcaaa tcggacaaat taatggcaga caggtgcgcc acctggttga   7200
atatggaagt caagattata gatgctgtgg tgggcgagaa agcgccttat ttctgtggag   7260
ggtttatttt gtgtgactcc gtgaccggca cagcgtgccg tgtggcagac cccctaaaaa   7320
ggctgtttaa gcttggcaaa cctctggcag cagacgatga acatgatgat gacaggagaa   7380
gggcattgca tgaagagtca acacgctgga accgagtggg tattctttca gagctgtgca   7440
aggcagtaga atcaaggtat gaaaccgtag gaacttccat catagttatg gccatgacta   7500
ctctagctag cagtgttaaa tcattcagct acctgagagg ggcccctata actctctacg   7560
```

```
gctaacctga atggactacg acatagtcta gtccgccaag cctcagcgtc gacgccacca   7620
tggaactgct gatcctgaag gccaacgcca tcaccaccat cctgaccgcc gtgaccttct   7680
gcttcgccag cggccagaac atcaccgagg aattctacca gagcacctgc agcgccgtga   7740
gcaagggcta cctgagcgcc ctgcggaccg gctggtacac cagcgtgatc accatcgagc   7800
tgtccaacat caagaaaac aagtgcaacg gcaccgacgc caaggtgaaa ctgatcaagc   7860
aggaactgga caagtacaag aacgccgtga ccgagctgca gctgctgatg cagagcaccc   7920
ccgccaccaa caaccgggcc agaagagagc tgccccggtt catgaactac accctgaaca   7980
acgccaagaa aaccaacgtg accctgagca agaagcggaa gcggcggttc ctgggcttcc   8040
tgctgggcgt gggcagcgcc atcgccagcg gggtggccgt gtccaaggtg ctgcacctgg   8100
aaggcgaggt gaacaagatc aagtccgccc tgctgtccac caacaaggcc gtggtgtccc   8160
tgagcaacgg cgtgagcgtg ctgaccagca aggtgctgga tctgaagaac tacatcgaca   8220
agcagctgct gcccatcgtg aacaagcaga gctgcagcat cagcaacatc gagaccgtga   8280
tcgagttcca gcagaagaac aaccggctgc tggaaatcac ccgggagttc agcgtgaacg   8340
ccggcgtgac cacccccgtg agcacctaca tgctgaccaa cagcgagctg ctgtccctga   8400
tcaatgacat gcccatcacc aacgaccaga aaagctgat gagcaacaac gtgcagatcg   8460
tgcggcagca gagctactcc atcatgagca tcatcaaaga agaggtgctg gcctacgtgg   8520
tgcagctgcc cctgtacggc gtgatcgaca ccccctgctg gaagctgcac accagccccc   8580
tgtgcaccac caacaccaaa gagggcagca acatctgcct gacccggacc gaccggggct   8640
ggtactgcga caacgccggc agcgtgagct tcttcccca gccgagacc tgcaaggtgc   8700
agagcaaccg ggtgttctgc gacaccatga acagcctgac cctgcccctcc gaggtgaacc   8760
tgtgcaacgt ggacatcttc aaccccaagt acgactgcaa gatcatgacc tccaagaccg   8820
acgtgagcag ctccgtgatc acctccctgg gcgccatcgt gagctgctac ggcaagacca   8880
agtgcaccgc cagcaacaag aaccgggca tcatcaagac cttcagcaac ggctgcgact   8940
acgtgagcaa caagggcgtg gacaccgtga gcgtgggcaa cactgtac tacgtgaata   9000
agcaggaagg caagagcctg tacgtgaagg gcgagcccat catcaacttc tacgaccccc   9060
tggtgttccc cagcgacgag ttcgacgcca gcatcagcca ggtcaacgag aagatcaacc   9120
agagcctggc cttcatccgg aagagcgacg agctgctgca caatgtgaat gccggcaaga   9180
gcaccaccaa tatcatgatc accacaatca tcatcgtgat cattgtgatc ctgctgtctc   9240
tgattgccgt gggcctgctg ctgtactgca aggcccgcag caccccgtg accctgtcca   9300
aggaccagct gtccggcatc aacaatatcg ccttctccaa ctgaagtcta gagcggccgc   9360
cgctacgccc aatgatccg accagcaaaa ctcgatgtac ttccgaggaa ctgatgtgca   9420
taatgcatca ggctggtaca ttagatcccc gcttaccgcg gcaatatag caacactaaa   9480
aactcgatgt acttccgagg aagcgcagtg cataatgctg cgcagtgttg ccacataacc   9540
actatattaa ccatttatct agcggacgcc aaaaactcaa tgtatttctg aggaagcgtg   9600
gtgcataatg ccacgcagcg tctgcataac ttttattatt tctttttatta atcaacaaaa   9660
ttttgttttt aacatttcaa aaaaaaaaaa aaaaaaaaaa aaaaaaaaa aaaaaaaagg   9720
gtcggcatgg catctccacc tcctcgcggt ccgacctggg catccgaagg aggacgcacg   9780
tccactcgga tggctaaggg agagccacga gctcctgttt aaaccagctc caattcgccc   9840
tatagtgagt cgtattacgc gcgctcactg gccgtcgttt tacaacgtcg tgactgggaa   9900
```

| | |
|---|---|
| aaccctggcg ttacccaact taatcgcctt gcagcacatc cccctttcgc cagctggcgt | 9960 |
| aatagcgaag aggcccgcac cgatcgccct tcccaacagt tgcgcagcct gaatggcgaa | 10020 |
| tgggacgcgc cctgtagcgg cgcattaagc gcggcgggtg tggtggttac gcgcagcgtg | 10080 |
| accgctacac ttgccagcgc cctagcgccc gctcctttcg ctttcttccc ttcctttctc | 10140 |
| gccacgttcg ccggctttcc ccgtcaagct ctaaatcggg gctcccttt agggttccga | 10200 |
| tttagtgctt tacggcacct cgaccccaaa aaacttgatt agggtgatgg ttcacgtagt | 10260 |
| gggccatcgc cctgatagac ggttttttcgc cctttgacgt tggagtccac gttctttaat | 10320 |
| agtggactct tgttccaaac tggaacaaca ctcaaccctc tctcggtcta ttcttttgat | 10380 |
| ttataaggga ttttgccgat ttcggcctat tggttaaaaa atgagctgat ttaacaaaaa | 10440 |
| tttaacgcga attttaacaa aatattaacg cttacaattt aggtggcact tttcggggaa | 10500 |
| atgtgcgcgg aacccctatt tgtttatttt tctaaataca ttcaaatatg tatccgctca | 10560 |
| tgagacaata accctgataa atgcttcaat aatattgaaa aaggaagagt atgagtattc | 10620 |
| aacatttccg tgtcgccctt attccctttt ttgcggcatt ttgccttcct gttttgctc | 10680 |
| acccagaaac gctggtgaaa gtaaaagatg ctgaagatca gttgggtgca cgagtgggtt | 10740 |
| acatcgaact ggatctcaac agcggtaaga tccttgagag ttttcgcccc gaagaacgtt | 10800 |
| ttccaatgat gagcactttt aaagttctgc tatgtggcgc ggtattatcc cgtattgacg | 10860 |
| ccgggcaaga gcaactcggt cgccgcatac actattctca gaatgacttg gttgagtact | 10920 |
| caccagtcac agaaaagcat cttacggatg gcatgacagt aagagaatta tgcagtgctg | 10980 |
| ccataaccat gagtgataac actgcggcca acttacttct gacaacgatc ggaggaccga | 11040 |
| aggagctaac cgcttttttg cacaacatgg gggatcatgt aactcgcctt gatcgttggg | 11100 |
| aaccggagct gaatgaagcc ataccaaacg acgagcgtga caccacgatg cctgtagcaa | 11160 |
| tggcaacaac gttgcgcaaa ctattaactg gcgaactact tactctagct tcccggcaac | 11220 |
| aattaataga ctggatggag gcggataaag ttgcaggacc acttctgcgc tcggcccttc | 11280 |
| cggctggctg gtttattgct gataaatctg gagccggtga gcgtgggtct cgcggtatca | 11340 |
| ttgcagcact ggggccagat ggtaagccct cccgtatcgt agttatctac acgacgggga | 11400 |
| gtcaggcaac tatggatgaa cgaaatagac agatcgctga gataggtgcc tcactgatta | 11460 |
| agcattggta actgtcagac caagtttact catatatact ttagattgat ttaaaacttc | 11520 |
| attttttaatt taaaaggatc taggtgaaga tcctttttga taatctcatg accaaaatcc | 11580 |
| cttaacgtga gttttcgttc cactgagcgt cagaccccgt agaaaagatc aaaggatctt | 11640 |
| cttgagatcc ttttttttctg cgcgtaatct gctgcttgca acaaaaaaa ccaccgctac | 11700 |
| cagcggtggt ttgtttgccg gatcaagagc taccaactct ttttccgaag gtaactggct | 11760 |
| tcagcagagc gcagatacca aatactgttc ttctagtgta gccgtagtta ggccaccact | 11820 |
| tcaagaactc tgtagcaccg cctacatacc tcgctctgct aatcctgtta ccagtggctg | 11880 |
| ctgccagtgg cgataagtcg tgtcttaccg ggttggactc aagacgatag ttaccggata | 11940 |
| aggcgcagcg gtcgggctga acgggggggtt cgtgcacaca gcccagcttg gagcgaacga | 12000 |
| cctacaccga actgagatac ctacagcgtg agctatgaga aagcgccacg cttcccgaag | 12060 |
| ggagaaaggc ggacaggtat ccggtaagcg gcagggtcgg aacaggagag cgcacgaggg | 12120 |
| agcttccagg gggaaacgcc tggtatcttt atagtcctgt cgggtttcgc cacctctgac | 12180 |
| ttgagcgtcg atttttgtga tgctcgtcag ggggcggag cctatggaaa aacgccagca | 12240 |
| acgcggcctt tttacggttc ctggccttt gctggccttt tgctcacatg ttctttcctg | 12300 |

```
cgttatcccc tgattctgtg gataaccgta ttaccgcctt tgagtgagct gataccgctc    12360
gccgcagccg aacgaccgag cgcagcgagt cagtgagcga ggaagcggaa gagcgcccaa    12420
tacgcaaacc gcctctcccc gcgcgttggc cgattcatta atgcagctgg cacgacaggt    12480
ttcccgactg gaaagcgggc agtgagcgca acgcaattaa tgtgagttag ctcactcatt    12540
aggcacccca ggctttacac tttatgctcc cggctcgtat gttgtgtgga attgtgagcg    12600
gataacaatt tcacacagga aacagctatg accatgatta cgccaagcgc gcaattaacc    12660
ctcactaaag ggaacaaaag ctgggtaccg ggcccacgcg tcggctacaa ttaatacata    12720
accttatgta tcatacacat acgatttagg tgacactata g                        12761
```